US010363269B2

(12) United States Patent
Tareen

(10) Patent No.: US 10,363,269 B2
(45) Date of Patent: Jul. 30, 2019

(54) MODIFIED HEPATITIS POST-TRANSCRIPTIONAL REGULATORY ELEMENTS

(71) Applicant: Juno Therapeutics, Inc., Seattle, WA (US)

(72) Inventor: Semih U. Tareen, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 276 days.

(21) Appl. No.: 14/994,114

(22) Filed: Jan. 12, 2016

(65) Prior Publication Data

US 2016/0199412 A1 Jul. 14, 2016

Related U.S. Application Data

(60) Provisional application No. 62/102,569, filed on Jan. 12, 2015.

(51) Int. Cl.
| A61K 35/17 | (2015.01) |
| C12N 15/86 | (2006.01) |
| C12N 7/00 | (2006.01) |
| C12N 15/85 | (2006.01) |

(52) U.S. Cl.
CPC ............... *A61K 35/17* (2013.01); *C12N 7/00* (2013.01); *C12N 15/85* (2013.01); *C12N 15/86* (2013.01); *C12N 2730/10043* (2013.01); *C12N 2740/15043* (2013.01); *C12N 2740/16041* (2013.01); *C12N 2830/48* (2013.01)

(58) Field of Classification Search
CPC .......... C12N 15/85; C12N 15/86; C12N 7/00; A61K 35/17
See application file for complete search history.

(56) References Cited

U.S. PATENT DOCUMENTS

| 4,452,773 A | 6/1984 | Molday |
| 4,683,202 A | 7/1987 | Mullis |
| 4,690,915 A | 9/1987 | Rosenberg |
| 4,795,698 A | 1/1989 | Owen et al. |
| 5,200,084 A | 4/1993 | Liberti et al. |
| 5,686,279 A | 11/1997 | Finer et al. |
| 5,928,906 A | 7/1999 | Koster et al. |
| 5,994,136 A | 11/1999 | Naldini et al. |
| 6,013,516 A | 1/2000 | Verma et al. |
| 6,040,177 A | 3/2000 | Riddell et al. |
| 6,136,597 A | 10/2000 | Hope et al. |
| 6,410,319 B1 | 6/2002 | Raubitschek et al. |
| 6,451,995 B1 | 9/2002 | Cheung et al. |
| 6,682,907 B1 | 1/2004 | Charneau et al. |
| 6,969,598 B2 | 11/2005 | Olsen et al. |
| 7,070,995 B2 | 7/2006 | Jensen |
| 7,265,209 B2 | 9/2007 | Jensen |
| 7,354,762 B2 | 4/2008 | Jensen |
| 7,419,829 B2 | 9/2008 | Mitrophanous et al. |
| 7,446,179 B2 | 11/2008 | Jensen et al. |
| 7,446,190 B2 | 11/2008 | Sadelain et al. |
| 7,446,191 B2 | 11/2008 | Jensen |
| 8,324,353 B2 | 12/2012 | Jensen |
| 8,389,282 B2 | 3/2013 | Sadelain et al. |
| 8,399,645 B2 | 3/2013 | Campana et al. |
| 8,497,118 B2 | 7/2013 | Jensen |
| 2002/0131960 A1 | 9/2002 | Sadelain et al. |
| 2003/0044981 A1 | 3/2003 | Marasco et al. |
| 2003/0170238 A1 | 9/2003 | Gruenberg et al. |
| 2011/0003380 A1 | 1/2011 | Miltenyi et al. |
| 2013/0149337 A1 | 6/2013 | Cooper et al. |
| 2013/0287748 A1 | 10/2013 | June et al. |
| 2015/0038684 A1 | 2/2015 | Jensen |
| 2015/0118714 A1 | 4/2015 | Kan |
| 2016/0009813 A1 | 1/2016 | Themeli et al. |
| 2016/0045551 A1 | 2/2016 | Brentjens et al. |
| 2016/0122782 A1 | 5/2016 | Crisman et al. |

FOREIGN PATENT DOCUMENTS

| EP | 0 452 342 | 10/1991 |
| EP | 2 537 416 | 12/2012 |
| WO | WO-1992/008796 | 5/1992 |
| WO | WO-1994/028143 | 12/1994 |
| WO | WO-2000/014257 | 3/2000 |
| WO | WO-2009/072003 | 6/2009 |
| WO | WO-2010/033140 | 3/2010 |
| WO | WO-2012/129514 | 9/2012 |
| WO | WO-2013/071154 | 5/2013 |
| WO | WO-2013/123061 | 8/2013 |
| WO | WO-2013/126726 | 8/2013 |

(Continued)

OTHER PUBLICATIONS

US 8,252,592 B2, 08/2012, Sadelain (withdrawn)
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2:e93.
Ao et al "Assessment of the role of the central DNA flap in human immunodeficiency virus type 1 replication by using a single-cycle replication system," J Virol. Mar. 2004;78(6):3170-7.
Botta et al., "Naturally occurring woodchuck hepatitis virus (WHV) deletion mutants in chronically WHV-infected woodchucks," Virology. Nov 25, 2000;277(2):226-34.
Bouchard et al., "The enigmatic X gene of hepatitis B virus," J Virol. Dec. 2004;78(23):12725-34.

(Continued)

*Primary Examiner* — Antonio Galisteo Gonzalez
(74) *Attorney, Agent, or Firm* — Morrison Foerster LLP

(57) ABSTRACT

Provided are polynucleotides containing a modified PRE having a variant X gene that includes one or more stop codons not present in an unmodified, such as wild-type, hepatitis X gene. Also provided are polynucleotides containing a modified PRE having a variant X gene that includes one or more degradation sequences not present in an unmodified, such as wild-type, hepatitis X gene. The modified PRE can be operably linked to a nucleic acid encoding a recombinant protein. Also provided are expression cassettes, viral vectors and cells containing the polynucleotides, and compositions and methods of use thereof.

46 Claims, 6 Drawing Sheets

Specification includes a Sequence Listing.

(56) References Cited

FOREIGN PATENT DOCUMENTS

| WO | WO-2013/166321 | 11/2013 |
|---|---|---|
| WO | WO-2014/031687 | 2/2014 |
| WO | WO-2014/055668 | 4/2014 |
| WO | WO-2015/095895 | 6/2015 |
| WO | WO 2015/157432 | 10/2015 |

OTHER PUBLICATIONS

Brash et al., "Strontium phosphate transfection of human cells in primary culture: stable expression of the simian virus 40 large-T-antigen gene in primary human bronchial epithelial cells," Mol. Cell Biol. (1987) 7:2031-2034.

Carlens et al., "Ex vivo T lymphocyte expansion for retroviral transduction: influence of serum-free media on variations in cell expansion rates and lymphocyte subset distribution," Exp Hematol (2000) 28(10):1137-46.

Carrillo et al., "The Multiple Sequence Alignment Problem in Biology," SIAM J Applied Math (1988) 48:1073.

Catic et al., "Preferred in vivo ubiquitination sites," Bioinformatics Dec. 12, 2004;20(18):3302-7.

Chen et al., "The Woodchuck hepatitis virus X gene is important for establishment of virus infection in Woodchucks," J Virol. Mar. 1993;67(3):1218-1226.

Chicaybam et al., "An efficient low cost method for gene transfer to T lymphocytes," PLoS ONE (2013) 8(3):e60298.

Cho et al., "Human mammalian cell sorting using a highly integrated micro-fabricated fluorescence-activated cell sorter (microFACS)," Lab Chip (2010) 10:1567-1573.

Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.

Cohen et al., "Recognition of fresh human tumor by human peripheral blood lymphocytes transduced with a bicistronic retroviral vector encoding a murine anti-p53 TCR," J Immunol. (2005) 175:5799-5808.

Dardalhon et al., "Lentivirus-mediated gene transfer in primary T cells is enhanced by a central DNA flap," Gene Ther Feb. 2001;8(3):190-8.

Davila et al., "CD19 CAR-targeted T cells induce long-term remission and B Cell Aplasia in an immunocompetent mouse model of B cell acute lymphoblastic leukemia," PLoS ONE (2013) 8(4):e61338.

Donello et al., "Woodchuck hepatitis virus contains a tripartite posttranscriptional regulatory element," J Virol. Jun. 1998;72(6):5085-92.

Dull et al., "A third-generation lentivirus vector with a conditional packaging system", J Virol., Nov. 1998; 72(11):8463-71.

Flajolet et al., "Cellular and viral trans-acting factors modulate N-myc2 promoter activity in woodchuck liver tumors," Oncogene. Aug 28, 1997;15(9):1103-10.

Flajolet et al., "Woodchuck hepatitis virus enhancer I and enhancer II are both involved in N-myc2 activation in woodchuck liver tumors," J Virol. Jul. 1998;72(7):6175-80.

Godin et al., "Microfluidics and photonics for Bio-System-on-a-Chip: a review of advancements in technology towards a microfluidic flow cytometry chip," J Biophoton. (2008) 1(5):355-376.

Gonda et al., "Universality and structure of the N-end rule," J Biol Chem. Oct. 5, 1989;264(28):16700-12.

Gossen et al., "Tight control of gene expression in mammalian cells by tetracycline-responsive promoters," Proc Natl Acad Sci U S A. Jun. 15, 1992;89(12):5547-51.

Hicke et al., "Ubiquitin-binding domains," Nat Rev Mal Cell Biol. Aug. 2005;6(8):610-21.

Huang et al., "DNA transposons for modification of human primary T lymphocytes," Methods Mol Biol (2009) 506:115-126.

Iglesias et al., "Residual HIV-1 DNA Flap-independent nuclear import of cPPT/CtS double mutant viruses does not support spreading infection," Retrovirology. Nov. 10, 2011;8:92.

International Search Report and Written Opinion for PCT/US2016/013109, dated Apr. 7, 2016, 19 pages.

Johnston, et al., "Biolistic transformation: microbes to mice," Nature (1990) 346:776-777.

Kingsman et al., "Potential oncogene activity of the woodchuck hepatitis post-transcriptional regulatory element (WPRE)," Gene Ther. Jan. 2005;12(1):3-4.

Klebanoff et al., "Sorting through subsets: which T-cell populations mediate highly effective adoptive immunotherapy?," J Immunother. (2012) 35(9):651-660.

Koste et al., "T-cell receptor transfer into human T cells with ecotropic retroviral vectors," Gene Therapy (2014) 21:533-538.

Kumar et al., "A truncated mutant (residues 58-140) of the hepatitis B virus X protein retains transactivation function,"Proc Natl Acad Sci U S A. May 28, 1996;93(11):5647-52.

Li et al., "Directed evolution of human T-cell receptors with picomolar affinities by phage display," Nat Biotechnol. (2005) 23:349-354.

Lindemann et al., "Versatile retrovirus vector systems for regulated gene expression in vitro and in vivo," Mol Med. Jul. 1997;3(7):466-76.

Lu et al., "Replication of naturally occurring woodchuck hepatitis virus deletion mutants in primary hepatocyte cultures and after transmission to naive woodchucks," J Virol. Apr. 2001;75(8):3811-8.

Lupton S. D. et al., "Dominant positive and negative selection using a hygromycin phosphotransferase-thymidine kinase fusion gene," Mol. and Cell Biol. (1991) 11:6.

Macejak et al., "Internal initiation of translation mediated by the 5' leader of a cellular mRNA," Nature, (1991); 353:90-94.

Manuri et al., "piggyBac transposon/transposase system to generate CD19-specific T cells for the treatment of B-lineage malignancies," Hum Gene Ther (2010) 21(4):427-437.

Miller, "Human gene therapy comes of age," Nature. Jun. 11, 1992;357(6378):455-60.

Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.

Naldini et al., Efficient transfer, integration, and sustained long-term expression of the transgene in adult rat brains injected with a lentiviral vector, Proc Natl Acad Sci U S A. Oct. 15, 1996;93(21):11382-8.

Naldini et al., "In vivo gene delivery and stable transduction of nondividing cells by a lentiviral vector," Science. Apr. 12, 1996;272(5259):263-7.

Naldini et al., "Lentiviruses as gene transfer agents for delivery to non-dividing cells", Curr Opin Biotechnol., Oct. 9, (1998); 5:457-63.

Ory et al., "A stable human-derived packaging cell line for production of high titer retrovirus/vesicular stomatitis virus G pseudotypes," Proc Natl Acad Sci U S A. Oct. 15, 1996;93(21):11400-6.

Park et al., "Modified HIV-1 based lentiviral vectors have an effect on viral transduction efficiency and gene expression in vitro and in vivo," Mol Ther. Sep. 2001;4(3):164-73.

Park et al., "Treating cancer with genetically engineered T cells," Trends Biotechnol. (2011) 29(11):550-557.

Parkhurst et al., "Characterization of genetically modified T-cell receptors that recognize the CEA:691-699 peptide in the context of HLA-A2.1 on human colorectal cancer cells," Clin Cancer Res. (2009) 15:169-180.

Pelletier et al., "Internal initiation of translation of eukaryotic mRNA directed by a sequence derived from poliovirus RNA," Nature. Jul. 28, 1988; 334(6180):320-5.

Remington: The Science and Practice of Pharmacy, 21st Edition, Journal of Pharmacy Technology, Mar.-Apr. 2006;22:133-134.

Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.

Rogers et al., "Amino acid sequences common to rapidly degraded proteins: the PEST hypothesis," Science. Oct. 17, 1986;234(4774):364-8.

(56) References Cited

OTHER PUBLICATIONS

Rosenberg, et al., "Cell transfer immunotherapy for metastatic solid cancer—what clinicians need to know," Nat Rev Clin Oncol. (2011) 8(10):577-85.
Runkel et al., "Two-codon insertion mutations of the HBx define two separate regions necessary for its trans-activation function," Virology. Dec. 1993;197(2):529-36.
Sadelain et al., "The basic principles of chimeric antigen receptor design," Cancer Discov. (2013) 3(4):388-398.
Schambach et al., "Woodchuck hepatitis virus post-transcriptional regulatory element deleted from X protein and promoter sequences enhances retroviral vector titer and expression," Gene Ther. Apr. 2006;13(7):641-5.
Sharma et al., "Efficient sleeping beauty DNA transposition from DNA minicircles," Molec Ther Nucl Acids (2013) 2, e74.
Smith et al., "The hepatitis B virus post-transcriptional regulatory element contains two conserved RNA stem-loops which are required for function," Nucleic Acids Res. Nov. 1, 1998;26(21):4818-27.
Sugata et al., "Analysis of the X gene promoter of woodchuck hepatitis virus," Virology. Nov. 15, 1994;205(1):314-20.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1):84-9.
Turtle et al., "Engineered T cells for anti-cancer therapy," Curr. Opin. Immunol. (2012) 24(5):633-39.
Van Tendeloo et al., "High-level transgene expression in primary human T lymphocytes and adult bone marrow CD34+ cells via electroporation-mediated gene delivery," Gene Therapy (2000) 7(16):1431-1437.
Varela-Rohena et al., "Control of HIV-1 immune escape by CD8 T cells expressing enhanced T-cell receptor," Nat Med. (2008) 14:1390-1395.
Varshavsky, "The N-end rule: functions, mysteries, uses," Proc Natl Acad Sci U S A. Oct. 29, 1996;93(22):12142-9.
Wang et al., "Inhibition by woodchuck hepatitis virus of class I major histocompatibility complex presentation on hepatocytes is mediated by virus envelope pre-S2 protein and can be reversed by treatment with gamma interferon," J Virol. Sep. 2006;80(17):8541-53.
Wang et al., "Phenotypic and functional attributes of lentivirus-modified CD19-specific human CD8+ central memory T cells manufactured at clinical scale," J Immunother. (2012) 35(9):689-701.
Wigler et al., "Transfer of purified herpes virus thymidine kinase gene to cultured mouse cells," Cell (1997) 11:223-232.
Wu et al., "Adoptive T-cell therapy using autologous tumor-infiltrating lymphocytes for metastatic melanoma: current status and future outlook," Cancer (2012) 18(2):160-75.
Yam et al., "Design of HIV vectors for efficient gene delivery into human hematopoietic cells," Mol. Ther. (2002) 5:479.
Zanta-Boussif et al., "Validation of a mutated PRE sequence allowing high and sustained transgene expression while abrogating WHV-X protein synthesis: application to the gene therapy of WAS," Gene Ther. May 2009;16(5):605-19.
Zhou et al., "Harnessing the ubiquitination machinery to target the degradation of specific cellular proteins," Mol Cell. Sep. 2000;6(3):751-6.
Zoulim et al., "Woodchuck hepatitis virus X protein is required for viral infection in vivo," J Virol. Mar. 1994;68(3):2026-30.
Zufferey et al., "Multiply attenuated lentiviral vector achieves efficient gene delivery in vivo," Nat Biotechnol. Sep. 1997;15(9):871-5.
Zufferey et al., "Woodchuck hepatitis virus posttranscriptional regulatory element enhances expression of transgenes delivered by retroviral vectors," J Virol. Apr. 1999;73(4):2886-92.
Blum et al., "Hepatitis B Virus X Protein Is Not Central to the Viral Life Cycle in Vitro," J. Virol (1992) 66(2):1223-1227.
Kantor et al., "Notable Reduction in Illegitimate Integration Mediated by a PPT-deleted, Nonintegrating Lentiviral Vector," Mol Ther (2011) 19(3):547-556.
Kim et al., "Ubiquitin-dependent and -Independent Proteasomal Degradation of Hepatitis B Virus X protein," Biochem Biophys Res Commun (2008) 366(4):1036-2042.
Minor et al., "Hepatitis B Virus HBx Protein Interactions with the Ubiquitin Proteasome System," Viruses (2014) 6(11):4683-702.
Riviere et al., "Analysis of the Viral Elements Required in the Nuclear Import of HIV-1 DNA," J Virol (2010) 84(2):729-739.
Sidhu et al., "Mass Spectrometric Determination of Disulfide Bonds in the Biologically Active Recombinant HBx Protein of Hepatitis B," Biochemistry (2014) 53(28):4685-4695.
Zanta-Boussif et al., "Validation of a mutated PRE sequence allowing high and sustained transgene expression while abrogating WHV-X protein synthesis: application to the gene therapy of WAS," Gene Ther (2009) 16(5):605-619.

```
SEQ ID NO:1        1 AATCAACCCTCTGGATTACACAAATTTGTGAAAGATTGACTGGTATTCTTAACTATGTTGCT   60
                      ||||||||||||||||||||||||||||||||||||||||||||||||||||||||||||
SEQ ID NO:119      1 AATCAACCCTCTGGATTACACAAATTTGTGAAAGATTGACTGGTATTCTTAACTATGTTGCT   60

SEQ ID NO:1       61 CCTTTTACGCTATGTGGATACGCTGCTTTAATGCCTTTGTATCATGCTATTGCTTCCCGT   120
                      ||||||||||||||||||||||||||||||||||||||||||||||||||||||||||||
SEQ ID NO:119     61 CCTTTTACGCTATGTGGATACGCTGCTTTAATGCCTTTGTATCATGCTATTGCTTCCCGT   120

SEQ ID NO:1      121 ATGGCTTTCATTTTCTCCCTGTATAAATCCTGGTTGCTGTCTCTTTATGAGGAGTTG     180
                      ||||||||||||||||||||||||||||||||||||||||||||||||||||||||||||
SEQ ID NO:119    121 ATGGCTTTCATTTTCTCCCTGTATAAATCCTGGTTGCTGTCTCTTTATGAGGAGTTG     180

SEQ ID NO:1      181 TGGCCCGTTGTCAGGCAACGTGGCGTGGCGTGTGTTTGCTGACGCAACCCCACT   240
                      ||||||||||||||||||||||||||||||||||||||||||||||||||||||||||||
SEQ ID NO:119    181 TGGCCCGTTGTCAGGCAACGTGGCGTGCACTGTGTTTGCTGACGCAACCCCACT   240

SEQ ID NO:1      241 GGTTGGGGCATTGCCACCACCTGTCAGCTCCTTTCCGGACTTTCCTTCGCTTTCCCCCTCCT   300
                      ||||||||||||||||||||||||||||||||||||||||||||||||||||||||||||
SEQ ID NO:119    241 GGTTGGGGCATTGCCACCACCTGTCAGCTCCTTTCCGGACTTTCCTTCGCTTTCCCCCTCCT   300

SEQ ID NO:1      301 ATTGCCACGGCGGAACTCATCGCGCCGCCTGCCCGCCTTGCTGCTGACAGGGGCTCGGCTG   360
                      ||||||||||||||||||||||||||||||||||||||||||||||||||||||||||||
SEQ ID NO:119    301 ATTGCCACGGCGGAACTCATCGCGCCGCCTGCCCGCCTTGCTGCTGACAGGGGCTCGGCTG   360

SEQ ID NO:1      361 TTGGGCACTGACAATTCCGTGGTGTTGTCGGGGAAGCTGA-CGTCCTTTTCCATGGCTGCT   419
                      ||||||||||||||||||||||||||||||||||||| ||||||||||||||
SEQ ID NO:119    361 TTGGGCACTGACAATTCCGTGGTGTTGTCGGGGAAA-TCATCGTCCTTTCCTTGGCTGCT   419

SEQ ID NO:1      420 CGCCTGGTGTTGCACCTGGATTCGCGCGGGGACGTCCTTCTGCTACGTCCCTTCGGCCCT   479
                      ||||||||||||||||||||||||||||||||||||||||||||||||||||||||||||
SEQ ID NO:119    420 CGCCTGGTGTTGCACCTGGATTCGCGCGGGGACGTCCTTCTGCTACGTCCCTTCGGCCCT   479

SEQ ID NO:1      480 CAATCCAGCGGACCTTCCTTCCGGCTCTGCCGGCTCTGCGGCCTCTTCCGCGTCT   539
                      ||||||||||||||||||||||||||||||||||||||||||||||||||||||||||||
SEQ ID NO:119    480 CAATCCAGCGGACCTTCCTTCCGGCTCTGCCGGCTCTGCGGCCTCTTCCGCGTCT   539

SEQ ID NO:1      540 TCGCCTTCGCCCTCAGACGAGTCGGATCTCCCCTTTGGGCCGCCCCCGCCTG   592
                      ||||||||||||||||||||||||||||||||||||||||||||||||||||
SEQ ID NO:119    540 TCGCCTTCGCCCTCAGACGAGTCGGATCTCCCCTTTGGGCCGCCCCCGCCTG   59
```

```
SEQ ID NO:1   184  CCCGTTG-TCAGGCAACGTGGCGTGG--TGTGCACTGTGTTGCTGACCGCAACCCCCACT  240
                   |||||||  ||||||||   ||  ||   |||||||  ||||||||||||  |||||||
SEQ ID NO:21  185  CCCGTTGCTC-GGCAAC--GGCCTGGTCTGTGCCAAGTGTTGCTGACGCAACCCCCACT  241

SEQ ID NO:1   241  GGTTGGGGCATTGCCACCACTGTCAGCTCCTTTCCGGGA-CTTTCGCTTTCCCC-CTCC  298
                   |||||||| ||||  |||||||||||||||||||||||| |||||||||||||  ||||
SEQ ID NO:21  242  GGTTGGGGTTGGCCATAGGCCATCAGCAGCCATG--CGTGGAACCTTTG-TGTCTCCTGC  299

SEQ ID NO:1   299  CTATTGCCACGGCGGAACTCATCGCCGCTGCCTTGCCCGCTGGACAGGGGCTCGGC    358
                   |||||||||||||||||||||||||||||||||||||||||||||||||||||||
SEQ ID NO:21  300  CGATCCATACTGCGGAACTCCTAGCCGCCTTGTTTTCTCGACAGCAGGTCGGAGCAAACC  359

SEQ ID NO:1   359  TGTTGGGCACTGACAATTCCGTGGTGTTGTCGGGGAAGCTGACGTCCTTCCATGGCTGC  418
                   |||||||||||||||||||||| ||||||||||| ||||||||||||||||||||||||
SEQ ID NO:21  360  TCATCGGGACCGACAATTCTGTCGTACTCCCCGCAAGTATACATCGTTTCCATGGCTGC  419

SEQ ID NO:1   419  TCCCTTGTGCACCTGGATTCTGCGCGGGACGTCCTTCTGC-TACCTCCCTTCGGCC  477
                   ||    ||    ||||||||||||||||||||||||||||  |||||||||||||
SEQ ID NO:21  420  TAGGCTTGCTGCAACTGGATCCTGCGCGGACGTCCTT-TGTTTACGTCCCGTCGGCG  478

SEQ ID NO:1   478  CTCAATCCAGCGGACCTTCTTCCCGGACGCCTGCTGCCGGCTCTGCCGGCCT-CTTCCGCG  536
                   ||||||||||||||||||||||||||||||||||||||||||||||||||| |||||||
SEQ ID NO:21  479  CTGAATCCGCGGACGACCCCTCCCGGGCC-GCTTGGGCTCTACCGCCGGCTTCTCCG  537

SEQ ID NO:1   537  TCT  539
                   |||
SEQ ID NO:21  538  TCT  540
```

Figure 2E

MODIFIED HEPATITIS POST-TRANSCRIPTIONAL REGULATORY ELEMENTS

CROSS-REFERENCE TO RELATED APPLICATIONS

This application claims priority from U.S. provisional application No. 62/102,569 filed Jan. 12, 2015, entitled "Modified Hepatitis Post-transcriptional Regulatory Elements," the contents of which is incorporate by reference in its entirety.

INCORPORATION BY REFERENCE OF SEQUENCE LISTING

The present application is being filed with a Sequence Listing in electronic format. The Sequence Listing is provided as a file entitled 735042001800SeqList.txt, created on Jan. 12, 2016, which is 152,051 bytes in size. The information in electronic format of the Sequence Listing is incorporated by reference in its entirety.

FIELD

The present disclosure relates to methods for expressing recombinant molecules and polynucleotides for use in such methods. In particular, the disclosure relates to polynucleotides containing post-transcriptional regulatory elements (PREs) that can enhance expression of recombinant molecules operably linked thereto, such as cis-acting post-transcriptional regulatory elements and modified variants thereof. The modified post-transcriptional regulatory elements include those derived from hepatitis viruses, such as the woodchuck hepatitis virus (WHV), including modified variants of a woodchuck hepatitis virus post-transcriptional regulatory element (WPRE). The modified PREs typically include one or more modifications that reduce the potential for oncogenesis and/or immunogenicity upon introduction into a subject for expression of the recombinant molecule, for example, by preventing expression of certain proteins. In some embodiments, such modifications include one or more stop codon included within a sequence within the PRE encoding a viral X protein or portion thereof. In some embodiments, the polynucleotide includes one or more sequences encoding a site to promote post-translational modification, such as degradation, e.g., a ubiquitination site.

BACKGROUND

Viral vectors can provide an effective delivery system for transferring genetic material into a cell. Nucleic acids within many viral vectors, such as gamma-retroviral and lentiviral vectors, can integrate into the genome of a host cell. Cis-acting elements, such as viral post-transcriptional regulatory elements (PREs), including hepatitis virus PREs and variants thereof, have been used in viral vectors to enhance gene expression. Nucleic acids, expression cassettes, and vectors containing such elements are available. There is a need for improved PRE-containing nucleic acids, cassettes and vectors. Provided are embodiments that address such needs.

SUMMARY

Provided are polynucleotides containing a modified post-transcriptional regulatory element (PRE) that contains a variant X gene that includes a stop codon and/or post-translational degradation sequence that is not present in an unmodified or wild-type hepatitis virus X gene, such as not present in an X gene from a wild-type mammalian hepatitis virus, such as a WHV or HBV. Among the provided polynucleotides are those that contain a modified WPRE containing a variant X gene that includes a stop codon and/or post-translational degradation sequence that is not present in an unmodified or wild-type WHV X gene. The provided polynucleotides include expression cassettes and viral vectors containing such modified PREs. In particular embodiments, the modified PRE is operably linked to a nucleic acid encoding a recombinant protein, e.g. a heterologous protein.

Provided are polynucleotides containing a modified PRE that includes a variant of a wild-type hepatitis virus X gene in which the variant X gene contains a stop codon, such as at least one stop codon, not present in the wild-type X gene. In some embodiments, at least one stop codon, e.g., the first stop codon or each of a plurality of stop codons present in the variant X gene, begins at a position within 36 or 24 nucleotides in the 3' direction from a position in the variant X gene corresponding to the 5' position of a start codon of the wild-type X protein open reading frame. In some embodiments, at least one stop codon, e.g., the first stop codon or one or more of a plurality of stop codons present in the variant X gene, begins at a position within 36 or 24 nucleotides in the 3' direction from a position corresponding to residue 411 of WHV PRE sequence set forth in SEQ ID NO:1 or SEQ ID NO:125 and/or residue 1503 of the sequence set forth in SEQ ID NO:2. In some such embodiments, the variant X gene does not contain an open reading frame of greater than at or about 39 nucleotides in length or greater than at or about 27 nucleotides in length.

Provided are polynucleotides containing a modified PRE that contains a variant of a wild-type hepatitis virus X gene in which the variant X gene contains a stop codon, such as at least one stop codon, not present in the wild-type X gene and beginning at a position within 32 or 30 nucleotides of a start codon of the X gene. In some embodiments, the at least one stop codon, e.g. the first stop codon or one or more of a plurality of stop codons present in the variant X gene, begins at a position within 32 or 30 nucleotides in the 3' direction from a position in the variant X gene corresponding to the 5' position of a start codon of the wild-type X protein open reading frame. In some embodiments, the at least one stop codon, e.g. the first stop codon or one or more of a plurality of stop codons present in the variant X gene, begins at a position within 32 or 30 nucleotides in the 3' direction from a position corresponding to residue 411 of WHV PRE sequence set forth in SEQ ID NO:1 or SEQ ID NO:125 and/or residue 1503 of the sequence set forth in SEQ ID NO:2. In some such embodiments, the variant X gene has an open reading frame of less than or equal to 33 nucleotides in length.

In any of such embodiments of a modified PRE, the at least one stop codon not present in the wild-type X gene includes a plurality of stop codons. Provided are polynucleotides comprising a modified PRE that contains a variant of a wild-type hepatitis virus X gene in which the variant X gene contains a plurality of stop codons not present in the wild-type X gene. In any of such embodiments, the modified PRE contains 2, 3, 4, 5 or 6 stop codons. In some embodiments, the plurality of stop codons comprises at least one stop codon in each reading frame present in the variant X gene. In some embodiments, the plurality of stop codons comprises at least two stop codons in the same reading frame.

In any of such embodiments of a modified PRE containing a plurality of stop codons, the first stop codon among the plurality or one or more of a plurality of stop codons begins at a position within 36, 30 or 24 nucleotides in the 3' direction from a position in the variant X gene corresponding to the 5' position of a start codon of the wild-type X protein open reading frame. In some embodiments of a modified PRE containing a plurality of stop codons, the first stop codon among the plurality or one or more of a plurality of stop codons begins at a position within 36, 30 or 24 nucleotides in the 3' direction from a position in the variant X gene corresponding to residue 411 of WHV post-transcriptional regulatory element (WPRE) sequence set forth in SEQ ID NO: 1 or SEQ ID NO:125 and/or residue 1503 of the WHV sequence set forth as SEQ ID NO: 2. In some such embodiments, the variant X gene does not comprise an open reading frame of greater than at or about 39 nucleotides in length, greater than at or about 30 nucleotides in length or greater than at or about 27 nucleotides in length.

In any of such embodiments, the provided polynucleotides also can include a nucleic acid encoding a recombinant protein. In particular embodiments, the modified PRE is operably linked to the nucleic acid encoding the recombinant protein.

In some embodiments of any of the provided polynucleotides, the at least one stop codon, e.g., the first stop codon or one or more of a plurality of stop codons present in the variant X gene, begins at a position within or within at least or at 9, 12, 15, 18 or 21 nucleotides in the 3' direction from a position in the variant X gene corresponding to the 5' position of a start codon of the wild-type X protein open reading frame. In some embodiments of any of the provided polynucleotides, the at least one stop codon, e.g., the first stop codon or one or more of a plurality of stop codons present in the variant X gene, begins at a position within or within at least or at 9, 12, 15, 18, 21 nucleotides in the 3' direction from a position in the variant X gene corresponding to residue 411 of WHV post-transcriptional regulatory element (WPRE) sequence set forth in SEQ ID NO: 1 or SEQ ID NO:125 and/or residue 1503 of the WHV sequence set forth as SEQ ID NO: 2. In some embodiments, the modified PRE contains at least one stop codon, such as 1, 2, 3, 4 or 5 stop codons, in which one or more stop codons of the plurality begins at a position within or within at least or at a nucleotide position corresponding to position 420, 423, 426, 429 or 432 of the sequence set forth in SEQ ID NO:1 or 125. In some such embodiments, the variant X gene does not comprise an open reading frame of greater than or at or about 24 nucleotides in length, greater than at or about 21 nucleotides in length, greater than at or about 18 nucleotides in length, greater than at or about 15 nucleotides in length, or greater than at or about 12 nucleotides in length.

In some embodiments of any of the provided polynucleotides, the at least one stop codon, e.g., the first stop codon or one or more of a plurality of stop codons present in the variant X gene, begins at a position within or within at least or at 9, 13, 17 or 21 nucleotides in the 3' direction from a position in the variant X gene corresponding to the 5' position of a start codon of the wild-type X protein open reading frame. In some embodiments of any of the provided polynucleotides, the at least one stop codon, e.g., the first stop codon or one or more of a plurality of stop codons present in the variant X gene, begins at a position within or within at least or at 9, 13, 17 or 21 nucleotides in the 3' direction from a position in the variant X gene corresponding to residue 411 of WHV post-transcriptional regulatory element (WPRE) sequence set forth in SEQ ID NO: 1 or SEQ ID NO:125 and/or residue 1503 of the WHV sequence set forth as SEQ ID NO: 2. In some embodiments, the modified PRE contains at least one stop codon, such as 1, 2, 3 or 4 stop codons, in which one or more of a plurality of stop codons begins at a position within or within at least or at a nucleotide position corresponding to position 420, 424, 428 or 432 of the sequence set forth in SEQ ID NO: 1 or SEQ ID NO:125. In some such embodiments, the variant X gene does not comprise an open reading frame of greater than at or about 24 nucleotides in length, greater than at or about 21 nucleotides in length, greater than at or about 16 nucleotides in length, or greater than at or about 12 nucleotides in length.

In some embodiments, the unmodified or wild-type X gene comprises the sequence of nucleotides set forth in SEQ ID NO: 221, and the variant X gene contains at least one stop codon, such as 1, 2, 3, 4 or 5 stop codons introduced therein. In some embodiments, a plurality of stop codons are introduced, where at least one stop codon is introduced in each reading frame therein. In some embodiments, a plurality of stop codons is introduced where at least two stop codons are introduced in the same reading frame present therein. In some embodiments, the modified PRE contains a variant X gene that contains at least one stop codon, such as 1, 2, 3 or 4 stop codons, in which one or more begins at a position within or within at least or at position 9, 13, 17 or 21 in the 3' direction from a position in the variant X gene corresponding to the 5' position of the ATG start codon set forth in SEQ ID NO:221. In some embodiments, the modified PRE contains a variant X gene that comprises the sequence of nucleotides set forth in SEQ ID NO:28.

In some embodiments of any of the provided polynucleotides, the modified PRE contains a beta stem loop corresponding to nucleotide residues 448-470 of SEQ ID NO:1 or SEQ ID NO:125. In some embodiments of any of the provided polynucleotides, the modified PRE does not contain a nucleotide change in a position within the beta stem loop corresponding to nucleotides 448-470 of SEQ ID NO:1 or SEQ ID NO:125. In some embodiments of any of the provided polynucleotides, the stop codon or stop codons does not comprise a nucleotide in a position within the beta stem loop corresponding to one or more of nucleotides positions 448-470 of SEQ ID NO:1 or SEQ ID NO:125.

In any of such embodiments, the modified PRE contains a stop codon selected from among: a stop codon beginning at position 9 in the 3' direction from a position in the variant X gene corresponding to the 5' position of a start codon of the wild-type X protein open reading frame and/or at a nucleotide position corresponding to position 420 in the sequence set forth in SEQ ID NO:1 or SEQ ID NO:125; a stop codon beginning at position 13 in the 3' direction from a position in the variant X gene corresponding to the 5' position of a start codon of the wild-type X protein open reading frame and/or at a nucleotide position corresponding to position 424 in the sequence set forth in SEQ ID NO:1 or SEQ ID NO:125; a stop codon beginning at position 17 in the 3' direction from a position in the variant X gene corresponding to the 5' position of a start codon of the wild-type X protein open reading frame and/or at a nucleotide position corresponding to position 428 in the sequence set forth in SEQ ID NO:1 or SEQ ID NO:125; and/or a stop codon beginning at position 21 in the 3' direction from a position in the variant X gene corresponding to the 5' position of a start codon of the wild-type X protein open reading frame and/or at a nucleotide position corresponding to position 432 in the sequence set forth in SEQ ID NO:1 or SEQ ID NO:125.

In any of such embodiments, the stop codon can be an amber (TAG), ochre (TAA) or opal (TGA) stop codon. In some embodiments, the stop codon can be an amber (TAG) or opal (TGA) stop codon. In any of such embodiments, the stop codon, such as each of a plurality of stop codons, is introduced by nucleotide substitution, deletion or insertion.

In some embodiments of any of such polynucleotides, the variant X gene in the modified PRE is no more than 180 nucleotides in length or is no more than at or about 210 nucleotides in length. In some embodiments of any of such polynucleotides, the variant X gene is at least at or about 90 nucleotides in length or at least about 120 nucleotides in length or is at least at or about 180 nucleotides in length.

In some embodiments of any of such polynucleotides, the variant X gene can be a variant of a wild-type or unmodified mammalian hepatitis X gene or a partial or truncated portion thereof. In some embodiments, the wild-type or unmodified X gene can include a partial X gene encoding a truncated X protein, such as is present in a wild-type or unmodified PRE. In some embodiments, the wild-type or unmodified mammalian hepatitis X gene or partial X gene is or is derived from a wild-type woodchuck hepatitis virus (WHV) X gene. In some embodiments, the wild-type or unmodified WHV X gene contains the nucleotide sequence of SEQ ID NO:9 or is a partial X gene thereof. In some embodiments, the wild-type or unmodified WHV X gene contains the sequence of nucleotides set forth as nucleotides 411-592 of any of SEQ ID NOS: 1 and 12-20 or nucleotides 411-589 of SEQ ID NO:125.

In some embodiments of any of such polynucleotides, the modified PRE can contain at least two or at least three cis-acting post-transcriptional regulatory subelements of a wild-type hepatitis virus PRE or functional variant(s) thereof. In some such embodiments, the at least two or at least three subelements comprise a wild-type PRE alpha subelement or functional variant thereof, a functional variant of a wild-type PRE beta subelement, and/or a wild-type PRE gamma subelement or functional variant thereof. In some embodiments, the modified PRE comprises an alpha subelement of a wild-type hepatitis virus PRE or functional variant thereof and a functional variant of a wild-type PRE beta subelement. In any of such embodiments, the alpha subelement can comprise the sequence of SEQ ID NO: 3, SEQ ID NO:4 or SEQ ID NO:5 or a variant thereof, the beta subelement can comprise a variant of the sequence of SEQ ID NO: 6 or SEQ ID NO:7, and/or the gamma subunit can comprise the sequence of SEQ ID NO: 8 or variant thereof.

In some embodiments of any of such polynucleotides, the wild-type or unmodified hepatitis virus PRE can be a wild-type mammalian hepatitis PRE. In some embodiments, the wild-type or unmodified mammalian hepatitis virus PRE contains the sequence of nucleotides set forth in any of SEQ ID NOS: 1 and 12-27 or is a functional portion thereof that exhibits post-transcriptional activity. In some cases, one or more N- or C-terminal amino acid residues can be deleted or removed without substantial effect on the activity of the PRE. In some embodiments, the wild-type or unmodified hepatitis virus PRE has the sequence set forth in SEQ ID NO:125. In some embodiments, the wild-type mammalian hepatitis PRE is a wild-type woodchuck hepatitis virus PRE (WPRE).

In any of such embodiments of the provided polynucleotides, the modified PRE can be modified with reference to a wild-type or unmodified hepatitis PRE that comprises the sequence of nucleotides set forth in SEQ ID NO:1 or SEQ ID NO:125, a sequence of nucleotides that exhibits at least 94%, 95%, 96%, 97%, 98% or 99% sequence identity to SEQ ID NO:1 or SEQ ID NO:125, or a functionally active portion thereof that exhibits post-transcriptional activity, so long as the variant X gene contains at least one stop codon not present in the corresponding wild-type hepatitis PRE.

In any of such embodiments of the provided polynucleotides, the wild-type or unmodified hepatitis PRE can contain the sequence of nucleotides set forth in any of SEQ ID NOS: 1, 12-20 or 125. In some embodiments, the wild-type or unmodified hepatitis PRE can contain the nucleotide sequence of SEQ ID NO: 1. In some embodiments, the wild-type or unmodified hepatitis PRE can contain the nucleotide sequence of SEQ ID NO: 125.

In some embodiments of any of the polynucleotides, the variant X gene can contain a start codon beginning at a position corresponding to position 411 of SEQ ID NO: 1 or SEQ ID NO:125. In some embodiments, the start codon is an ATG start codon.

In some embodiments of any of the polynucleotides, the variant X gene can further contain a promoter operably linked to the variant X gene. In some embodiments, the promoter is a wild-type X-gene promoter comprising the sequence set forth in SEQ ID NO: 11 or a wild-type WHV X gene promoter sequence.

In some embodiments of any of the polynucleotides, the modified PRE can be selected from: a) a modified PRE comprising a sequence of nucleotides that exhibits at least 65%, 70%, 75%, 80%, 85%, 86%, 87%, 88%, 89%, 90%, 91%, 92%, 93%, 94%, 95%, 96%, 97%, 98% or 99% sequence identity to SEQ ID NO:1 or SEQ ID NO:125, in which the modified PRE contains a variant X gene having at least one stop codon not present in SEQ ID NO:1 or SEQ ID NO:125; or b) a modified PRE comprising a portion of the sequence of nucleotides of a) in which the portion contains a variant X gene comprising the at least one stop codon and the portion exhibits post-transcriptional activity. In some embodiments, the variant X gene contains at least 2 stop codons, at least 3 stop codons or at least 4 stop codons. In some embodiments, the variant X gene comprises a stop codon in each reading frame present in said variant X gene.

In some embodiments, the variant X gene comprises the sequence of nucleotides set forth in any of SEQ ID NOS: 44-58 or 141-155. In some embodiments, the modified PRE comprises the sequence of nucleotides set forth in any of SEQ ID NOS:29-43 or 126-140.

In some embodiments of any of the provided polynucleotides, the modified PRE does not contain any modifications in addition to the at least one stop codon not present in the wild-type or unmodified PRE, such as not present in SEQ ID NO:1 or SEQ ID NO:125. In some embodiments of any of the provided polynucleotides, the modified PRE contains additional modifications in addition to the at least one stop codon as compared to the sequence of the wild-type or unmodified PRE, such as compared to SEQ ID NO:1 or SEQ ID NO:125.

In some embodiments of any of the provided polynucleotides, the variant X gene further contains a variant start codon comprising one or more nucleotide differences compared to a wild-type hepatitis virus X gene start codon. In some embodiments, the variant start codon contains one or more nucleotide differences compared to the start codon corresponding to nucleotide positions 411-413 of SEQ ID NO: 1 or SEQ ID NO:125. In some such embodiments, the one or more differences results in restricted or prevented translation initiation from said start codon. In some such embodiments, the variant X gene comprises the sequence of nucleotides set forth in any of SEQ ID NOS: 74-88 or 171-185 and/or the modified PRE comprises the sequence of nucleotides set forth in any of SEQ ID NOS:59-73 or 156-170.

In some embodiments of any of the provided polynucleotides, the variant X gene contains a variant promoter operably linked to the variant X gene in which the variant promoter comprises one or more nucleotide differences compared to a wild-type hepatitis virus X gene promoter. In some embodiments, the variant promoter contains one or more nucleotide differences compared to the promoter set forth as SEQ ID NO: 11. In some embodiments, the one or more differences results in restricted or prevention of transcription from said promoter. In some such embodiments, the modified PRE comprises the sequence of nucleotides set forth in any of SEQ ID NOS: 89-118 or 186-215.

In some embodiments of any of the provided polynucleotides, upon introduction of the polynucleotide into a eukaryotic cell, no polypeptide of a length greater than 12, 11, 10, 9, or 8 amino acids in length encoded by said variant X gene is produced. In some embodiments of any of the provided polynucleotides, the polynucleotide is incapable of producing a polypeptide of a length greater than 12, 11, 10, 9, or 8 amino acids in length encoded by said variant X gene.

In some embodiments of any of the provided polynucleotides, the modified PRE encodes an RNA that promotes nuclear RNA export and/or increases mRNA stability. In some embodiments of any of the provided polynucleotides, the modified PRE encodes an RNA polynucleotide that promotes nuclear RNA export and/or increases mRNA stability, wherein said promotion of nuclear RNA export and/or mRNA stability increases expression of the recombinant protein. In some embodiments of any of the provided polynucleotides, the modified PRE retains the post-transcriptional activity of the corresponding wild-type or unmodified hepatitis PRE and/or the PRE set forth in SEQ ID NO:1, SEQ ID NO:125, SEQ ID NO:119, SEQ ID NO:120 and/or SEQ ID NO:216. In some such embodiments, the modified PRE exhibits at least 75%, 80%, 85%, 90%, 95%, 100%, 110%, 120% or 130% or more of the post-transcriptional activity of the corresponding wild-type or unmodified hepatitis PRE and/or the PRE set forth in SEQ ID NO:1, SEQ ID NO:125, SEQ ID NO:119, SEQ ID NO:120 and/or SEQ ID NO:216. In some embodiments, the post-transcriptional activity of the modified PRE can be assessed by monitoring gene expression of an operably linked nucleic acid encoding a recombinant protein.

In some embodiments of any of the provided polynucleotides, the variant X gene further contains a sequence encoding a post-translational modification signal not present in the wild-type hepatitis virus X gene.

Also provided are polynucleotides containing a modified PRE that includes a variant of a wild-type or unmodified hepatitis virus X gene in which the variant X gene contains a sequence encoding a post-translational modification signal not present in the wild-type or unmodified hepatitis virus X gene. In some embodiments of any of the provided polynucleotides, the post-translational modification signal contains a ubiquitination site.

In some embodiments of any of the provided polynucleotides, the post-translational modification signal contains a first codon beginning at a position within or within at least 2, 3, 4, 5 or 6 nucleotides in the 3' direction from a position in the variant X gene corresponding to the 5' position of a start codon of the X protein open reading frame, wherein the first codon encodes a glycine, arginine, glutamic acid, phenylalanine, aspartate, cysteine, lysine, asparagine, serine, tyrosine, tryptophan, histidine, or leucine residue according to the N-end rule; and optionally a second codon beginning at a position within or within at least 2, 3, 4, 5 or 6 nucleotides in the 3' direction from a position in the variant X gene corresponding to the 5' position of a start codon of the X protein open reading frame, wherein the second codon encodes a glutamic acid or asparagine residue according to the N-end rule.

In some embodiments of any of the provided polynucleotides, the post-translational modification signal contains one or more PEST sequences.

In some embodiments of any of the provided polynucleotides, the polynucleotide contains a nucleic acid encoding a recombinant protein operably linked to the modified PRE and a variant X gene containing a sequence encoding a post-translational modification signal not present in the wild-type or unmodified hepatitis virus X gene.

In some embodiments of any of the provided polynucleotides, the variant X gene contains a sequence encoding a post-translational modification signal containing a beta stem loop corresponding to nucleotide residues 448-470 of SEQ ID NO:1 or SEQ ID NO:125. In some embodiments of any of the provided polynucleotides, the variant X gene contains a sequence encoding a post-translational modification signal that does not contain a nucleotide change in a position within the beta stem loop corresponding to nucleotides 448-470 of SEQ ID NO:1 or SEQ ID NO:125.

In some embodiments of any of the provided polynucleotides, the variant X gene is no more than 180 nucleotides in length or is no more than at or about 210 nucleotides in length. In some embodiments of any of the provided polynucleotides, the variant X gene is at least at or about 90 nucleotides in length or at least about 120 nucleotides in length or is at least at or about 180 nucleotides in length.

In some embodiments of any of the provided polynucleotides, the variant X gene is a variant of a wild-type or unmodified mammalian hepatitis X gene or a partial or truncated portion thereof. In some embodiments, the wild-type or unmodified X gene can include a partial X gene encoding a truncated X protein, such as is present in a wild-type or unmodified PRE. In some embodiments of any of the provided polynucleotides, the wild-type or unmodified mammalian hepatitis X gene or partial X gene is or is derived from a wild-type woodchuck hepatitis virus (WHV) X gene. In some embodiments, the wild-type or unmodified WHV X gene contains the nucleotide sequence of SEQ ID NO:9, the sequence of nucleotides set forth as nucleotides 1503-1928 of SEQ ID NO: 2 or is a partial X gene thereof. In some embodiments of any of the provided polynucleotides, the wild-type or unmodified WHV X gene contains the sequence of nucleotides set forth as nucleotides 411-592 of any of SEQ ID NOS: 1 and 12-20 or nucleotides 411-589 of SEQ ID NO:125.

In some embodiments of any of the provided polynucleotides, the modified PRE contains at least two or at least three cis-acting post-transcriptional regulatory subelements of a wild-type hepatitis virus PRE or functional variant(s) thereof. In some embodiments of any of the provided polynucleotides, the at least two or at least three subelements contain a wild-type PRE alpha subelement or functional variant thereof, a functional variant of a wild-type PRE beta subelement, and/or a wild-type PRE gamma subelement or functional variant thereof. In some embodiments of any of the provided polynucleotides, the modified PRE contains an alpha subelement of a wild-type hepatitis virus PRE or functional variant thereof and a functional variant of a wild-type PRE beta subelement. In some embodiments of any of the provided polynucleotides, the alpha subelement contains the sequence of SEQ ID NO: 3, SEQ ID NO:4 or SEQ ID NO:5 or a variant thereof, the beta subelement contains a variant of the sequence of SEQ ID NO: 6 or SEQ ID NO:7, and/or the gamma subunit contains the sequence of SEQ ID NO: 8 or variant thereof.

In some embodiments of any of the provided polynucleotides, the wild-type or unmodified hepatitis virus PRE is a wild-type mammalian hepatitis PRE. In some embodiments of any of the provided polynucleotides, the wild-type or unmodified mammalian hepatitis virus PRE contains the sequence of nucleotides set forth in any of SEQ ID NOS: 1, 12-27 or 125. In some embodiments of any of the provided polynucleotides, the wild-type mammalian hepatitis PRE is a wild-type woodchuck hepatitis virus PRE (WPRE).

In some embodiments of any of the provided polynucleotides, the modified PRE is selected from among: a) a modified PRE comprising a variant X gene of a wild-type or unmodified hepatitis PRE, the wild-type or unmodified hepatitis PRE containing the sequence of nucleotides set forth in SEQ ID NO:1 or SEQ ID NO:125 or a sequence of nucleotides that exhibits at least 85%, 86%, 87%, 88%, 89%, 90%, 91%, 92%, 93%, 94%, 95%, 96%, 97%, 98% or 99% sequence identity to SEQ ID NO:1 or SEQ ID NO:125, wherein the variant X gene contains a sequence encoding a post-translational modification signal not present in the wild-type or unmodified hepatitis virus X gene; and b) a modified PRE containing a portion of the sequence of nucleotides of a), the portion containing a variant X gene containing the sequence encoding a post-translational modification signal, wherein the portion exhibits post-transcriptional activity.

In some embodiments of any of the provided polynucleotides, the variant X gene contains a start codon beginning at a position corresponding to position 411 of SEQ ID NO: 1 or SEQ ID NO:125. In some embodiments of any of the provided polynucleotides, the start codon is an ATG start codon. In some embodiments of any of the provided polynucleotides, the variant X gene contains a promoter operably linked to said variant X gene. In some embodiments of any of the provided polynucleotides, the promoter is a wild-type X-gene promoter containing the sequence set forth in SEQ ID NO: 11 or a wild-type WHV X gene promoter sequence.

In some embodiments of any of the provided polynucleotides, the modified PRE is selected from among: a) a modified PRE comprising a sequence of nucleotides that exhibits at least 65%, 70%, 75%, 80%, 85%, 86%, 87%, 88%, 89%, 90%, 91%, 92%, 93%, 94%, 95%, 96%, 97%, 98% or 99% sequence identity to SEQ ID NO:1 or SEQ ID NO:125, the modified PRE containing a variant X gene containing a sequence encoding a post-translational modification signal not present in SEQ ID NO:1 or SEQ ID NO:125; and b) a modified PRE containing a portion of the sequence of nucleotides of a), the portion containing a variant X gene containing the sequence encoding the post-translational modification, wherein the portion exhibits post-transcriptional activity.

In some embodiments of any of the provided polynucleotides, the variant X gene contains up to 1, 2, 3, 4, 5, 6, 7, 8, 9, 10, 11 or 12 nucleotide changes.

In some embodiments of any of the provided polynucleotides, the modified PRE does not contain any modifications in addition to the sequence encoding a post-translational modification signal. In some embodiments of any of the provided polynucleotides, the modified PRE contains additional modification(s) in addition to the sequence encoding a post-translational modification signal not present in the wild-type or unmodified hepatitis virus X gene. In some embodiments of any of the provided polynucleotides, the additional modification(s) are in the variant X gene. In some embodiments of any of the provided polynucleotides, the additional modification(s) results in a variant X gene encoding an inactive X protein and/or a truncated X protein.

In some embodiments of any of the provided polynucleotides, the modified PRE encodes an RNA that promotes nuclear RNA export and/or increases mRNA stability. In some embodiments of any of the provided polynucleotides, the promotion of nuclear RNA export and/or mRNA stability increases expression of the recombinant protein.

In some embodiments of any of the provided polynucleotides, the modified PRE retains the post-transcriptional activity of the corresponding wild-type or unmodified hepatitis PRE and/or the PRE set forth in SEQ ID NO:1, SEQ ID NO: 119, SEQ ID NO: 120, SEQ ID NO: 125 or SEQ ID NO:216. In some such embodiments, the modified PRE exhibits at least 75%, 80%, 85%, 90%, 95%, 100%, 110%, 120% or 130% or more of the post-transcriptional activity of the corresponding wild-type or unmodified hepatitis PRE and/or the PRE set forth in SEQ ID NO:1, SEQ ID NO:125, SEQ ID NO:119, SEQ ID NO:120 and/or SEQ ID NO:216. In some embodiments, the post-transcriptional activity of the modified PRE can be assessed by monitoring gene expression of an operably linked nucleic acid encoding a recombinant protein.

In some embodiments, any of the provided polynucleotides can further contain viral nucleic acid containing a variant Flap, wherein the variant Flap contains a deletion of all or a portion of the nucleotides corresponding to the central polypurine tract (cPPT) and/or the central termination sequence (CTS) regions of a wild-type or unmodified Flap sequence. In such embodiments, the polynucleotides contain a modified PRE and a variant Flap. In some embodiments, such elements are operably linked to nucleic acid encoding a recombinant protein and/or result in an increase in efficiency of gene transfer of a heterologous nucleic acid encoding a recombinant protein compared to the absence of such elements.

Also provided are polynucleotides containing a variant Flap, wherein the variant Flap contains a deletion of all or a portion of the nucleotides corresponding to the central polypurine tract (cPPT) and/or the central termination sequence (CTS) regions of a wild-type or unmodified Flap sequence. In some embodiments, the polynucleotide containing a variant Flap can further contain nucleic acid encoding a recombinant protein. In some embodiments, the presence of a polynucleotide containing a variant Flap, while deleted for all or a portion of the cPPT and CTS that are involved in forming the Flap structure, nevertheless can successfully transduce or transfer into cells with the nucleic acid encoding the recombinant protein.

In some embodiments of any of the provided polynucleotides containing a variant Flap, the variant Flap contains a deletion of all or a portion of the nucleotide corresponding to the cPPT and the CTS. In some embodiments, all of the nucleotide residues corresponding to cPPT and all of the nucleotide residues corresponding to the CTS are deleted and/or the variant Flap does not contain nucleotide residues corresponding to the cPPT or nucleotide residues corresponding to the CTS. In some embodiments of any of the provided polynucleotides, the variant Flap contains deletion of all or a contiguous portion of nucleotides corresponding to nucleotides in the cPPT region set forth in SEQ ID NO: 123. In some embodiments of any of the provided polynucleotides, the variant Flap contains deletion of all or a contiguous portion of nucleotides corresponding to nucleotides in the CTS region set forth in SEQ ID NO: 124. In some embodiments of any of the provided polynucleotides, the variant Flap contains deletion of all or a contiguous portion of nucleotides corresponding to nucleotides in the cPPT region set forth in SEQ ID NO:123 and deletion of all or a contiguous portion of nucleotides corresponding to nucleotides in the CTS region set forth in SEQ ID NO:124.

In any of such embodiments of a polynucleotide containing a variant Flap, the variant Flap is modified or comprises modifications as compared to a sequence containing a wild-type or unmodified Flap. In some embodiments, the wild-type or unmodified Flap sequence contains from or from about 80 to 200 contiguous nucleotides that includes the cPPT or CTS regions of a retrovirus, which optionally is a lentivirus. In some embodiments, the retrovirus is a lentivirus. In some embodiments, the lentivirus is HIV-1. In some embodiments, the wild-type or unmodified Flap contains a) the sequence of nucleotides set forth in SEQ ID NO:121; b) a sequence of nucleotides comprising at least 85%, 86%, 87%, 88%, 89%, 90%, 91%, 92%, 93%, 94%, 95%, 96%, 97%, 98% or 99% sequence identity to the sequence of nucleotides set forth in SEQ ID NO:121 that contains the cPPT and CTS regions; or c) a contiguous portion of a) or b) that includes the cPPT and CTS regions.

In some embodiments, the viral nucleic acid containing the variant Flap is or comprises a sequence of nucleotides that exhibits at least 70%, 71%, 72%, 73%, 74%, 75%, 76%, 77%, 78%, 79%, 80%, 85%, 90% or 95% sequence identity to SEQ ID NO:121, said variant Flap lacking all or a portion of the cPPT and CTS regions. In some embodiments of any of the provided polynucleotides, the viral nucleic acid is or contains the sequence set forth in SEQ ID NO:122.

In some embodiments of any of the provided polynucleotides, the polynucleotide contains a) a variant Flap that is or comprises the sequence of SEQ ID NO: 122 or a sequence having at least at or about 90%, 91%, 92%, 93%, 94%, 95%, 96%, 97%, 98%, or 99% sequence identity to SEQ ID NO:122, said variant Flap lacking all or a portion of the cPPT and CTS regions of the corresponding wild-type or unmodified Flap or of the sequence set forth in SEQ ID NO:121; and b) a modified PRE that is or comprises the sequence of SEQ ID NO:29 or 126 or a sequence having at least at or about 90%, 91%, 92%, 93%, 94%, 95%, 96%, 97%, 98%, or 99% sequence identity to SEQ ID NO:29 or 126, said modified PRE containing at least one stop codon in the variant X gene of the modified PRE not present in a wild-type or unmodified X gene or not present in a wild-type or unmodified PRE containing an X gene, such as not present in SEQ ID NO:1 or SEQ ID NO:125.

In some embodiments of any of the provided polynucleotides, the modified WPRE and/or variant Flap is operably linked to nucleotides encoding a recombinant protein that is or contains a recombinant receptor. In some embodiments of any of the provided polynucleotides, the recombinant receptor is an antigen receptor and/or a chimeric receptor. In some embodiments of any of the provided polynucleotides, the recombinant receptor is a functional non-TCR antigen receptor or a transgenic TCR. In some embodiments of any of the provided polynucleotides, the recombinant receptor is a chimeric antigen receptor (CAR).

In some embodiments, also provided is an expression cassette that contains any of the provided polynucleotides and a promoter operably linked to a nucleic acid encoding a recombinant protein. In some embodiments, also provided is a vector that contains any of the provided polynucleotides or expression cassettes. In some embodiments of any of the provided vectors, the vector is a viral vector. In some embodiments of any of the provided vectors, the vector is a retroviral vector. In some embodiments of any of the provided vectors, the vector is a lentiviral vector. In some embodiments, the viral vector is a lentiviral vector that is derived from HIV-1.

In some embodiments, also provided is a cell that contains any of the provided polynucleotides, expression cassettes or any of the provided vectors. In some embodiments of any of the provided cells, the cell is a T cell, a natural killer (NK) cell, an iPS cell, or an iPS-derived cell.

In some embodiments, also provided is a virus particle that contains any of the provided vectors.

In some embodiments, also provided are methods that include introducing any of the provided polynucleotides, expression cassettes, vectors, or virus particles into a cell, under conditions whereby expression of the recombinant protein is effected in the cell. In some embodiments of any of the provided methods, the introduction is effected by transducing the cell with the vector or virus particle. In some embodiments, the introduction is effected by transfecting the cell with the vector; and/or the introduction is effected by electroporation of the cell with the vector. In some embodiments of any of the provided methods, the recombinant protein is expressed at a level that is increased compared to that achieved by introducing the vector in the absence of the modified PRE or a corresponding vector that does not contain the modified PRE or a PRE.

Also provided is a cell or cells produced by any of the provided methods.

Also provided is a pharmaceutical composition that contains a cell of any of the provided embodiments and a pharmaceutically effective carrier.

Also provided are methods of treatment that include administering to a subject having a disease or condition any of the provided polynucleotides, vectors, virus particles, cells, or pharmaceutical compositions.

In some embodiments of any of the provided methods of treatment, the method results in expression of the recombinant protein encoded by the polynucleotide. In some embodiments, the recombinant protein comprises a recombinant receptor that specifically binds to a ligand expressed by the disease or condition or a cell or tissue thereof. In some embodiments of any of the provided methods, the receptor is an antigen receptor and the ligand is an antigen specific for and/or associated with the disease or condition. In some embodiments of any of the provided methods, the disease or condition is a cancer, and autoimmune disorder, or an infectious disease.

BRIEF DESCRIPTION OF THE FIGURES

Figure 2A:
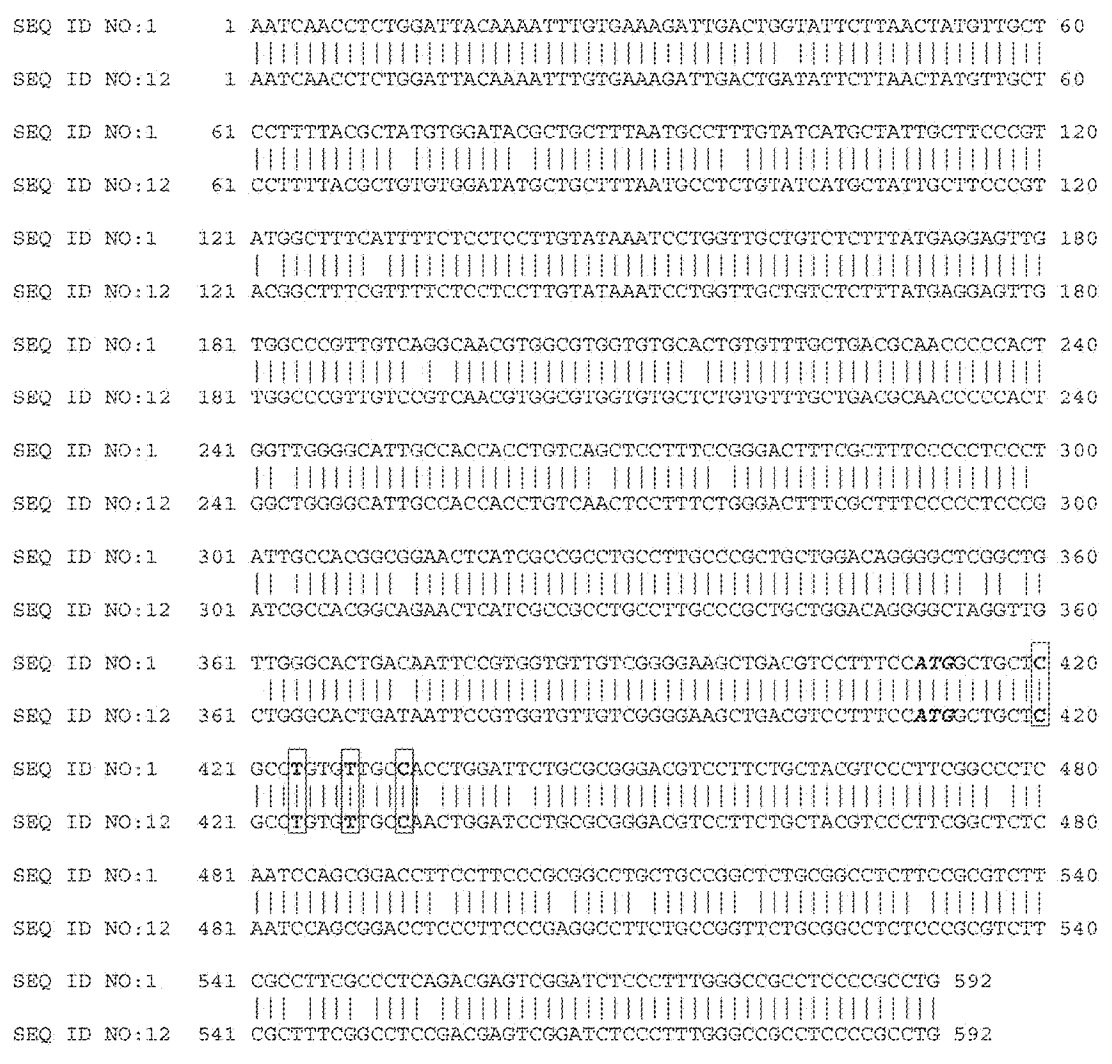
Figure 2B:
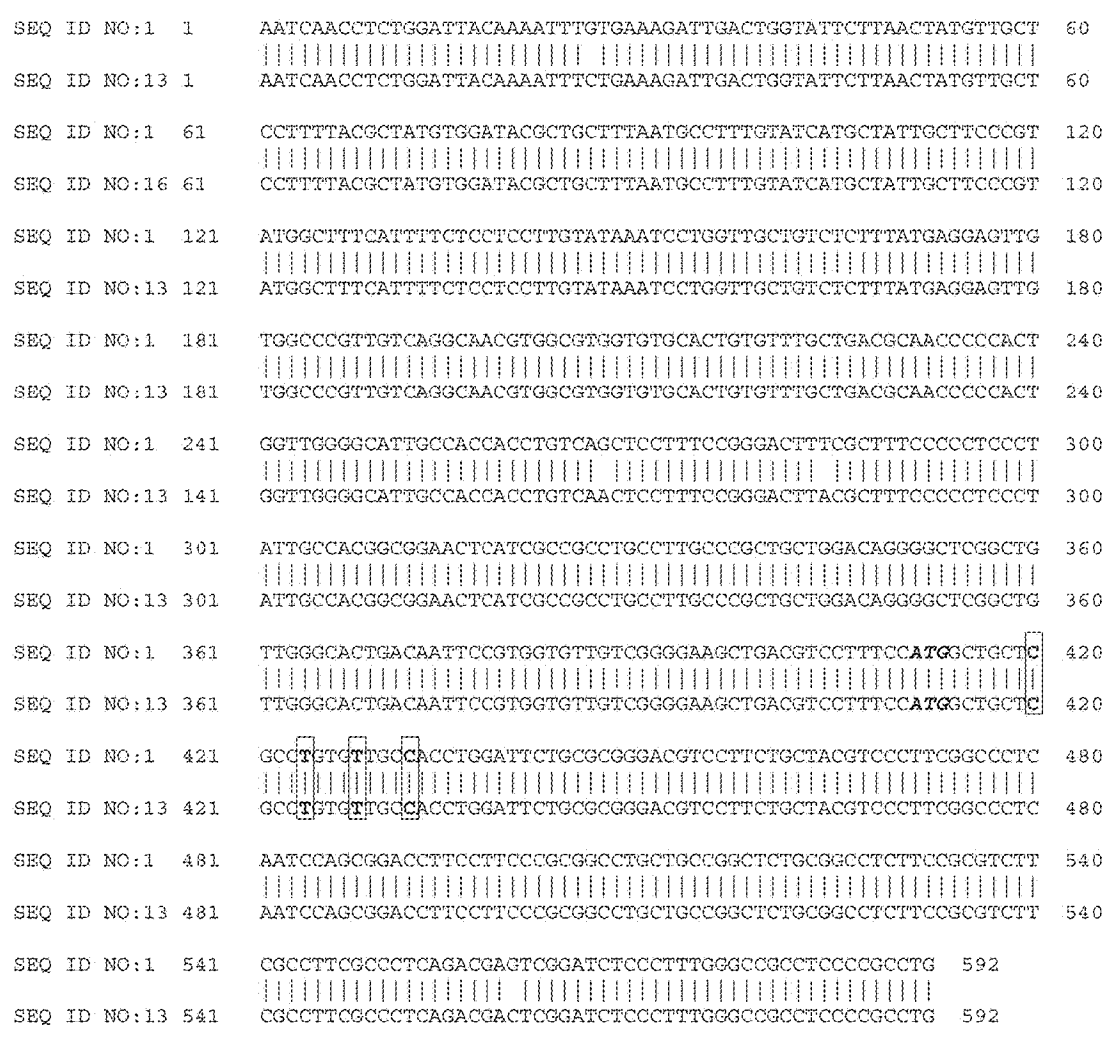
Figure 2D:
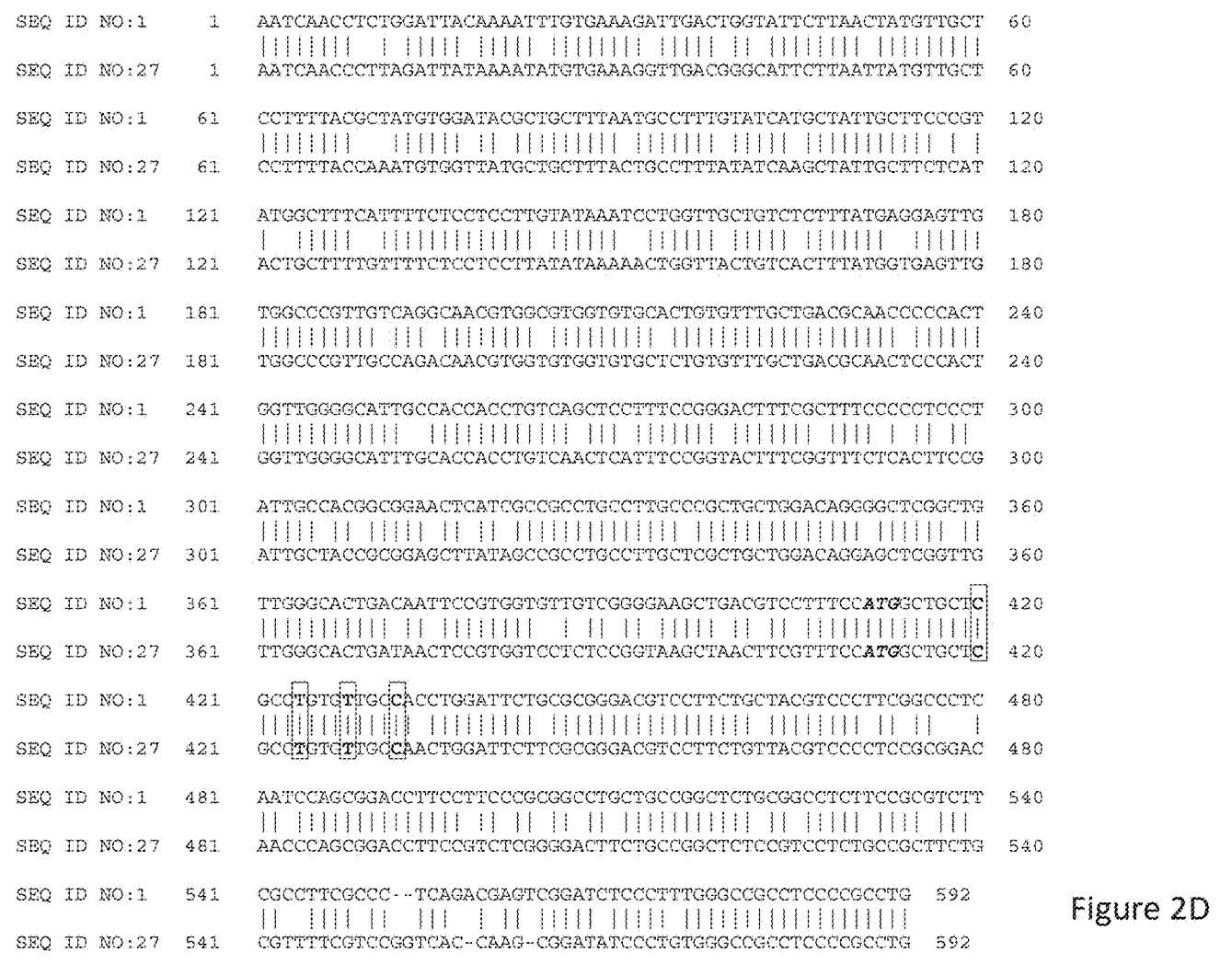

FIGS. 2A-2E depict exemplary alignments of the WPRE sequence set forth in SEQ ID NO:1 with other exemplary hepatitis PREs, and identifies corresponding residues. The symbol "I" between two aligned nucleotides indicates that the aligned nucleotides are identical. The absence of a "I" between two aligned nucleotides indicates that the aligned nucleotides are not identical. The symbol "-" indicates a gap in the alignment. Exemplary, non-limiting positions corresponding to an X gene start codon are indicated with bold and italicized text. Exemplary, non-limiting positions within an X gene corresponding to positions into which a stop codon may be introduced are boxed. Such positions correspond to an exemplary beginning residue (e.g. 3' position of a stop codon) for positioning of an introduced stop codon. For example, FIG. 2A depicts the alignment of the exemplary WPRE sequence set forth in SEQ ID NO:1 with the nucleic acids corresponding to the exemplary WPRE sequence set forth in SEQ ID NO:12. FIG. 2B depicts the alignment of the exemplary WPRE sequence set forth in SEQ ID NO:1 with the nucleic acids corresponding to the exemplary WPRE sequence set forth in SEQ ID NO:13. FIG. 2C depicts the alignment of the exemplary WPRE sequence set forth in SEQ ID NO:1 with the nucleic acids corresponding to the exemplary modified WPRE sequence set forth in SEQ ID NO:119. FIG. 2D depicts the alignment of the exemplary WPRE sequence set forth in SEQ ID NO:1 with the nucleic acids corresponding to an exemplary Ground Squirrel Hepatitis B virus PRE sequence set forth in SEQ ID NO:27. FIG. 2E depicts the alignment of the exemplary WPRE sequence set forth in SEQ ID NO:1 with the nucleic acids corresponding to an exemplary Human hepatitis B virus (HBV) PRE sequence set forth in SEQ ID NO:21.

DETAILED DESCRIPTION

Figure 1:
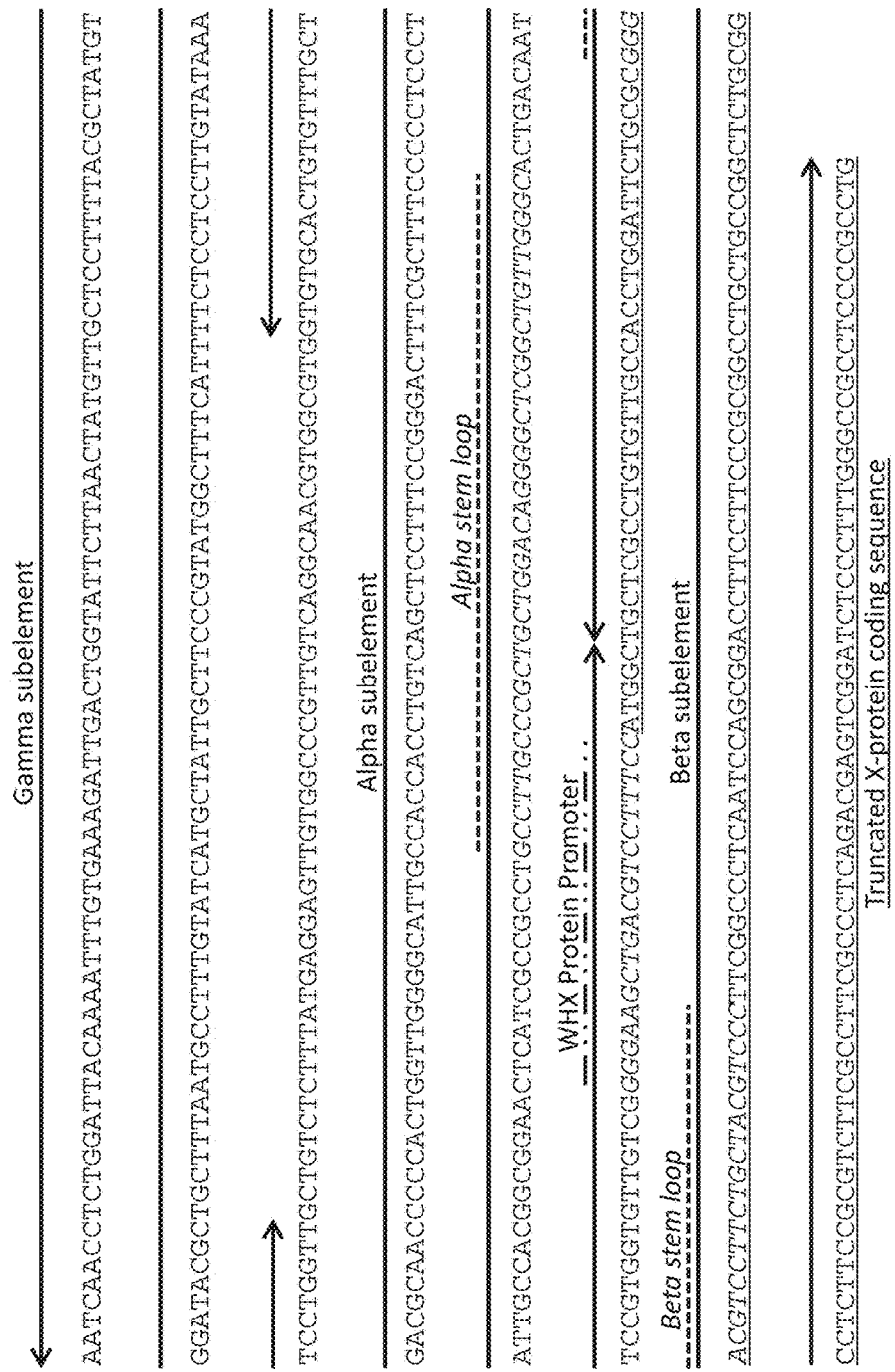
FIG. 1 depicts the nucleic acid sequence of an exemplary WPRE set forth in SEQ ID NO:1. Nucleic acids corresponding to reported PRE subelements (Donello et al. (1998) *J. Virol.*, 72:5085; Smith et al. (1998) *Nucleic Acids Research*, 26:4818) are indicated as follows: a gamma subelement, alpha subelement, and beta subelement are indicated by solid lines with arrows indicating the beginning and end positions; nucleotides corresponding to an exemplary stem loop-forming portions of the alpha and beta subelements, respectively, are indicated with a dashed line and italics; nucleotides corresponding to a WHX protein promoter are indicated with a dashed and dotted line and by italics; and nucleotides corresponding to the truncated X gene contained within this exemplary WPRE are underlined. It is understood that the description of elements thereof are theoretically or empirically derived. Thus, the exact locus can vary (e.g. longer of shorter), and a corresponding element is not necessarily the same for each PRE, such as for each species or subspecies of PRE.

I. Polynucleotides and Viral Vectors Containing Modified Post-Transcriptional Regulatory Element (PRE)

Provided are polynucleotides useful in enhancing the expression of recombinant molecules, such as recombinant proteins. The polynucleotides contain modified post-transcriptional regulatory elements (modified PREs), such as cis-acting post-transcriptional regulatory elements, including modified versions of viral post-transcriptional regulatory elements, such as modified versions of PREs derived from hepatitis viruses, such as the woodchuck hepatitis virus (WHV) and hepatitis B virus (HBV).

In some embodiments, the modified PREs include modified versions of wild-type WHV post-transcriptional regulatory elements (WPREs) or modified versions of HBV post-transcriptional regulatory elements (HBVPRE), including those with modifications reducing the risk that protein(s) or polypeptide(s), particularly those having oncogenic or immunogenic potential to host subjects, will be expressed from coding sequence within the PRE and/or that, if produced, such proteins will be retained. In general, the sequence of wildtype PREs contain an open-reading frame (ORF) encoding a partial X gene encoding a truncated X protein, which, in some cases, may be involved in tumorigenesis when expressed. Also, since PREs are generally used to enhance transgene expression from an expression vector, delivery of a vector containing a PRE may also result in exogenous expression of the truncated X protein that may contribute to immunogenicity when administered to a subject.

The provided modified PREs include a variant X-gene, the variant X-gene including one or more nucleotide modifications compared to an unmodified or wild-type hepatitis virus X gene. Such modifications generally reduce the potential for oncogenesis and/or immunogenicity upon introduction into a subject of a polynucleotide (e.g. viral vector) containing such modified PRE operably linked to nucleic acid encoding a recombinant molecule for expression of the recombinant molecule, for example, by preventing expression of certain proteins encoded by the PRE. For example, the modification(s) generally include those designed to prevent or reduce the likelihood of expression of polypeptides from the variant X gene of the modified PRE. The modifications are such that the modified PRE retains at least some post-transcriptional regulatory activity, such as all or a portion of the post-transcriptional regulatory activity of a corresponding wild-type PRE. In some embodiments, at least or at least about 25%, 30%, 40%, 50%, 60%, 70%, 80%, 90% or more of the post-transcriptional regulatory activity is retained.

Whereas viral vectors can provide an efficient system for the introduction of genetic material into cells, the use of certain viral vectors may not always produce the desired expression levels of such genetic material. Insertion of introns is used to enhance expression in some contexts, but may not always be appropriate in certain viral vectors. Hepatitis post-transcriptional regulatory elements (HPREs), such as woodchuck hepatitis virus post-transcriptional regulatory element (WPRE), have been employed to enhance gene expression.

Hepatitis virus-derived PREs, including WPREs and HBVPREs, generally promote, e.g., enhance, the expression of transgenes operably linked thereto, by facilitating post-transcriptional RNA export from the nucleus. Secondary and tertiary structures formed by cis-acting sequences or elements contained within the PREs can promote such functions. For example, wild-type hepatitis virus-derived PREs generally include an alpha subelement and beta subelement, which each independently form stem loop structures, that affect and/or are involved in full PRE post-transcriptional activity (Smith et al. (1998) Nucleic Acids Research, 26:4818-4827). Some wild-type non-human hepatitis virus PREs, such as WPRE, also includes a gamma subelement that can further enhance post-transcriptional activity. Such subelements may have or encode RNAs having structures that promote RNA export from the nucleus, for example, via interaction with CRM1-dependent and/or independent export machinery, provide binding sites for cellular proteins, increase the total amount of RNA, e.g. recombinant and/or heterologous RNA, transcripts, increase RNA stability, increase the number of poly-adenylated transcripts and/or augment the size of the poly-adenylated tails in such transcripts.

In addition to providing expression-enhancing function via these cis-acting sequences, wild-type and unmodified hepatitis-virus PREs, including mammalian hepatitis virus-derived PREs, such as HBVPRE or WPRE, contain a portion of a viral X gene, including at least a partial open reading frame encoding at least a truncated X protein. This region generally overlaps at least in part with the cis-acting regulatory subelements. X-proteins, however—even certain truncated X-proteins—can exhibit oncogenic potential when included in vectors for gene expression in subjects. Mutations made in the X-gene region of PREs, e.g., at the start site and/or promoter region, are not necessarily entirely satisfactory in addressing these concerns. For example, even a mutant promoter with diminished activity may permit some degree of expression of the X protein of the PRE or other polypeptide encoded by the region. Reversion or further mutation at one or more positions in the X gene could restore or increase expression levels of the X protein, promoting oncogenicity. Even aside from oncogenic potential, the risk of expression of any polypeptide, particularly of at least a certain length (e.g., at least 8, 9, 10, 11, or 12 amino acids in length or more), from the X protein or other reading frame within this region or operably linked with the promoter, may promote immunogenicity when administered to a subject. Provided are nucleic acids with modified PREs addressing these problems.

Typically, the X region of a PRE includes a partial reading frame that encodes a truncated X protein that is less than the full length hepatitis X protein, for example, that is less than 141 amino acids in length, such as less than 130 nucleotides, less than 120 nucleotides, less than 110 nucleotides, less than 100 nucleotides, less than 90 nucleotides, less than 80 nucleotides, less than 70 nucleotides, and generally less than 60, 50, 40, 30, 20, 10 or less nucleotides in length. As exemplified in the exemplary wild-type WPRE shown in FIG. 1, the X promoter and partial reading frame overlap with the alpha and beta cis-acting sequences. Translation of such a partial open reading frame can result in an encoded truncated X protein, which may have the potential to promote tumorigenesis and/or an immunogenic reaction upon introduction into a subject.

For example, with reference to the exemplary WPRE set forth in SEQ ID NO:1 (corresponding to nucleotides 1093-1684 of SEQ ID NO:2 or GenBank Acc. No. J04514.1), nucleotides 411-592 correspond to a partial X protein open reading frame under the operable control of an X promoter set forth as nucleotides 391-410. Translation from transcripts initiated from the X promoter encodes a truncated X protein. While generally not fully represented in a PRE, a corresponding exemplary full length X protein open reading frame is 425 base pairs and corresponds to nucleotides 1503-1928 of the exemplary hepatitis virus sequence set forth in SEQ ID NO:2 under the operable control of the X promoter corresponding to nucleotides 1483-1502. Other wild-type or unmodified mammalian hepatitis virus PREs can also contain a partial X protein open reading frame. Exemplary unmodified or wild-type mammalian hepatitis virus PREs, and the corresponding partial X protein open reading frame, are set forth in Table 1. Residues in any PRE, such as any mammalian PRE, that correspond to residues in the exemplary WPRE set forth in SEQ ID NO:1 or SEQ ID NO:125 (which contains nucleotides 1-589 of SEQ ID NO:1), can be identified by alignment of the full-length sequence of the PRE of each as exemplified in FIG. 2A-2E for exemplary sequences. Non-limiting examples of corresponding residues that can be identified include, for example, residues of any cis-acting element or portion thereof (e.g. alpha, beta or gamma or portion thereof), residues of X protein open reading frame, residues of a start codon, residues for introduction of a stop codon.

TABLE 1

Exemplary Mammalian Hepatitis Virus PRE

| PRE | SEQ ID NO | REFERENCE (PRE nucleotides) | X region in SEQ ID NO X gene promoter | ORF |
|---|---|---|---|---|
| WPRE (WHV8) | 1 | GenBank No. J04514.1 (1093-1684) | 391-410 | 411-592 |
| WPRE | 125 | GenBank No. J04514.1 (1093-1681) | 391-410 | 411-589 |
| WPRE | 12 | GenBank No. J02442.1 (1093-1684) | 391-410 | 411-592 |
| WPRE (WHV2) | 13 | GenBank No. M11082.1 (1093-1684) | 391-410 | 411-592 |
| WPRE (WHV7) | 14 | GenBank No. M18752.1 (1093-1684) | 391-410 | 411-592 |
| WPRE (WHV59) | 15 | GenBank No. M19183.1 (1093-1684) | 391-410 | 411-592 |
| WPRE (WHV34) | 16 | GenBank No. KF874491.1 (1093-1684) | 391-410 | 411-592 |
| WPRE | 17 | GenBank No. AY628100.1 (1093-1684) | 391-410 | 411-592 |
| WPRE | 18 | GenBank No. AY628099.1 (1093-1684) | 391-410 | 411-592 |
| WPRE | 19 | GenBank No. KF874493.1 (1093-1684) | 391-410 | 411-592 |
| WPRE | 20 | GenBank No. GU734791.1 (1093-1684) | 391-410 | 411-592 |
| HBVPRE | 21 | GenBank No. D00329.1 (963-1684) | | 412-722 |
| HBVPRE | 22 | GenBank No. AF100309.1 (965-1686) | | 412-722 |
| Orangutan hepatitis b virus | 23 | GenBank No. AF193863.1 (963-1684) | | 412-722 |
| Chimpanzee hepatitis b virus | 24 | GenBank No. D00220.2 (964-1684) | | 411-721 |
| Gorilla hepatitis b virus | 25 | GenBank No. AJ131567.1 (2333-3053) | | 411-721 |
| artic ground squirrel hepatitis b virus | 26 | GenBank No. U29144.1 (2475-3056) | | 401-582 |
| ground squirrel hepatitis b virus | 27 | GenBank No. NC_001484.1 (2474-3065) | | 411-592 |
| promoter/start codon mutant WPRE | 119 | nucleotides 2058-2649 of "Cloning vector pLV.MCS.WHVPRE, complete sequence" (GenBank: JN622008.1; GI:373501904); nucleotides 5700-6291 of SEQ ID NO: 5 from U.S. Pat. No. 7,384,738 | 391-410 | 411-592 |
| Promotor/start codon mutant WPRE | 120 | U.S. Pat. No. 7,419,829 | 391-410 | 411-592 |

In embodiments of the provided modified PREs, the variant X gene contained therein are variants of an unmodified or wild-type X gene. The unmodified X gene can be any that includes a partial X gene reading frame, such as an X gene open reading frame present in an unmodified or wild-type PRE. For example, the variants of the X gene of the modified PRE include portions of mammalian hepatitis virus X genes, which can contain a partial X protein open reading frame and encode a truncated X protein, typically further modified to include one or more stop codon or other modification to reduce the risk of oncogenicity and/or immunogenicity. For example, the variant X genes include variants of a portion of the wild-type X gene. In some embodiments, the variant X gene may contain at least 180 nucleotides in length but fewer nucleotides than contained in a full-length hepatitis virus X gene, e.g., fewer than 425 nucleotides in length. Generally, the modified PRE in which is contained the variant X gene contains a sufficient portion of the cis-regulating sequences (e.g. one or more of an alpha, beta and/or gamma subelements, portion(s) thereof and/or functional variant(s) thereof) to regulate post-transcriptional activity of an RNA transcript.

The nucleotide modifications in a variant X gene of a modified PRE can include nucleotide deletions, insertions, and/or substitutions. Such modifications can include nucleotide changes in a region of the PRE encoding the viral X protein or portion thereof that include, but are not limited to, nucleotide changes resulting in a stop codon, a sequence that targets a protein for degradation, and combinations thereof. The modifications typically are such that the modified PRE retains at least some post-transcriptional regulatory activity, such as all or a portion of the post-transcriptional regulatory activity of a corresponding wild-type PRE or an unmodified PRE (e.g. SEQ ID NO:1 or SEQ ID NO:125), or another modified PRE known in the art to have a sufficient degree of activity for use in viral vector transduction, such as the PRE having the sequence set forth in SEQ ID NO: 119 or SEQ ID NO:120. In some embodiments, the modified PREs are provided in an expression vector (e.g. viral vector) operably linked to nucleic acid encoding a recombinant protein, such as a heterologous protein. By heterologous in this context refers to a protein that is not normally expressed from a virus and/or not encoded by a viral genome. In some embodiments, the heterologous protein is not expressed by the hepatitis virus from which the PRE is derived. In any of such embodiments, the provided modified PREs may enhance expression of nucleic acid encoding a recombinant protein, for example, compared to expression of the recombinant protein from an expression vector not containing a PRE.

In some embodiments, the provided modified PREs exhibit post-transcriptional activity, for example to enhance expression of an operably linked nucleic acid, while avoiding or reducing the likelihood of oncogenesis upon introduction and/or expression in a subject. For example, unwanted expression of functional full-length or truncated X proteins encoded by PREs can promote oncogenesis. In some embodiments, the modified PREs contain a variant X gene that includes modifications that prevent or reduce the likelihood of expression of an unwanted protein, such as a viral X protein or functional portion thereof, thereby reducing the risk of oncogenesis. For example, such modifications can include nucleotide changes that introduce one or more stop codons in the variant X gene, such as stop codon(s) not present in the unmodified or wild-type X gene, so that an unwanted protein, such as an X protein or functional portion thereof sufficient to cause oncogenesis, and/or any peptide with oncogenic potential, is not expressed. In other examples, such modifications include nucleotide changes that introduce a post-translational modification signal, such as a ubiquitination site, in the variant X gene not present in the unmodified or wild-type X gene, such that the encoded X protein is targeted for degradation.

In some embodiments, the provided modified PREs further include modification(s) (e.g. a nucleotide insertion, substitution or replacement or deletion) in the X gene promoter and/or start codon as compared to an unmodified or wild-type PRE. In some embodiments, the provided modified PRE does not include a modification in the X gene promoter. In some embodiments, the provided modified PRE does not include a modification in the X gene start codon. In some embodiments, the provided modified PRE does not include modifications in the X gene promoter and the X gene start codon. In other embodiments, the X gene promoter and/or start codon is wild-type.

In some embodiments, more than one modification affecting expression of the X protein encoded by the variant X gene in the modified PRE is present. For example, in some embodiments, the modified PRE contains a variant X gene that contains a plurality of stop codons not present in the corresponding unmodified or wild-type PRE, such as at least 2, 3, 4, 5, 6 or more stop codons. Due to the presence of multiple nucleotide changes, such as to effect introduction of a plurality of stop codons, the provided modified PREs can reduce the likelihood of X protein expression resulting from reversion to the unmodified sequence, such as a wild-type sequence. In some embodiments, a plurality of stop codons can include a stop codon in each reading frame of the variant X gene, and/or multiple stop codons in a single reading frame, thereby reducing the likelihood of unwanted protein expression. In some embodiments, at least 3 stop codons are included, e.g., to cover all three reading frames, which, in some embodiments, can be sequential.

The provided modified PREs contain features that can reduce the risk of oncogenicity due to reversion to wild-type sequence of the X-gene present in the PRE or start site or promoter thereof and/or the expression of other oncogenic polypeptides due to other mutations. Such features can provide advantages over available modified post-transcriptional regulatory sequences, such as those containing modifications only in the X protein promoter and/or start codon (See U.S. Pat. No. 7,419,829). For example, even mutated promoters may not necessarily result in a complete absence of protein expression from the promoter. By incorporating multiple modifications to produce multiple stop codons in the variant X gene, the provided modified PREs in some embodiments prevent or reduce the likelihood of oncogenic or immunogenic peptides, even in the context of such leaky promoters.

In some embodiments, the provided modified PREs containing a variant X gene can reduce the likelihood of X protein immunogenicity upon introduction into a subject. For example, to reduce the chance of creating an immunogenic epitope from an expressed variant X protein, the one or a plurality of stop codons can begin close enough to the start codon of the X protein open reading frame to prevent expression of a polypeptide containing an epitope that could induce an unwanted immune response. In some embodiments, such features ensure or increase the likelihood that, upon introduction into a subject, the variant X gene in the modified PRE does not result in the expression of any polypeptide having a potentially immunogenic epitope. In some embodiments, the polynucleotide containing a modified PRE includes at least one stop codon, e.g. the first stop codon or each of a plurality of introduced stop codons present in the variant X gene of the modified PRE, beginning at a position within at least 18 or 21 or 24 or 27 or 30 or 33 or 36 nucleotides of a start codon of the variant X gene (e.g., of the first position of such a start codon) or of a codon corresponding to a start codon in the corresponding wild-type or unmodified sequence. In some examples of such embodiments, such features ensure that no polypeptide longer than 6 or 7 or 8 or 9 or 10 or 11 or 12 amino acids in length encoded by the PRE is produced, e.g., even in the case of a wild-type or unmodified start codon or promoter or reversion thereto or other mutation resulting in a functional start codon and/or promoter. In some embodiments, the polynucleotide containing a modified PRE includes a stop codon, e.g., the first stop codon or each of a plurality of stop codons present in the variant X gene of the modified PRE, beginning at a position within at least 9, 12 or 15 nucleotides of a start codon of the variant X gene (e.g., of the first position of such a start codon) or of a codon corresponding to a start codon in the corresponding wild-type or unmodified sequence.

The provided polynucleotides include those with modified PREs designed to promote safety advantages, e.g., reduction in oncogenesis and/or immunogenicity, while maintaining a sufficient degree of post-transcriptional activity, such as expression-enhancing function. Hence, the modified PREs of the provided polynucleotides generally also are designed to retain a sufficient amount of the post-transcriptional activity, such as expression-enhancing function, of the corresponding unmodified or wild-type PRE. As describe above, the region of a hepatitis virus, such as WHV, that encodes the X-protein generally overlaps with structural features of a PRE of such virus that are important for its expression-enhancing function. In some embodiments, the sites and/or nature of modifications in the modified PREs, such as those that introduce the stop codon(s) and/or post-translational signal-encoding sequence(s) as described are designed to minimize alterations to certain secondary or tertiary structure encoded by the PRE. In some embodiments, such modifications are introduced in regions of the PRE other than those encoding a stem-loop structure of a PRE subelement, such as a stem-loop structure of an alpha and/or beta subelement of a PRE. In some embodiments, no stop codon is introduced or modification is made within a minimal alpha subelement encoding the alpha stem-loop structure or within a portion of the beta subelement encoding the beta stem-loop structure. In some embodiments, if a modification is introduced into a stem-loop structure, the modifications are made by selecting nucleobases that are different from the corresponding wild-type or unmodified nucleobases and yet maintain the secondary or tertiary structure(s) of the PRE. For example, in some embodiments, where a modification to a certain position within a stem-loop forming structure is modified, e.g., to introduce a stop codon, a complementary modification may be made at another position to permit the formation of a secondary or tertiary structure similar to or the same as that in the wild-type or unmodified sequence, e.g., a stem-loop structure.

Also among the provided polynucleotides are polynucleotides containing a variant Flap sequence ("variant Flap" polynucleotides). The variant Flap polynucleotides include polynucleotides, such as those containing one or more viral nucleic acid, in which one or more Flap sequence or portion thereof has been deleted. Such variant Flap polynucleotides include expression cassettes and vectors, such as viral vectors, for the expression of recombinant molecules, such as recombinant, e.g., heterologous proteins. In some embodiments, the polynucleotides comprising the modified PREs further comprise variations in Flap sequences and/or are variant Flap polynucleotides. In general, the variation(s) in the Flap are such that they still permit and/or do not substantially disrupt viral delivery or expression of the recombinant molecule, e.g., in a host cell.

Also provided are expression cassettes containing the polynucleotides, generally further including a promoter operably linked to the sequence encoding the recombinant protein, such as heterologous protein, and vectors containing such polynucleotides and expression cassettes, including retroviral vectors such as lentiviral and gamma-retroviral vectors. Also provided are viruses and cells containing such polynucleotides, cassettes, and/or vectors, including packaging cells and host cells, such as T cells and compositions containing the same. Also provided are methods and uses of such embodiments, including therapeutic methods and uses, such as those involving the administration of the virus, vector, and/or cells to a subject in an amount effective to treat or prevent a disease or condition.

A. Modified PREs

The modified PREs in the provided polynucleotides contain variant X genes. The variant X genes are variants of unmodified, typically wild-type, hepatitis X genes. The variant X genes include one and typically more than one modification as compared to the wild-type or other unmodified X gene. In particular, the variant X gene generally includes one or more modifications designed to prevent or reduce the likelihood that an unwanted protein or peptide encoded by a sequence within the X gene and/or PRE will be expressed and/or maintained, e.g., upon introduction into a subject. The modifications may include nucleotide deletion(s), substitutions, and/or insertions as compared to the unmodified, e.g., wild-type sequence.

In some embodiments, the modifications include mutations that result in the presence of a stop codon in the variant X gene of the modified PRE not present in the corresponding wild-type or otherwise unmodified X gene, such as not present in the corresponding wild-type or otherwise unmodified PRE containing a partial X gene. In some embodiments, such modifications shorten the X protein-coding open reading frame as compared to a wild-type X gene or X gene fragment within a wild-type or unmodified PRE. In some embodiments, the modifications result in a modified PRE in which the variant X gene contains an X protein open reading frame that is no longer than 9, 12, 15, 18, or 21 nucleotides in length. In some embodiments, the modifications in the variant X gene of the modified PRE prevent the expression of any protein from the X protein reading frame contained therein that is longer than 3, 4, 5, 6, or 7 amino acids in length or that may be immunogenic to a subject or have oncogenic potential or activity. In some embodiments, if the variant X gene also contains a mutated or modified start site or promoter, the stop codon modifications prevent such expression even in the event of a mutation that results in reversion to a functional promoter or start site.

In some embodiments, the modifications in the variant X gene of the modified PRE prevent the expression of any unwanted polypeptides, whether in the X protein-coding reading frame or not. For example, in some embodiments, the modifications in the variant X gene of the modified PRE prevent the expression of any peptide(s) or peptide(s) from the X gene contained therein that are longer than a certain length, such as longer than 3, 4, 5, 6, or 7 amino acids in length and/or that may be immunogenic upon expression in a subject.

In some embodiments, the modifications include those which introduce coding sequences to introduce or result in post-translation degradation amino acid sequences that target expressed protein(s) encoded by the variant X gene or portion thereof of the modified PRE for degradation. Exemplary degradation sequences include ubiquitination signals. Thus, the modifications in the variant X gene of the modified PRE may further include those resulting in a post-translational degradation sequence, such as a ubiquitination sequence, not present in the corresponding protein encoded by an unmodified or wild-type X gene, such as not present in the corresponding wild-type or unmodified PRE containing a partial X gene.

The variant X gene of the modified PRE generally contains a portion of an X gene that includes fewer nucleobases in length than a corresponding wild-type full-length X gene present in a corresponding wild-type hepatitis virus. In some embodiment, the portion of the X gene lacks X gene nucleotides that do not overlap with and/or that are not important or essential for post-transcriptional regulatory function(s) of the PRE. In some embodiments, the portion of the X gene lacks X gene residues of a wild-type hepatitis virus not within the alpha, beta, and/or gamma subelement(s) of the PRE and/or functional regions thereof. Thus, the modified PREs herein generally do not include full-length X genes or full-length variants thereof. In some such embodiments, the variant X gene within the modified PRE generally includes fewer than at or about 425, 400, 300, 200, or 180 nucleobases in length.

The modified PRE generally contains one or more of an alpha, beta and/or gamma subelement, which, in some cases, can be a variant of such a subelement of a wild-type or unmodified PRE or a functional portion thereof, e.g., one that is sufficient for post-transcriptional activity and/or formation of a stem-loop or other secondary or tertiary structure. In some cases, at least some of such portion(s) generally overlap with the variant X gene portion of the modified PRE. Thus, in some cases, a portion of the variant X gene may be contained within a portion of the alpha subelement and/or a portion of the variant X gene may be contained within or overlaps with the beta subelement. In some embodiments, the modifications in the variant X gene of the provided modified PREs as compared to a wild-type or unmodified X gene or PRE do not ablate, reduce and/or interfere with the post-transcriptional activity to control expression of an operably linked nucleic acid (e.g. recombinant molecule or transgene) mediated by the alpha and/or beta and/or gamma subelement(s) of the modified PRE, and/or do not do so substantially, as compared to the post-transcriptional activity mediated by the subelement(s) of a corresponding wild-type or unmodified PRE not having the modification(s) or compared to another modified PRE known to retain sufficient activity, such as that having the sequence of SEQ ID NO: 119, 120 or 216.

In one embodiment, the nucleotide changes that introduce stop codons and/or post-translation degradation sequence are such that, on the RNA level, they do not alter the secondary and/or tertiary structure of the cis-element sequences within the PRE and/or they retain a substantial degree of the secondary and/or tertiary structure of the cis-element sequences within the PRE, as compared to a corresponding wild-type or unmodified PRE and/or PRE not containing such modifications. In another embodiment, the nucleotide changes that introduce stop codons and/or a post-translation degradation sequence, are such that, on the RNA level, the nucleotide changes do not alter the activity of the PRE, e.g., its ability to promote RNA export from the nucleus, for example, via interaction with CRM1-dependent and/or independent export machinery, provide binding sites for cellular proteins, increase the total amount of RNA, e.g. transgene RNA, transcripts, increase RNA stability, increase the number of poly-adenylated transcripts and/or augment the size of the poly-adenylated tails in such transcripts, as compared with a corresponding wild-type PRE and/or PRE not containing such modifications, and/or compared to another modified PRE known in the art to have a sufficient degree of activity for use in viral vector transduction or accepted for use therein and/or accepted for such uses in the context of gene therapy. In some embodiments, the another unmodified PRE has the sequence set forth in SEQ ID NO: 119, SEQ ID NO: 120 or SEQ ID NO:216.

In some embodiments, a beta subelement within the modified PRE includes at least a portion of the variant X gene. In some such embodiments, the beta subelement is a functional variant or portion thereof of a beta subelement of a wild-type or unmodified PRE, such that the modified PRE containing the functional variant or portion of the beta subelement exhibits post-transcriptional activity. In some embodiments, the functional variant of the beta subelement is a variant of a beta subelement set forth in SEQ ID NO:6 or a functional portion thereof. In some embodiments, a functional variant or portion of a beta sub-element contains nucleotide residues sufficient to form a beta stem-loop. For example, in some embodiments, a functional variant or portion of a beta sub-element contains nucleotide residues corresponding to nucleotide residues 448-470 of SEQ ID NO:1 or SEQ ID NO:125, such as the sequence of nucleotides set forth in SEQ ID NO:7. In aspects of the modified PRE provided herein, the variant X gene does not contain a nucleotide change within any nucleotides corresponding to nucleotides 448-470 of SEQ ID NO:1 or SEQ ID NO:125 and/or in a region of nucleotides corresponding to nucleotides set forth in SEQ ID NO:7. In some embodiments, where a modification, e.g., to introduce a stop codon, is at a nucleotide base corresponding to one or more nucleotides 448-470 of SEQ ID NO:1 or SEQ ID NO:125 and/or one or more nucleotides corresponding to nucleotides set forth in SEQ ID NO:7, a complementary modification may be made at another position to permit the formation of a secondary or tertiary structure similar to or the same as a beta-stem loop of the wild-type or unmodified sequence.

In some embodiments of a modified PRE containing an alpha subelement, the modified alpha subelement can be from an unmodified hepatitis PRE, such as a wild-type hepatitis PRE, or can be a functional variant thereof such that the modified PRE containing the functional variant of the alpha subelement exhibits post-transcriptional activity. In some embodiments, the alpha subelement is set forth in SEQ ID NO:3 or is set forth in SEQ ID NO:4, or is a functional variant or portion of SEQ ID NO:3 or SEQ ID NO:4. In some embodiments, a functional variant or portion of an alpha sub-element contains nucleotide residues sufficient to form an alpha stem-loop. For example, in some embodiments, a functional variant of an alpha sub-element contains nucleotide residues corresponding to nucleotide residues 329-366 of SEQ ID NO:1 or SEQ ID NO:125, such as the sequence of nucleotides set forth in SEQ ID NO:5. In aspects of the modified PRE provided herein, the modified PRE does not contain a nucleotide change within any nucleotides corresponding to nucleotides 329-366 of SEQ ID NO:1 or SEQ ID NO:125 and/or in a region of nucleotides corresponding to nucleotides set forth in SEQ ID NO:5. In some embodiments, where a modification is at a nucleotide base corresponding to one or more nucleotides 329-366 of SEQ ID NO:1 or SEQ ID NO:125 and/or one or more nucleotides corresponding to nucleotides set forth in SEQ ID NO:5, a complementary modification may be made at another position to permit the formation of a secondary or tertiary structure similar to or the same as an alpha-stem loop of the wild-type or unmodified sequence.

In one embodiment, the modified PRE at least contains an alpha and beta subelement, such as a functional variant of an alpha and beta subelement, at least some portion of which generally overlaps with the variant X gene. In some embodiments, the modified PRE contains a gamma subelement or functional variant thereof. In embodiments of a modified PRE containing a gamma subelement, the modified gamma subelement can be from an unmodified hepatitis PRE, such as a wild-type hepatitis PRE, or can be a functional variant thereof such that the modified PRE containing the functional variant of the gamma subelement retains post-transcriptional activity. In some embodiments, the gamma subelement is set forth in SEQ ID NO:8, or is a functional variant or portion of SEQ ID NO:8.

The nucleotide modifications, such as those within the variant X gene, of a modified PRE can include nucleotide deletions, insertions, and/or substitutions. The variant X gene can contain at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 nucleotide changes compared to the X gene of the unmodified PRE, such as a wild-type PRE. In some embodiments, the variant X gene contains no more than 4, 5, 6, 7, 8, 9, 10, 11 or 12 nucleotide changes. In some embodiments, the variant X gene has a sequence of nucleotides that exhibits at least 65%, 70%, 75%, 80%, 85%, 90%, 91%, 92%, 93%, 94%, 95%, 96%, 97%, 98% or 99% sequence identity to the X gene set forth in SEQ ID NO: 10, to the sequence of nucleotides 391-592 of any of SEQ ID NOS:1, 12-20, 119 or 120 or to the sequence of nucleotides 391-589 of SEQ ID NO:125 or 216, in which the variant X gene contains at least one stop codon not present therein and/or a sequence encoding a post-translational modification signal or degradation sequence not present therein. For example, in some embodiments, the variant X gene has a sequence of nucleotides that exhibits at least 85%, 90%, 91%, 92%, 93%, 94%, 95%, 96%, 97%, 98% or 99% sequence identity to the X gene set forth in SEQ ID NO: 10, to the sequence of nucleotides 391-592 of SEQ ID NO:1 or to the sequence of nucleotides 391-589 of SEQ ID NO:125, in which the variant X gene contains at least one stop codon not present therein and/or a sequence encoding a post-translational modification signal or degradation sequence not present therein. In some embodiments, the modified PRE has a sequence of nucleotides that exhibits at least 65%, 70%, 75%, 80%, 85%, 86%, 87%, 88%, 89%, 90%, 91%, 92%, 93%, 94%, 95%, 96%, 97%, 98% or 99% sequence identity to the PRE set forth in any of SEQ ID NOS:1, 12-20, 119, 120, 125 or 216, in which the modified PRE contains at least one stop codon not present therein and/or a sequence encoding a post-translational modification signal or degradation sequence not present therein. For example, in some embodiments, the modified PRE has a sequence of nucleotides that exhibits at least 65%, 70%, 75%, 80%, 85%, 86%, 87%, 88%, 89%, 90%, 91%, 92%, 93%, 94%, 95%, 96%, 97%, 98% or 99% sequence identity to the PRE set forth in SEQ ID NO:1 or SEQ ID NO:125, in which the modified PRE contains at least one stop codon not present therein and/or a sequence encoding a post-translational modification signal or degradation sequence not present therein.

In some embodiments, the variant X gene is a partial X gene, such as a portion of a wild-type X genes, having a sequence that is less than the full length sequence of the X gene of an hepatitis virus, such as a wild-type hepatitis virus, such as a mammalian hepatitis virus. For example, in some embodiments, the modified PRE contains a variant X gene that is less than or no more than at or about 250 nucleotides in length, such as less than or no more than at or about 240 nucleotides, 230 nucleotides, 220 nucleotides, 210 nucleotides, 200 nucleotides, 190 nucleotides, 180 nucleotide, 170 nucleotides, 160 nucleotides, 150 nucleotides, 140 nucleotides, 130 nucleotides, 120 nucleotides, 110 nucleotides, 100 nucleotides, 90 nucleotides, 80 nucleotides or 70 nucleotides in length. In some embodiments, the modified PRE contains a variant X gene that is at least 60 nucleotides in length but is less than the full length sequence of the X gene of a hepatitis virus, such as a wild-type hepatitis virus, such as a mammalian hepatitis virus. For example, in some embodiments, the modified PRE contains a variant X gene that is at least 60 nucleotides in length but is less than or no more than at or about 250 nucleotides in length, such as less than or no more than at or about 240 nucleotides, 230 nucleotides, 220 nucleotides, 210 nucleotides, 200 nucleotides, 190 nucleotides, 180 nucleotide, 170 nucleotides, 160 nucleotides, 150 nucleotides, 140 nucleotides, 130 nucleotides, 120 nucleotides, 110 nucleotides, 100 nucleotides, 90 nucleotides, 80 nucleotides or 70 nucleotides in length. In some embodiments, the modified PRE contains a variant X gene that is at least or about at least 180 nucleotides in length.

In some embodiments, the modified PRE containing the variant X gene is a variant of an unmodified PRE, such as a wild-type hepatitis PRE, that contains an X gene or portion thereof. For example, the variant X gene can be a variant of a wild-type hepatitis PRE that has an X gene that is less than the full-length sequence of the corresponding X gene of the hepatitis virus, such as a wild-type hepatitis virus, such as a mammalian hepatitis virus. The unmodified or wild-type X gene can contain an X gene that is less than or no more than at or about 250 nucleotides in length, such as less than or no more than at or about 240 nucleotides, 230 nucleotides, 220 nucleotides, 210 nucleotides, 200 nucleotides, 190 nucleotides, 180 nucleotide, 170 nucleotides, 160 nucleotides, 150 nucleotides, 140 nucleotides, 130 nucleotides, 120 nucleotides, 110 nucleotides, 100 nucleotides, 90 nucleotides, 80 nucleotides or 70 nucleotides in length.

In some embodiments, the unmodified PRE, such as wild-type hepatitis PRE, is one that contains an X gene having an open reading frame encoding a functional X protein, e.g., a truncated X protein. In such an embodiment, the variant X gene contains a start codon for initiating translation of the X protein. In some embodiments, the start codon is an ATG start codon. In some embodiments, the variant X gene contains a start codon corresponding to a start codon beginning at a position corresponding to position 411 of SEQ ID NO:1 or SEQ ID NO:125. In some embodiments, the unmodified PRE, such as a wild-type PRE, can contain an open reading frame encoding an X protein that is at least 30 amino acids in length, such as at least 40 amino acids, 50 amino acids, 60 amino acids, 70 amino acids, or 80 amino acids.

The modified PRE generally contains a variant X gene that contains a modification, for example one or more nucleotide modifications that introduces one or more stop codon and/or post-translational degradation sequence not present in an unmodified hepatitis X gene, such as not present in a wild-type hepatitis X gene or corresponding truncated version thereof (e.g. as present in a PRE). In some embodiments, the variant X gene contains a modification not present in a wild-type mammalian hepatitis X gene or corresponding truncated version thereof (e.g. as present in a PRE). In some embodiments, the unmodified or wild-type hepatitis X gene or the truncated version thereof is an X gene that exhibits at least or about at least 65%, 70%, 75%, 80%, 85%, 90%, 95%, or more sequence identity to SEQ ID NO:9 or SEQ ID NO:10 or to nucleotides 411-592 of SEQ ID NO:1 or to nucleotides 411-589 of SEQ ID NO:125. In some embodiments, the wild-type or unmodified mammalian hepatitis X gene or corresponding truncated version thereof has the sequence of nucleotides corresponding to nucleotides 411-592 of any of SEQ ID NOS: 1 or 12-20, nucleotides 411-589 of SEQ ID NO:125, nucleotides 412-722 of any of SEQ ID NO:21-23, nucleotides 411-721 of SEQ ID NO:25, nucleotides 401-582 of SEQ ID NO:26 or nucleotides 411-592 of SEQ ID NO:27. In some embodiments, the unmodified or wild-type hepatitis X gene is a WHV X gene or corresponding truncated version thereof that exhibits at least or about at least 94%, 95%, 96%, 97%, 98% or 99% sequence identity to SEQ ID NO:9, nucleotides 411-592 of SEQ ID NO:1 or to nucleotides 411-589 of SEQ ID NO:125. In some embodiments, the unmodified or wild-type WHV X gene or corresponding truncated version thereof has the sequence of nucleotides corresponding to nucleotides 411-592 of any of SEQ ID NOS: 1, 12-20, 119 or 120 or to nucleotides 411-589 of SEQ ID NO:125 or 216. In some embodiments, the hepatitis X gene is a WHV X gene set forth in SEQ ID NO:9 or a corresponding truncated version thereof set forth in SEQ ID NO:10.

In some embodiments, the variant X gene of the modified PRE contains difference(s) compared to an X gene or portion thereof contained within an unmodified hepatitis PRE, such as a wild-type hepatitis PRE. In some embodiments, such a wild-type hepatitis PRE is a mammalian hepatitis PRE. In some embodiments, the wild-type or unmodified mammalian PRE has a sequence of nucleotides with at least or about at least 65%, 70%, 75%, 80%, 85%, 90%, 95%, or more sequence identity to SEQ ID NO:1 or SEQ ID NO:125. In some embodiments, the wild-type or unmodified mammalian hepatitis PRE has the sequence of nucleotides set forth in any of SEQ ID NOS: 1 or 12-27. In some embodiments, the unmodified or wild-type hepatitis PRE is a WPRE that exhibits at least or about at least 94%, 95%, 96%, 97%, 98% or 99% sequence identity to SEQ ID NO:1 or SEQ ID NO:125. For example, in some embodiments, the unmodified or wild-type WPRE has the sequence of nucleotides set forth in any of SEQ ID NOS: 1, 12-20, 119, 120, 125 or 216.

In some embodiments, the variant X gene is operably coupled to a promoter. In some embodiments, the promoter is an unmodified or wild-type X gene promoter. For example, the promoter can have the sequence of nucleotides set forth in SEQ ID NO: 11 or a functional variant or portion thereof. The promoter can have the sequence of nucleotides 7-20 of SEQ ID NO:11. In some embodiments, the promoter is a mutant or modified X gene promoter, such as described in subsection I.A.3 below.

In some embodiments, the modified PRE exhibits post-transcriptional activity to mediate, such as to enhance, the expression of a nucleic acid encoding a recombinant protein, such as a heterologous protein, operably linked thereto, e.g., as compared to expression of a nucleic acid that is not operably linked to the PRE and/or not linked to any cis-regulatory sequence. In some embodiments, the modified PRE exhibits activity to promote RNA export from the nucleus, provide binding sites for cellular proteins, increase the total amount of RNA transcripts, increase RNA stability, increase the number of poly-adenylated transcripts and/or augment the size of the poly-adenylated tails in such transcripts. In some embodiments, the modified PRE retains the activity or a substantial and/or sufficient degree of activity of the corresponding unmodified hepatitis PRE, such as wild-type hepatitis PRE, and/or of another modified PRE known in the art to have a sufficient degree of activity for use in viral vector transduction, such as the PRE having the sequence set forth in SEQ ID NO: 119, SEQ ID NO:120 or SEQ ID NO:216. In some embodiments, the modified PRE exhibits at least or about at least or about 60%, 65%, 70%, 75%, 80%, 85%, 90%, 95%, 100%, 110%, 120%, 130%, 140%, 150%, 160%, 170%, 180%, 190%, 200% or more of the post-transcriptional activity of an unmodified or wild-type PRE set forth in any of SEQ ID NOS: 1, 12-27, 119, 120, 125 or 216. In some embodiments, the modified PRE exhibits at least or about at least or about 80%, 85%, 90%, 95%, or 100% of the activity of the WPRE set forth in SEQ ID NO:1 or SEQ ID NO:125.

In some such embodiments, the relevant activity (e.g., of the modified PRE and/or other PRE, such as unmodified or wild-type PRE to which it is being compared), is the enhancement or promotion of expression of a recombinant protein encoded by a nucleic acid operably linked to the modified PRE. In some embodiments, such enhancement or promotion is assessed by measuring the level of expression of a recombinant protein operably linked to the modified PRE within a vector, following transduction or other form of transfer of the vector into a host cell. The enhancement may be measured by determining a relative degree of such expression as compared to a vector not containing the respective PRE. The question of whether a modified PRE has the activity at the same level or degree or a substantial or acceptable degree thereof as compared to an unmodified PRE may be assessed using vectors containing the respective PREs. A number of well-known methods for assessing expression level of recombinant molecules may be used, such as detection by affinity-based methods, e.g., immuno-affinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof by the modified PRE.

1. Stop Codons

The stop codon in the modified PREs, e.g., within the variant X gene (e.g., one not present at a corresponding position in a corresponding wild-type or unmodified X gene or PRE) can be an amber (TAG), ochre (TAA), or opal (TGA) stop codon. In one embodiment, the stop codon is an amber (TAG) stop codon. In one embodiment, the stop codon is an opal (TGA) stop codon.

The stop codon can be introduced by nucleotide substitution, deletion or insertion. In one embodiment, the stop codon is introduced by nucleotide substitution. Nucleotide substitution minimizes the nucleotide changes, such as frame shifts, that can occur by deletion or insertion of nucleotide residues. Hence, nucleotide substitutions can minimize structural changes to the cis-regulatory sequences involved in PRE activity, such as the beta-element or a functional portion thereof. In some embodiments, the stop codon is formed by substitution of only a single nucleotide, such that two positions within the stop codon represent unmodified nucleotides present in the corresponding positions in the wild-type or unmodified sequence. In some embodiments, the stop codon is formed by substitution of two nucleotides, such that only one position within the stop codon represent unmodified nucleotides present in the corresponding position in the wild-type or unmodified sequence. In some embodiments, the stop codon is formed by substitution of three nucleotides, such that all positions within the stop codon differ compared to the corresponding codon of the wild-type or unmodified sequence.

The variant X gene can contain at least 1, 2, 3, 4, 5, 6 or more stop codons not present in the unmodified or wild-type X gene or not present in the unmodified or wild-type PRE. Generally, at least one stop codon is in-frame with the X protein reading frame. In some embodiments, the variant X gene contains a plurality of stop codons, such as at least 2, 3, 4, 5 or 6 stop codons.

In some embodiments, the plurality of stop codons includes at least two stop codons in which one is in-frame with the X protein reading frame and the other is in a different reading frame. In other embodiments, the plurality of stop codons includes at least three stop codons in each reading frame present in the variant X gene.

In some embodiments, the plurality of stop codons includes at least two stop codons in the same reading frame. Typically, the at least two stop codons are in the same reading frame as the X protein reading frame.

In some embodiments, each of the at least one stop codon(s) begins at a position within or no more than 36 nucleotides in the 3' direction from a position corresponding to the 5' position of a start codon of the X protein open reading frame, e.g. a codon corresponding to a start codon in a corresponding wild-type or unmodified X protein open reading frame, such as corresponding to a start codon in the X protein open reading frame set forth in SEQ ID NO:1 or SEQ ID NO:125 that begins position 411. Typically, the first stop codon, and, in some cases, each of the plurality of introduced stop codons, present in the variant X gene after the 5' position of a start codon of the X protein open reading frame begins within or no more than 36 nucleotides in the 3' direction from a position corresponding to the 5' position of the start codon. For example, in some embodiments, each of the at least one stop codon, e.g., the first stop codon or one or more of a plurality of stop codons present in the variant X gene after a position corresponding to the 5' position of a start codon of the X protein open reading frame, begins at a position within or no more than 35, 34, 33, 32, 31, 30, 29, 28, 27, 26, 25, 24, 23, 22, 21, 20, 19, 18, 17, 16, 15, 14, 13, 12, 11, 10 or 9 nucleotides in the 3' direction from a position corresponding to the 5' position of a start codon of the X protein open reading frame. In some embodiments, each of the at least one stop codon begins at a position within no more than 9, 12, 15, 18, or 21 nucleotides in the 3' direction from a position corresponding to the 5' position of a start codon of the X protein open reading frame, such as no more than 21 nucleotides from such position.

With reference to the exemplary WPRE set forth in SEQ ID NO:1 or SEQ ID NO:125, the position corresponding to the 5' position of a start codon of the X protein open reading frame corresponds to residue 411 (corresponding to residue 1503 of the WHV sequence set forth in SEQ ID NO:2). In some embodiments, the at least one stop codon, e.g. the first stop codon or one or more of a plurality of stop codons present in the variant X gene after a position corresponding to the 5' position of a start codon of the X protein open reading frame, begins at a position within or no more than 36, 35, 34, 33, 32, 31, 30, 29, 28, 27, 26, 25, 24, 23, 22, 21, 20, 19, 18, 17, 16, 15, 14, 13, 12, 11, 10 or 9 nucleotides in the 3' direction from a position corresponding to residue 411 in the WPRE set forth in SEQ ID NO:1 or SEQ ID NO:125, e.g., no more than 9, 12, 15, 18, or 21, e.g., no more than 21, nucleotides in the 3' direction from such position. It is readily within the level of a skilled artisan to identify a residue in another hepatitis PRE, such another WPRE, that corresponds to residue 411 to identify a 5' position of a codon that corresponds to a start codon of the exemplary wild-type PRE set forth in SEQ ID NO:1 or SEQ ID NO:125 (which is a portion of SEQ ID NO:1 containing residues 1-589 or SEQ ID NO:1). FIG. 2A-2E exemplifies the identification of corresponding residues in exemplary hepatitis PREs.

In some embodiments of a modified PRE containing a variant X gene with a plurality of stop codons, the stop codons can be present sequentially in each reading frame of the X gene. In some embodiments of a modified PRE containing a variant X gene with a plurality of stop codons, the stop codons can be present sequentially in the same reading frame.

In some embodiments of a modified PRE, the variant X gene does not contain an open reading frame of greater than at or about 39 nucleotides in length, such as greater than at or about 36 nucleotides, 33 nucleotides, 30 nucleotides, 27 nucleotides, 24 nucleotides, 21 nucleotides, 18 nucleotides, 15 nucleotides, or 12 nucleotides in length.

In some embodiments, the at least one stop codon, e.g. the first stop codon or one or more of a plurality of stop codons present in the variant X gene after a position corresponding to the 5' position of a start codon of the X protein open reading frame, begins at a position that is in-frame with the X protein reading frame. For example, in some embodiments, the at least one stop codon, e.g., the first stop codon or one or more of a plurality of stop codons present in the variant X gene after a position corresponding to the 5' position of a start codon of the X protein open reading frame, begins at a position within or no more than 36, 33, 30, 27, 24, 21, 18, 15, 12, or 9 nucleotides in the 3' direction from a position corresponding to the 5' position of a start codon of the X protein open reading frame, e.g., no more than 9, 12, 15, 18, or 21, e.g., no more than 21, nucleotides in the 3' direction from such position. In some embodiments, the at least one stop codon, e.g. the first stop codon or one or more of a plurality of stop codons present in the variant X gene after a position corresponding to the 5' position of a start codon of the X protein open reading frame, begins at a position within or no more than 36, 33, 30, 27, 24, 21, 18, 15, 12, or 9 nucleotides in the 3' direction from a position corresponding to residue 411 in the WPRE set forth in SEQ ID NO:1 or SEQ ID NO:125.

In some embodiments, the modified PRE contains a variant X gene that contains a stop codon or a plurality of stop codons beginning at positions 9, 13, 17 and/or 21 in the 3' direction from a position corresponding to the 5' position of a start codon of the X protein open reading frame. With reference to the exemplary WPRE set forth in SEQ ID NO:1 or SEQ ID NO:125, the modified PRE contains a variant X gene that contains a stop codon or a plurality of stop codons beginning at a nucleotide position corresponding to position 420, 424, 428 and/or 432 in the sequence set forth in SEQ ID NO:1 or SEQ ID NO:125. In such embodiments, one, two, three or all four positions can be the beginning of a stop codon.

In some embodiments, the modified PRE contains a variant X gene that contains four stop codon beginning at each of positions 9, 13, 17 and 21 in the 3' direction from a position corresponding to the 5' position of a start codon of the X protein open reading frame. With reference to the exemplary WPRE set forth in SEQ ID NO:1 or SEQ ID NO:125, the modified PRE contains a variant X gene that contains a stop codon beginning at a nucleotide position corresponding to position 420, 424, 428 and 432 in the sequence set forth in SEQ ID NO:1 or SEQ ID NO:125.

In some embodiments, the modified PRE comprises a sequence of nucleotides that exhibits at least 65% sequence identity, such as at least 70%, 75%, 80%, 85%, 86%, 87%, 88%, 89%, 89%, 90%, 91%, 92%, 93%, 94%, 95%, 96%, 97%, 98%, 99% or more sequence identity, to SEQ ID NO:1 or SEQ ID NO:125, so long as the modified PRE contains a variant X gene containing at least one stop codon not present in the X gene set forth in SEQ ID NO:1 or SEQ ID NO:125. In some embodiments, the modified PRE differs from SEQ ID NO:1 or SEQ ID NO:125 only by nucleotide substitution. In other embodiments, the modified PRE differs from SEQ ID NO:1 or 125 by nucleotide insertion or deletion. In some embodiments, the modified PRE can be longer or shorter than SEQ ID NO:1 or SEQ ID NO:125.

In some embodiments, the modified PRE does not contain any modifications in addition to the at least one stop codon not present in the wild-type or unmodified PRE.

Tables 2A and 2B set forth exemplary positions for introduction of at least one stop codons in a variant X gene or modified PRE, respectively. The corresponding SEQ ID NOs for sequences of the exemplary polynucleotides also are set forth. In some embodiments, provided are polynucleotides comprising a modified PRE containing a variant X gene comprising the sequence of nucleotides set forth in any of SEQ ID NOS: 44-58 or 141-155. In some embodiments, provided are polynucleotides comprising a modified PRE that have the sequence of nucleotides set forth in any of SEQ ID NOS: 29-43 or 126-140. In some embodiments, provided are polynucleotides containing such PREs operably linked to nucleic acids encoding recombinant molecules, such as recombinant antigen receptors, CARs, TCRs, chimeric receptors, immunomodulators, immunostimulatory molecules, and/or transduction or expression markers, and expression cassettes and vectors containing the same.

TABLE 2A

Exemplary Variant X gene with at least one introduced stop codon

| SEQ ID NOs | 5' Position of Introduced Stop Codon(s): Relative to 3' Position of X Gene Start Codon | X gene Start Codon |
|---|---|---|
| 44, 141 | 9, 13, 17, 21 | Unmodified |
| 45, 142 | 9, 13, 17 | Unmodified |
| 46, 143 | 9, 13, 21 | Unmodified |
| 47, 144 | 9, 17, 21 | Unmodified |
| 48, 145 | 13, 17, 21 | Unmodified |
| 49, 146 | 9, 13 | Unmodified |
| 50, 147 | 9, 17 | Unmodified |
| 51, 148 | 9, 21 | Unmodified |
| 52, 149 | 13, 17 | Unmodified |
| 53, 150 | 13, 21 | Unmodified |
| 54, 151 | 17, 21 | Unmodified |
| 55, 152 | 9 | Unmodified |
| 56, 153 | 13 | Unmodified |
| 57, 154 | 17 | Unmodified |
| 58, 155 | 21 | Unmodified |

TABLE 2B

Exemplary Modified PRE with at least one introduced stop codon

| SEQ ID NOs | 5' Position of Introduced Stop Codon(s): Relative to 3' Position of X Gene Start Codon | 5' Position of Introduced Stop Codon(s): Residue corresponding to SEQ ID NOs: 1 or 125 | X gene Start Codon | Promoter Sequence |
|---|---|---|---|---|
| 29, 126 | 9, 13, 17, 21 | 420, 424, 428, 432 | Unmodified | Unmodified |
| 30, 127 | 9, 13, 17 | 420, 424, 428 | Unmodified | Unmodified |
| 31, 128 | 9, 13, 21 | 420, 424, 432 | Unmodified | Unmodified |
| 32, 129 | 9, 17, 21 | 420, 428, 432 | Unmodified | Unmodified |
| 33, 130 | 13, 17, 21 | 424, 428, 432 | Unmodified | Unmodified |
| 34, 131 | 9, 13 | 420, 424 | Unmodified | Unmodified |
| 35, 132 | 9, 17 | 420, 428 | Unmodified | Unmodified |
| 36, 133 | 9, 21 | 420, 432 | Unmodified | Unmodified |
| 37, 134 | 13, 17 | 424, 428 | Unmodified | Unmodified |
| 38, 135 | 13, 21 | 424, 432 | Unmodified | Unmodified |
| 39, 136 | 17, 21 | 428, 432 | Unmodified | Unmodified |
| 40, 137 | 9 | 420 | Unmodified | Unmodified |
| 41, 138 | 13 | 424 | Unmodified | Unmodified |
| 42, 139 | 17 | 428 | Unmodified | Unmodified |
| 43, 140 | 21 | 432 | Unmodified | Unmodified |

2. Degradation Sequences

In some embodiments, the truncated X gene comprises a post-translational modification signal, which can include degradation sequences known to increase the rate by which a protein is degraded by the proteasome, thereby decreasing the protein's half-life. Non-limiting examples of such sequences include the incorporation of nucleotides encoding PEST sequences, ubiquitin binding domains, or amino acids following the N-end rule.

Pest sequences are amino acid regions rich in proline (P), glutamic acid (E), serine (S), and threonine (T). (Rogers S, Wells R, Rechsteiner M (1986). "Amino acid sequences common to rapidly degraded proteins: the PEST hypothesis". Science (journal) 234 (4774): 364-8. doi:10.1126/science.2876518. The presence of PEST regions can result in the rapid intracellular degradation of the proteins containing them. Thus, in some embodiments the variant X gene comprises nucleic acids encoding PEST regions.

In some embodiments, the variant X gene comprises nucleic acids encoding ubiquitin binding domains. Ubiquitin-binding domains (UBDs) are a collection of modular protein domains that non-covalently bind to ubiquitin. These motifs interpret and transmit information conferred by protein ubiquitination to control various cellular events, including proteasomal degradation. Thus, in some embodiments, the variant X gene can be operably linked to nucleic acids encoding ubiquitin binding domains such that ubiquitin ligases target the variant X protein for ubiquitin labeling, and thus degradation by the proteasome, more rapidly. Non-limiting examples of ubiquitin binding domains include CUE, GAT, GLUE, NZF, PAZ, UBA, UEV, UIM, and VHS. See Hicke, Ubiquitin-Binding Domains, doi:10.1038/nrm1701.

In some embodiments, the variant X gene comprises mutations corresponding to amino acid substitutions that decrease X protein stability according to the N-end rule. In the N-end rule, the identity of the amino acid that is exposed at the N-terminus of a polypeptide following the removal of the initiation methionine can impact the polypeptide's metabolic stability and half-life. (Varshaysky, A, 1996 The N-end rule: functions, mysteries, uses. Proc Natl Acad. Sci. USA 93(22):12142-12149. This amino acid can be called a destabilizing amino acid. Thus, in some embodiments, the modified PRE comprises mutations in the variant X gene in which the start codon is immediately followed by a codon encoding a destabilizing amino acid. Non-limiting examples of destabilizing amino acids include glycine, arginine, glutamic acid, phenylalanine, aspartate, cysteine, lysine, asparagine, serine, tyrosine, tryptophan, histidine, and leucine. See Varshaysky 1996; see also Gonda et al. (1989). "Universality and Structure of the N-end Rule.". Journal of Biological Chemistry 264 (28): 16700-16712. In some embodiments, the modified PRE comprises mutations in the variant X gene in which the start codon is immediately followed by codons encoding a primary destabilizing amino acid and a secondary destabilizing amino acid. These mutations may correspond to pairs of amino acids, such as arginine-glutamic acid, or arginine-asparagine. In some embodiments, the arginine is the primary destabilizing amino acid and the glutamic acid or asparagine is the secondary destabilizing amino acid.

3. Other Modifications

Provided are polynucleotides containing a modified PRE that contains additional modifications in addition to any described above. In some embodiments, the additional modifications can be any modification of the X gene contained in the modified PRE that reduce or prevent one of more of the expression, degradation, stability, oncogenicity and/or immunogenicity of the X gene or encoded X protein. In some embodiments, the additional modifications alter, such as reduce, the transcription of the variant X gene and/or translation of the X protein encoded by the variant X gene.

In one embodiment, the modified PRE additionally contains a variant of an X gene start codon, which, in some cases, is introduced to restrict or prevent translation initiation. In some embodiments, the variant of the start codon contains one or more nucleotide differences compared to an unmodified X gene start codon, such as a wild-type hepatitis virus X gene start codon. For example, with reference to SEQ ID NO:1 or SEQ ID NO:125, the modified PRE can additionally contain a variant start codon containing one or more nucleotide differences compared to the start codon corresponding to nucleotide positions 411-413 of SEQ ID NO:1 or SEQ ID NO:125. It is readily within the level of a skilled artisan to identify a residue in another hepatitis PRE, such another WPRE, that corresponds to start codon positions 411-413 of SEQ ID NO:1 or SEQ ID NO:125 (see e.g. FIG. 2A-2E). The nucleotide differences can result in restricted or prevented translation initiation.

In some embodiments, the variant of the start codon can be the variant codon found at the position corresponding to an X gene start codon within the variant X gene reading frame of the modified WPRE sequence set forth in SEQ ID NO:119 or SEQ ID NO:216. For example, the variant of the start codon can be a codon corresponding to nucleotide residues 411-413 (TTG) of the sequence of nucleotides set forth in SEQ ID NO:119 or SEQ ID NO:216. In some embodiments, the variant of a start codon can be a codon of the X gene reading frame in the modified WPRE set forth in SEQ ID NO:120. For example, the variant of a start codon can be a codon corresponding to nucleotide residues 411-413 (GGG) of the sequence of nucleotides set forth in SEQ ID NO:120.

Tables 3A and 3B sets forth exemplary variant X genes and modified PRE polynucleotides containing a variant X gene, respectively, in which is contained at least one introduced stop codon and a variant start codon not present in a wild-type or unmodified X gene or PRE. The Table sets forth exemplary positions for introduction of the at least one stop codon in the variant X gene or modified PRE. The corresponding SEQ ID NO for sequences of the exemplary polynucleotides also are set forth. In some embodiments, the variant X gene comprises the sequence of nucleotides set forth in any of SEQ ID NOS: 74-88 or 171-185. In some embodiments, the modified PRE comprises the sequence of nucleotides set forth in any of SEQ ID NOS: 59-73 or 156-170. In some embodiments, provided are polynucleotides containing such PREs operably linked to nucleic acids encoding recombinant molecules, such as recombinant antigen receptors, CARs, TCRs, chimeric receptors, immunomodulators, immunostimulatory molecules, and/or transduction or expression markers, and expression cassettes and vectors containing the same.

In another embodiment, the modified PRE can additionally contain a variant promoter operably linked to the variant X gene therein. The variant promoter can contain one or more nucleotide differences compared to an unmodified hepatitis virus X gene promoter, such as a wild-type hepatitis virus X gene promoter. For example, with reference to SEQ ID NO:1 or SEQ ID NO:125, the variant X gene can contain one or more nucleotide differences compared to the WPRE X gene promoter set forth in SEQ ID NO:11 or set forth as nucleotides 7-20 of SEQ ID NO:11. In some embodiments, the nucleotide differences can result in one or more differences that result in restricted or prevention of transcription from the promoter.

In some embodiments, the modified PRE can contain a variant promoter that has the sequence of the variant promoter operably linked to the modified X gene within the modified PRE sequence set forth as SEQ ID NO:119 or SEQ ID NO:216. For example, the variant promoter can be a variant promoter comprising nucleotide residues corresponding to residues 391-411 (GGGGAAATCATCGTC-CTTTCC; SEQ ID NO:217) or nucleotide residues 397-410 (ATCATCGTCCTTTC; SEQ ID NO:218), each of the sequence of nucleotides set forth in SEQ ID NO:119 or SEQ ID NO:216. In some embodiments, the modified PRE can contain a variant promoter that has the sequence of the variant promoter operably linked to the modified X gene within the modified PRE set forth in SEQ ID NO:120. For example, the variant promoter can be a variant promoter comprising nucleotide residues corresponding to residues 391-411 (GGGGAAGGTCTGCTGAGACTC; SEQ ID NO:219) or nucleotide residues 397-410 (GGTCTGCT-GAGACT; SEQ ID NO:220), each of the sequence of nucleotides set forth in SEQ ID NO:120.

In some embodiments, the variant promoter can be a variant promoter that is a hepatitis X protein promoter known in the art, such as any described in Sugata et al. (1994) Virology, 205:314-320. In some embodiments, the variant X promoter can be a variant of a promoter set forth in SEQ ID NO:11 or a promoter that comprises nucleotides 6-22 of SEQ ID NO:10 that includes a mutation of the threonine (T) at a position corresponding to position 9 of SEQ ID NO:10 or a mutation of the glycine (G) at a position corresponding to position 10 of SEQ ID NO:10.

Table 3A and 3B sets forth exemplary variant X genes and modified PRE polynucleotides containing a variant X gene, respectively, in which is contained at least one introduced stop codon, a variant promoter and, optionally, a variant start codon not present in a wild-type or unmodified PRE. The Table sets forth exemplary positions for introduction of the at least one stop codon in a variant X gene or modified PRE. The corresponding SEQ ID NO for sequences of the exemplary polynucleotides also are set forth. In some embodiments, the modified PRE comprises the sequence of nucleotides set forth in any of SEQ ID NOS: 89-118 or 186-215. In some embodiments, provided are polynucleotides containing such PREs operably linked to nucleic acids encoding recombinant molecules, such as recombinant antigen receptors, CARs, TCRs, chimeric receptors, immunomodulators, immunostimulatory molecules, and/or transduction or expression markers, and expression cassettes and vectors containing the same.

TABLE 3A

Exemplary Variant X gene with at least one introduced stop codon and a modified X gene start codon

| SEQ ID NOs | 5' Position of Introduced Stop Codon(s) Relative to 3' Position of X Gene Start Codon | X gene Start Codon |
|---|---|---|
| 74, 171 | 9, 13, 17, 21 | Modified |
| 75, 172 | 9, 13, 17 | Modified |
| 76, 173 | 9, 13, 21 | Modified |
| 77, 174 | 9, 17, 21 | Modified |
| 78, 175 | 13, 17, 21 | Modified |
| 79, 176 | 9, 13 | Modified |
| 80, 177 | 9, 17 | Modified |
| 81, 178 | 9, 21 | Modified |
| 82, 179 | 13, 17 | Modified |
| 83, 180 | 13, 21 | Modified |
| 84, 181 | 17, 21 | Modified |
| 85, 182 | 9 | Modified |
| 86, 183 | 13 | Modified |
| 87, 184 | 17 | Modified |
| 88, 185 | 21 | Modified |

TABLE 3B

Exemplary Variant X gene with at least one introduced stop codon and a modified X gene start codon and/or promoter

| SEQ ID NOs | 5' Position of Introduced Stop Codon(s) Relative to 3' Position of X Gene Start Codon | Residue corresponding to SEQ ID NOs: 1 or 125 | X gene Start Codon | Promoter Sequence |
|---|---|---|---|---|
| 59, 156 | 9, 13, 17, 21 | 420, 424, 428, 432 | Modified | Unmodified |
| 60, 157 | 9, 13, 17 | 420, 424, 428 | Modified | Unmodified |
| 61, 158 | 9, 13, 21 | 420, 424, 432 | Modified | Unmodified |
| 62, 159 | 9, 17, 21 | 420, 428, 432 | Modified | Unmodified |
| 63, 160 | 13, 17, 21 | 424, 428, 432 | Modified | Unmodified |
| 64, 161 | 9, 13 | 420, 424 | Modified | Unmodified |
| 65, 162 | 9, 17 | 420, 428 | Modified | Unmodified |
| 66, 163 | 9, 21 | 420, 432 | Modified | Unmodified |
| 67, 164 | 13, 17 | 424, 428 | Modified | Unmodified |
| 68, 165 | 13, 21 | 424, 432 | Modified | Unmodified |
| 69, 166 | 17, 21 | 428, 432 | Modified | Unmodified |
| 70, 167 | 9 | 420 | Modified | Unmodified |
| 71, 168 | 13 | 424 | Modified | Unmodified |
| 72, 169 | 17 | 428 | Modified | Unmodified |
| 73, 170 | 21 | 432 | Modified | Unmodified |
| 89, 186 | 9, 13, 17, 21 | 420, 424, 428, 432 | Unmodified | Modified |
| 90, 187 | 9, 13, 17 | 420, 424, 428 | Unmodified | Modified |
| 91, 188 | 9, 13, 21 | 420, 424, 432 | Unmodified | Modified |
| 92, 189 | 9, 17, 21 | 420, 428, 432 | Unmodified | Modified |
| 93, 190 | 13, 17, 21 | 424, 428, 432 | Unmodified | Modified |
| 94, 191 | 9, 13 | 420, 424 | Unmodified | Modified |
| 95, 192 | 9, 17 | 420, 428 | Unmodified | Modified |
| 96, 193 | 9, 21 | 420, 432 | Unmodified | Modified |
| 97, 194 | 13, 17 | 424, 428 | Unmodified | Modified |
| 98, 195 | 13, 21 | 424, 432 | Unmodified | Modified |
| 99, 196 | 17, 21 | 428, 432 | Unmodified | Modified |
| 100, 197 | 9 | 420 | Unmodified | Modified |
| 101, 198 | 13 | 424 | Unmodified | Modified |
| 102, 199 | 17 | 428 | Unmodified | Modified |
| 103, 200 | 21 | 432 | Unmodified | Modified |
| 104, 201 | 9, 13, 17, 21 | 420, 424, 428, 432 | Modified | Modified |
| 105, 202 | 9, 13, 17 | 420, 424, 428 | Modified | Modified |
| 106, 203 | 9, 13, 21 | 420, 424, 432 | Modified | Modified |
| 107, 204 | 9, 17, 21 | 420, 428, 432 | Modified | Modified |
| 108, 205 | 13, 17, 21 | 424, 428, 432 | Modified | Modified |
| 109, 206 | 9, 13 | 420, 424 | Modified | Modified |
| 110, 207 | 9, 17 | 420, 428 | Modified | Modified |
| 111, 208 | 9, 21 | 420, 432 | Modified | Modified |
| 112, 209 | 13, 17 | 424, 428 | Modified | Modified |
| 113, 210 | 13, 21 | 424, 432 | Modified | Modified |
| 114, 211 | 17, 21 | 428, 432 | Modified | Modified |
| 115, 212 | 9 | 420 | Modified | Modified |
| 116, 213 | 13 | 424 | Modified | Modified |
| 117, 214 | 17 | 428 | Modified | Modified |
| 118, 215 | 21 | 432 | Modified | Modified |

B. Nucleic Acids Encoding Recombinant Molecules

In some embodiments, the modified PREs in the provided polynucleotides are operably linked to one or more nucleic acid encoding one or more molecule of interest, such as one or more recombinant and/or heterologous molecule, e.g., recombinant protein(s), such as heterologous protein(s). Such recombinant and/or heterologous molecules may include soluble proteins, e.g., secreted proteins, and/or cell surface proteins. In some embodiments, the molecule is or includes a recombinant receptor. Such recombinant receptors may include antigen receptors, such as functional non-TCR antigen receptors, including chimeric antigen receptors (CARs), and other antigen-binding receptors such as transgenic T cell receptors (TCRs). The receptors may also include other receptors, such as other chimeric receptors, such as receptors that bind to particular ligands and having transmembrane and/or intracellular signaling domains similar to those present in a CAR.

In some embodiments, the molecule is a soluble molecule, such as an immunomodulatory and/or immunostimulatory molecule, such as a cytokine, e.g., IL-2, IL-12, IL-6, 41BBL, CD40L, and/or soluble ligand or receptor such as a soluble ligand for an immune cell costimulatory molecule, e.g., CD40L, 41BBL, or a soluble antigen-binding molecule such as an scFv. Also among the molecules are expression or transduction markers and any other molecule(s) known for use in expression vectors and/or cassettes.

In some embodiments, the recombinant antigen receptor, e.g., CAR, specifically binds to one or more ligand on a cell or disease to be targeted, such as a cancer, infectious disease, inflammatory or autoimmune disease, or other disease or condition, including those described herein for targeting with the provided methods and compositions. Exemplary antigens are orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by and/or characteristic of or specific for HIV, HCV, HBV, HPV, and/or other pathogens and/or oncogenic versions thereof.

1. Chimeric Antigen Receptors

In some embodiments, the recombinant molecule is or includes a chimeric antigen receptor (CAR). The CAR is generally a genetically engineered receptor with an extracellular ligand binding domain linked to one or more intracellular signaling components. Such molecules typically mimic or approximate a signal through a natural antigen receptor and/or signal through such a receptor in combination with a costimulatory receptor.

In some embodiments, CARs are constructed with a specificity for a particular marker, such as a marker expressed in a particular cell type to be targeted by adoptive therapy, e.g., a cancer marker and/or any of the antigens described. Thus, the CAR typically includes one or more antigen-binding fragment, domain, or portion of an antibody, or one or more antibody variable domains, and/or antibody molecules. In some embodiments, the CAR includes an antigen-binding portion or portions of an antibody molecule, such as a variable heavy chain (VH) or antigen-binding portion thereof, or a single-chain antibody fragment (scFv) derived from the variable heavy (VH) and variable light (VL) chains of a monoclonal antibody (mAb).

The antigen-specific binding or recognition component is generally linked to one or more transmembrane and intracellular signaling domains. In some embodiments, the CAR includes a transmembrane domain fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD154. The transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

Primary cytoplasmic signaling sequences can in some aspects regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS.

In certain embodiments, the intracellular signaling domain comprises a CD28 transmembrane and signaling domain linked to a CD3 intracellular domain. In some embodiments, the intracellular signaling domain comprises a chimeric CD28 and CD137 co-stimulatory domains, linked to a CD3 intracellular domain. In some embodiments, a CAR can also include a transduction marker (e.g., tEGFR). In some embodiments, the intracellular signaling domain of the CD8$^+$ cytotoxic T cells is the same as the intracellular signaling domain of the CD4$^+$ helper T cells. In some embodiments, the intracellular signaling domain of the CD8$^+$ cytotoxic T cells is different than the intracellular signaling domain of the CD4$^+$ helper T cells.

In some embodiments, the CAR encompasses one or more, e.g., two or more, costimulatory domains and an activation domain, e.g., primary activation domain, in the cytoplasmic portion. One example is a receptor including intracellular components of CD3-zeta, CD28, and 4-1BB.

In some embodiments, the recombinant molecule(s) encoded by nucleic acid(s) within the provided polynucleotides further include one or more marker, e.g., for purposes of confirming transduction or engineering of the cell to express the receptor and/or selection and/or targeting of cells expressing molecule(s) encoded by the polynucleotide. In some aspects, such a marker may be encoded by a different nucleic acid or polynucleotide, which also may be introduced during the genetic engineering process, typically via the same method, e.g., transduction by the same vector or type of vector.

In some aspects, the marker, e.g., transduction marker, is a protein and/or is a cell surface molecule. Exemplary markers are truncated variants of a naturally-occurring, e.g., endogenous markers, such as naturally-occurring cell surface molecules. In some aspects, the variants have reduced immunogenicity, reduced trafficking function, and/or reduced signaling function compared to the natural or endogenous cell surface molecule.

In some aspects, the marker includes all or part (e.g., truncated form) of CD34, a NGFR, or epidermal growth factor receptor (e.g., tEGFR).

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

Antigen receptors, including CARs and recombinant TCRs, and production and introduction thereof, in some embodiments include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer*, 2012 Mar. 18(2): 160-75.

2. T Cell Receptors (TCRs)

In some embodiments, the recombinant molecule(s) encoded by the nucleic acid(s) is or include a recombinant T cell receptor (TCR). In some embodiments, the recombinant TCR is specific for an antigen, generally an antigen present on a target cell, such as a tumor-specific antigen, an antigen expressed on a particular cell type associated with an autoimmune or inflammatory disease, or an antigen derived from a viral pathogen or a bacterial pathogen.

In some embodiments, the TCR is one that has been cloned from naturally occurring T cells. In some embodiments, a high-affinity T cell clone for a target antigen (e.g., a cancer antigen) is identified and isolated from a patient. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15:169-180 and Cohen et al. (2005) *J Immunol.* 175:5799-5808. In some embodiments, phage display is used to isolate TCRs against a target antigen (see, e.g., Varela-Rohena et al. (2008) Nat Med. 14:1390-1395 and Li (2005) *Nat Biotechnol.* 23:349-354.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, the nucleic acid encoding a TCR further includes a marker to confirm transduction or engineering of the cell to express the receptor.

In some embodiments, the recombinant or heterologous molecule(s) encoded by the nucleic acid within the provided polynucleotide is or includes a nucleic acid molecule, such as an RNA, DNA, or artificial nucleic acid sequence, such as one designed for interference with expression or activity of a target mRNA, such as an short-interfering RNA (siRNA), short hairpin RNA (shRNA), or micro-RNA (miRNA). Such molecules may include those designed to interfere with expression or activity of molecules associated with, promoting, or inhibiting the activity of immune cells, such as immunomodulators, immunoinhibitory molecules, and immune checkpoint molecules. In some embodiments, a nucleotide siRNA or miRNA sequence (e.g. 21-25 nucleotides in length) can, for example, be produced from an expression vector by transcription of a short-hairpin RNA (shRNA) sequence, a longer (e.g. 60-80 nucleotide) precursor sequence, which is subsequently processed by the cellular RNAi machinery to produce either a siRNA or miRNA sequence. Alternatively, a nucleotide siRNA or miRNA sequence (e.g. 21-25 nucleotides in length) can, for example, be synthesized chemically. Chemical synthesis of siRNA or miRNA sequences is commercially available from such corporations as Dharmacon, Inc. (Lafayette, Colo.), Qiagen (Valencia, Calif.), and Ambion (Austin, Tex.). The RNA can be 10 to 30 nucleotides long, such as 19-25 or 21-25 nucleotides in length. For example, an siRNA sequence typically binds a unique sequence within a target mRNA with exact complementarity and results in the degradation of the target mRNA molecule. A siRNA sequence can bind anywhere within the mRNA molecule; sequences targeted by the siRNA include genes expressing a polypeptide of interest, or an upstream or downstream modulator of such a gene, e.g. an upstream or downstream modulator of a gene, such as a transcription factor that binds a gene promoter, a kinase or phosphatase that interacts with a polypeptide of interest, and polypeptides involved in regulatory pathways capable of influencing the polypeptide of interest. A miRNA sequence typically binds a unique sequence within a target mRNA with exact or less than exact complementarity and results in the translational repression of the target mRNA molecule. A miRNA sequence can bind anywhere within mRNA sequence, but generally binds within the 3' untranslated region of the mRNA molecule.

C. Expression Cassettes and Viral Vectors

In some embodiments, the polynucleotide is provided as or within an expression cassette. The polynucleotide or expression cassette can be contained in an expression vector, such as a viral vector, for expression of the recombinant and/or heterologous molecule encoded by the nucleic acid.

1. Expression Cassette

In some embodiments, the expression cassette can contain the heterologous and/or recombinant nucleic acid under the control of a promoter and operably linked to the modified PRE, such as any described above. The expression cassette also can contain one or more other regulatory elements. In addition to the modified PRE, the nucleic acid, may be operably linked to other nucleic acid sequences, including but not limited to, promoters, enhancers, other post-transcriptional regulatory elements, polyadenylation signals, restriction enzyme sites, multiple cloning sites or coding segments.

a. Promoters

In some embodiments, the expression cassette includes a promoter operably linked to the nucleic acid molecule encoding the recombinant or heterologous protein. The promoter can comprise any promoter desired by the user as appropriate for the expression context. In some embodiments, a promoter can comprise a promoter of eukaryotic or prokaryotic origin that can provide high levels of constitutive expression across a variety of cell types and will be sufficient to direct the transcription of nucleic acid encoding the recombinant or heterologous protein in a cell. In some embodiments, the nucleic acid encoding the recombinant or heterologous protein is a distally located sequence, which is a sequence operably linked to the 5' end of the promoter sequence. The promoter region can also include control elements for the enhancement or repression of transcription and can be modified as desired by the user and depending on the context.

In some embodiments, a promoter comprises a sequence that functions to position the start site for RNA synthesis. In some embodiments, the promoter comprises the TATA box. In some embodiments, the promoter lacks a TATA box, such as, for example, the promoter for the mammalian terminal deoxynucleotidyl transferase gene and the promoter for the SV40 late genes. In such an embodiment, the promoter can contain a discrete element overlying the start site itself helps to fix the place of initiation. Additional promoter elements regulate the frequency of transcriptional initiation. In some embodiments, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

In some embodiments, the spacing between promoter elements is flexible, so that promoter function is preserved when elements are inverted or moved relative to one another. In some embodiments in which the promoter is the tk promoter, the spacing between promoter elements can be increased to 50 bp apart before activity begins to decline. Depending on the promoter, individual elements can function either cooperatively or independently to activate transcription. In some embodiments, a promoter may be used in conjunction with an "enhancer," which refers to a cis-acting regulatory sequence involved in the transcriptional activation of a nucleic acid sequence.

In some embodiments a promoter may be one that is naturally associated with a nucleic acid sequence, as may be obtained by isolating the 5' non-coding sequences located upstream of the coding segment and/or exon. Such a promoter can be referred to as "endogenous." In some embodiments an enhancer may be one naturally associated with a nucleic acid sequence, located either downstream or upstream of that sequence.

Alternatively, in some embodiments the coding nucleic acid segment may be positioned under the control of a recombinant and/or heterologous promoter and/or enhancer, which is not normally associated with the coding nucleic acid sequence in the natural setting. Such promoters or enhancers may include promoters or enhancers which in nature are operably linked to other genes within the species from which the nucleic acid is derived, and promoters or enhancers isolated from other species, such as from other prokaryotic or eukaryotic cells, and promoters or enhancers that are not "naturally occurring," i.e., that contain different elements of different transcriptional regulatory regions, and/or mutations that alter expression compared with those found in any promoter or enhancer in nature. For example, exemplary promoters used in recombinant DNA construction include, but are not limited to, the β-lactamase (penicillinase), lactose, tryptophan (trp), RNA polymerase (pol) III promoters including, the human and murine U6 pol III promoters as well as the human and murine H1 RNA pol III promoters; RNA polymerase (pol) II promoters; cytomegalovirus immediate early promoter (pCMV), elongation factor-1 alpha (EF-1 alpha), and the Rous Sarcoma virus long terminal repeat promoter (pRSV) promoter systems. In addition to producing nucleic acid sequences of promoters and enhancers synthetically, sequences may be produced using recombinant cloning and/or nucleic acid amplification technology, including PCR™, in connection with the compositions and methods disclosed herein (see U.S. Pat. Nos. 4,683,202 and 5,928,906, each incorporated herein by reference). Furthermore, in some embodiments the control sequences that direct transcription and/or expression of sequences within non-nuclear organelles such as mitochondria, chloroplasts, and the like, can be employed as well. Control sequences comprising promoters, enhancers and other locus or transcription controlling/modulating elements are also referred to as "transcriptional cassettes".

In some embodiments, the promoter and/or enhancer is operably linked to effectively direct the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous for gene therapy or for applications such as the large-scale production of recombinant proteins and/or peptides. The promoter may be heterologous or endogenous.

In some embodiments, a T3, T7 or SP6 cytoplasmic expression system can be employed. Eukaryotic cells can support cytoplasmic transcription from certain bacterial promoters if the appropriate bacterial polymerase is provided, either as part of the delivery complex or as an additional genetic expression construct.

In some embodiments, an inducible promoter can be used. As used herein, an "inducible promoter" refers to a transcriptional control element that can be regulated in response to specific signals. An inducible promoter is transcriptionally active when bound to a transcriptional activator, which in turn is activated under a specific set of conditions, for example, in the presence of a particular combination of chemical signals that affect binding of the transcriptional activator to the inducible promoter and/or affect function of the transcriptional activator itself. Thus, an inducible promoter is a promoter that, either in the absence of an inducer, does not direct expression, or directs low levels of expression, of a nucleic acid sequence to which the inducible promoter is operably linked; or exhibits a low level of expression in the presence of a regulating factor that, when removed, allows high-level expression from the promoter, for example, the tet system. In the presence of an inducer, an inducible promoter directs transcription at an increased level.

In some embodiments, the tetracycline-(tet)-regulatable system, which is based on the inhibitory action of the tet repression (tetr) of *Escherichia coli* on the tet operator sequence (TECO), can be modified for use in mammalian systems and used as a regulatable element for expression cassettes. These systems are well known to those of ordinary skill in the art. (See, Goshen and Badgered, Proc. Natl. Acad. Sci. USA 89: 5547-51 (1992), Shockett et al., Proc. Natl. Acad. Sci. USA 92:6522-26 (1996), Lindemann et al., Mol. Med. 3:466-76 (1997)).

b. Other Regulatory Elements

In some embodiments, the expression cassette can additionally include an enhancer that is operably linked to the nucleic acid encoding the recombinant protein, e.g. heterologous protein.

In some embodiments, internal ribosome binding sites (IRES) elements are operably linked to expression cassettes to create multigene, or polycistronic, messages. IRES elements are able to bypass the ribosome scanning model of 5'-methylated cap-dependent translation and begin translation at internal sites (Pelletier and Sonenberg, 1988). Non-limiting examples of IRES elements include, but are not limited to, IRES elements of the picornavirus family (polio and encephalomyocarditis) (Pelletier and Sonenberg, 1988) or an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In some embodiments, the vectors or constructs will comprise at least one termination signal operably linked to the nucleic acid encoding a recombinant protein, such as a heterologous protein. A "termination signal" or "terminator" is comprised of the DNA sequences involved in specific termination of an RNA transcript by an RNA polymerase. Thus, in certain embodiments a termination signal that ends the production of an RNA transcript is contemplated. In some embodiments, a terminator may be used in vivo to achieve desirable message levels.

In some embodiments comprising eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in some embodiments involving eukaryotes, the terminator comprises a signal for the cleavage of the RNA. In some embodiments, the terminator signal promotes polyadenylation of the message. The terminator and/or polyadenylation site elements can serve to enhance message levels and to minimize read through from the cassette into other sequences.

Terminators include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In some embodiments involving eukaryotic gene expression, the expression cassette may be operably linked to a polyadenylation signal to effect proper polyadenylation of the transcript. Any such sequence may be employed. Some examples include the SV40 polyadenylation signal or the bovine growth hormone polyadenylation signal, convenient and known to function well in various target cells. Polyadenylation may increase the stability of the transcript or may facilitate cytoplasmic transport.

In some embodiments, the expression cassette or vector contains one or more origins of replication sites (often termed "ori") in order to propagate in a host cell. An origin of replication is a specific nucleic acid sequence at which replication is initiated. Alternatively an autonomously replicating sequence (ARS) can be employed if the host cell is yeast.

2. Viral Vectors

In some embodiments, the modified PREs, nucleic acids, and/or cassettes are provided within viral vectors. The nucleic acid within the vector can be provided as an expression cassette under the control of a promoter. The viral vectors can be used to transfer the nucleic acid molecule into cells for expression of the heterologous or recombinant protein therein.

Exemplary viral vectors include retroviral vectors, such as lentiviral or gammaretroviral vectors, vectors derived from simian virus 40 (SV40), adenoviruses, and adeno-associated virus (AAV). In some embodiments, recombinant nucleic acids are transferred into cells using retroviral vectors, such as lentiviral vectors or gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557. Retroviruses are useful as delivery vectors because of their ability to integrate their genes into the host genome, transferring a large amount of foreign genetic material, infecting a broad spectrum of species and cell types and of being packaged in special cell lines (Miller, 1992).

In some embodiments, genetic transfer is accomplished via lentiviral vectors. Lentiviruses, in contrast to other retroviruses, in some contexts may be used for transducing certain non-dividing cells.

Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In some embodiments, two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components. In some embodiments, the packaging plasmid can contain all HIV-1 proteins other than envelope proteins (Naldini et al., 1998). In some embodiments, viral vectors can lack additional viral genes, such as those that are associated with virulence, e.g. vpr, vif, vpu and nef, and/or Tat, a primary transactivator of HIV. In some embodiments, packaging systems for lentiviral vectors, such as HIV-based lentiviral vectors, include separate packaging plasmids that together comprise only three genes of the parental virus: gag, pol and rev, which reduces or eliminates the possibility of reconstitution of a wild-type virus through recombination.

In some aspects of the provided viral vectors, the heterologous nucleic acid encoding a recombinant protein, such as provided as part of an expression cassette containing the transgene under the control of a promoter, is contained and/or located between the 5' LTR and 3' LTR sequences of the vector genome, including wildtype LTRs or portions or chimeric portions thereof. In some embodiments, the viral vector, such as an HIV viral vector, lacks additional transcriptional units. In some embodiments, the vector genome can contain deletion in the U3 region of the 3' LTR of the DNA used to produce the viral vector RNA, which can generate a self-inactivating (SIN) vector. This deletion can then be transferred to the 5' LTR of the proviral DNA during reverse transcription. In some embodiments, the 3' LTR is deleted for the promoter and the enhancer of U3. In some embodiments enough sequence can be eliminated, including the removal of a TATA box, to abolish the transcriptional activity of the LTR. This can prevent production of full-length vector RNA in transduced cells. Thus, some embodiments include a deletion in the U3 region of the 3' LTR of the DNA. In some embodiments, this does not affect vector titers or the in vitro or in vivo properties of the vector.

In some embodiments, the viral vector genome may also contain additional genetic elements. The types of elements that can be included in the constructs are not limited in any way and can be chosen by one with skill in the art. In some embodiments, the vector genome contains sequences derived from a viral genome (e.g. lentiviral genome) that are non-coding regions of the genome that facilitate or provide recognition signals for DNA or RNA synthesis and processing. In some embodiments, such sequences can include cis-acting sequences that can be involved in packaging or encapsidation, reverse transcription and transcription and/or gene transfer or integration. In some embodiments, cis-activating sequences provided as part of the viral vector are derived from the same lentivirus or retrovirus-like organism.

In some embodiments, a signal that facilitates nuclear entry of the viral genome in the target cell may be included. An example of such a signal is the Flap sequence (also called a DNA Flap sequence) formed from the cPPT and CTS components that are part of the pol gene of a viral vector genome, such as a lentiviral vector genome. In some embodiments, a Flap sequence includes a portion of viral nucleic acid that contains a cPPT and/or a CTS region, but in which is deleted 5' and 3' portions of the pol gene that are not necessary for Flap function. In some cases, the viral vector does not contain a functional Flap region. As discussed below, in some embodiments a viral vector contains viral nucleic acid containing a variant Flap that lacks all or a portion of one or both of the cPPT and CTS region.

In some embodiments, the lentiviral vector genome can contain elements selected among a splice donor site (SD), a splice acceptor site (SA) and/or a Rev-responsive element (RRE). In some embodiments, RRE is provided to allow export of viral messenger RNA from the nucleus to the cytosol after binding of the Rev protein provided as part of a helper plasmid during viral packaging. In some embodiments, the vector genome can contain the psi (w) packaging signal, which, in some cases, can be derived from the N-terminal fragment of the gag ORF. In some embodiments, the psi packaging signal sequence can be modified by frameshift mutation(s) in order to prevent any interference of a possible transcription/translation of gag peptide, with that of the transgene.

In some embodiments, provided is a viral vector, such as a lentiviral vector, that contains a recombinant genome containing in order between the 5' and 3' LTR sequences of the vector genome: an RRE; a polynucleotide containing viral nucleic acid comprising a functional DNA Flap containing a cPPT and CTS that is inserted upstream of a promoter controlling expression of a polynucleotide encoding a recombinant protein; a transgene containing a promoter controlling expression of a polynucleotide encoding the recombinant protein, such as any described above and the polynucleotide encoding the recombinant protein, such as an antigen receptor (e.g. a CAR); and a polynucleotide containing a modified PRE, such as any provided herein, operably linked to the nucleic acid encoding the recombinant protein such as any provided herein. In some embodiments, the recombinant genome comprises the sequence 5' LTR-RRE-cPPT-CTS-transgene(s)-modified PRE-3' LTR. In some embodiments, the modified PRE in the viral vector, such as lentiviral vector, has the sequence of nucleotides set forth in any of SEQ ID NOS: 29-43, 59-73, 89-118, 126-140, 156-170 or 186-215. In some embodiments, the modified PRE is or comprises the sequence of nucleotides set forth in SEQ ID NO:29 or SEQ ID NO:126. In some embodiments, the cPPT and CTS are inserted as a fragment of a viral nucleic acid sequence containing an unmodified or wild-type DNA Flap, such as that is or comprises the exemplary sequence set forth in SEQ ID NO:121 or a functional fragment thereof that contains the cPPT and CTS sequences. In some embodiments, the lentiviral vector is an HIV-1 derived lentiviral vector.

In some embodiments, among the provided polynucleotides, including viral vectors, are those containing variations in viral Flap sequences (deemed "variant Flap" polynucleotides or sequences). Such polynucleotides include those containing one or more modifications, e.g., deletion(s), within a viral Flap sequence within the polynucleotide. The variations can include complete deletion of a Flap sequence, or sub-part thereof, within a viral sequence of the polynucleotide. Such polynucleotides include viral vectors, such as a lentiviral vector, containing such variant Flap sequences.

In general, a viral Flap sequence is a viral regulatory region containing a polynucleotide sequence including two components: a central polypurine tract (cPPT) and a central termination sequence (CTS). See, e.g. Iglesias et al., *Retrovirology* 2011, 8:92. A non-limiting, exemplary cPPT sequence is provided in SEQ ID NO:123. A non-limiting, exemplary CTS sequence is provided in SEQ ID NO:124. In an exemplary wild-type HIV-1, the cPPT and CTS can be operably linked by approximately 70-100 nucleotides. It is reported that the cPPT and CTS are positioned at or about the center of the lentiviral vector genome, such that following reverse transcription, DNA encoded by the cPPT and CTS sequences form an approximately 100 nucleotide overlap, or "DNA Flap", at the center of the genome. When inserted in viral vectors, such as lentiviral derived vectors, the polynucleotide permitting the DNA flap to be produced during retro-transcription, stimulates gene transfer efficiency and complements the level of nuclear import to wild-type levels.

In some embodiments, the variant Flap polynucleotide contains deletions of all or a portion of nucleotides in the CTS, the cPPT or both the CTS and cPPT with reference to a sequence of a wild-type or unmodified Flap sequence. In some embodiments, the sequence of a wild-type or unmodified Flap sequence is a viral nucleic acid sequence containing the cPPT and CTS that is derived from a retrovirus, such as a lentivirus, or from a retrovirus-like organism such as retrotransposon. In some embodiments, the sequence of a wild-type or unmodified Flap is from a human retrovirus or lentivirus, such as an HIV retrovirus (e.g. HIV-1 or HIV-2). In some embodiments, the sequence of a wild-type or unmodified DNA Flap is from an CAEV (Caprine Arthritis Encephalitis Virus) virus, an EIAV (Equine Infectious Anaemia Virus) virus, a VI SNA virus, the SIV (Simian Immunodeficiency Virus) virus or a FIV (Feline Immunodeficiency Virus) virus. In some embodiments, the viral nucleic acid sequence containing the wild-type or unmodified Flap can contain additional flanking sequence present in the viral genome. In some embodiments, the polynucleotide containing a wild-type or unmodified Flap can have a sequence of about 80 to about 200 nucleotides, depending on its origin and preparation. In some embodiments, the wild-type or unmodified Flap sequence can be prepared synthetically (chemical synthesis) or by amplification of polynucleotides containing the Flap from any retrovirus, such as from a lentivirus nucleic acid, for example by polymerase chain reaction (PCR).

In some embodiments, a wild-type or unmodified Flap sequence can be derived from a polynucleotide sequence present in HIV-1, such as corresponding to a 178 base pair fragment from positions 4757 to 4935 or a 179 base pair fragment from positions 4746 to 4935 of the exemplary HIV-1 vector pNL4-3 (GenBank No. AF324493), or a shorter or longer sequence present therein containing the cPPT and CTS that is capable of producing the Flap upon reverse transcription. In some embodiments, an exemplary polynucleotide sequence containing a wild-type or unmodified Flap is or comprises the sequence set forth in SEQ ID NO:121, a sequence that exhibits at least 85%, 85%, 87%, 88%, 89%, 90%, 91%, 92%, 93%, 94%, 95%, 96%, 97%, 98% or 99% sequence identity to SEQ ID NO:121 or a functional fragment thereof containing the cPPT and CTS for producing the Flap structure upon reverse transcription. In some embodiments, the cPPT is or comprises a sequence corresponding to nucleotides 30-45 of SEQ ID NO:121 (set forth in SEQ ID NO:123) and the CTS is or comprises a sequence corresponding to nucleotides 117-143 of SEQ ID NO:121 (set forth in SEQ ID NO:124).

In some embodiments of the provided polynucleotides or viral vectors comprising a variant, e.g., deleted, Flap sequence, the variant Flap sequence can be one in which all or a portion of the Flap region of the viral nucleic acid(s) within the vector is deleted and/or mutated, including all or a portion of the cPPT and/or CTS. In some embodiments, the variant Flap sequence includes viral sequences completely lacking or substantially lacking the entire Flap sequence or portion thereof. In some embodiments, the variant Flap contains deletion(s) in the cPPT, the CTS, or both the cPPT and CTS. In some embodiments the variant Flap can contain a cPPT with at least 1, 2, 3, 4, 5, 6, 7, 8, 9, 10, 11, 12, 13, 14, 15, or 16 nucleotide deletions, which can be contiguous nucleotide deletions, compared to a wild-type or unmodified cPPT sequence, such as compared to the exemplary unmodified cPPT set forth in SEQ ID NO:123. In some embodiments, the cPPT can be deleted entirely. In some embodiments, the variant DNA Flap can contain a CTS with at least 1, 2, 3, 4, 5, 6, 7, 8, 9, 10, 11, 12, 13, 14, 15, 16, 17, 18, 19, 20, 21, 22, 23, 24, 25, 26, or 27 nucleotide deletions, which can be contiguous nucleotide deletions, compared to a wild-type or unmodified CTS sequence, such as compared to the exemplary unmodified CTS set forth in SEQ ID NO:124. In some embodiments, the CTS can be deleted entirely.

In some embodiments, the variant Flap polynucleotide contains deletion of all or a contiguous portion of the cPPT and contains a wild-type CTS. In some embodiments, the variant Flap polynucleotide contains a wild-type cPPT and contains deletion of all or a contiguous portion the CTS.

In some embodiments, the variant Flap contains a deletion of all or a portion of the cPPT and contains deletion of all or a portion of the CTS. In some embodiments, the variant DNA Flap can contain a cPPT with at least 1, 2, 3, 4, 5, 6, 7, 8, 9, 10, 11, 12, 13, 14, 15, or 16 nucleotide deletions, which can be contiguous nucleotide deletions, compared to a wild-type or unmodified cPPT, such as compared to the exemplary unmodified cPPT set forth in SEQ ID NO:123, or can have the cPPT deleted entirely and contain a CTS with at least 1, 2, 3, 4, 5, 6, 7, 8, 9, 10, 11, 12, 13, 14, 15, 16, 17, 18, 19, 20, 21, 22, 23, 24, 25, 26, or 27 nucleotide deletions, which can be contiguous nucleotide deletions, compared to a wild-type or unmodified CTS, such as compared to the exemplary unmodified CTS of SEQ ID NO:124, or have the CTS deleted entirely.

In some embodiments, the polynucleotide containing a variant Flap sequence is or comprises a sequence of nucleotides that exhibits at least 65%, 70%, 71%, 72%, 73%, 74%, 75%, 76%, 78%, 78%, 79%, 80%, 81%, 82%, 83%, 84%, 85%, 90% or 95% sequence identity to SEQ ID NO:121, but that lacks all or a portion of the cPPT and/or CTS present in SEQ ID NO:121. In some embodiments, the polynucleotide containing a variant Flap sequence or polynucleotide is, comprises or contains a portion having a nucleotide sequence with at least or about at least 65%, 70%, 75%, 80%, 85%, 90%, 95%, 96%, 97%, 98%, or 99% or more sequence identity to SEQ ID NO:122 in which all or a portion of a cPPT and/or CTS is deleted. A non-limiting, exemplary variant Flap polynucleotide is provided as SEQ ID NO:122.

In some embodiments, the deletion of all or a portion of nucleotides in the CTS and/or the cPPT in a provided variant Flap is introduced into a polynucleotide sequence containing an unmodified or wild-type Flap by recombinant DNA techniques. In some embodiments, the variant Flap polynucleotide is produced synthetically, such as by chemical synthesis.

In some embodiments, the polynucleotide, e.g., viral vector, contains a variant Flap sequence and a PRE. In some embodiments, the PRE can be a modified PRE, such as any described above. Thus, in some embodiments, the polynucleotides contain nucleotide sequences containing variant Flap polynucleotides and containing modified PRE polynucleotides. In some embodiments, such a polynucleotide and/or viral vector contains the sequence of SEQ ID NO: 122 or one having at least at or about 90%, 91%, 92%, 93%, 94%, 95%, 96%, 97%, 98%, or 99% sequence identity to SEQ ID NO:122 in which all or a portion of the cPPT and CTS are deleted, and a sequence for the modified PRE set forth in SEQ ID NO:29 or SEQ ID NO:126 or one having at least at or about 90%, 91%, 92%, 93%, 94%, 95%, 96%, 97%, 98%, or 99% sequence identity to SEQ ID NO:29 or SEQ ID NO:126 containing the introduced stop codon modifications.

In some embodiments, provided is a viral vector, such as a lentiviral vector, that contains a recombinant genome containing in order between the 5' and 3' LTR sequences of the vector genome: an RRE; a polynucleotide containing viral nucleic acid comprising a variant DNA Flap containing a deletion of all or a portion of the cPPT and CTS, which variant DNA Flap is inserted upstream of a promoter controlling expression of a polynucleotide encoding a recombinant protein; a transgene containing a promoter controlling expression of a polynucleotide encoding the recombinant protein, such as any described above and the polynucleotide encoding the recombinant protein, such as an antigen receptor (e.g. a CAR); and a polynucleotide containing a modified PRE, such as any provided herein, operably linked to the nucleic acid encoding the recombinant protein such as any provided herein. In some embodiments, the recombinant genome comprises the sequence 5' LTR-RRE-variant DNA Flap-transgene(s)-modified PRE-3' LTR. In some embodiments, the modified PRE in the viral vector, such as lentiviral vector, has the sequence of nucleotides set forth in any of SEQ ID NOS: 29-43, 59-73, 89-118, 126-140, 156-170 or 186-215. In some embodiments, the modified PRE is or comprises the sequence of nucleotides set forth in SEQ ID NO:29 or SEQ ID NO:126. In some embodiments, the polynucleotide containing viral nucleic acid containing a variant DNA Flap is or comprises the sequence of nucleotides set forth in SEQ ID NO: 122. In some embodiments, the lentiviral vector is an HIV-1 derived lentiviral vector.

In some embodiments, a polynucleotide, such as a viral vector, containing a variant DNA Flap as provided and/or a modified PRE as provided can be used to transfer a nucleic acid molecule encoding a recombinant or heterologous protein contained therein into cells for transduction and expression of such protein. In some embodiments, while still resulting in successful transduction of cells, such transduction by the provided viral vectors, in some cases, can be less than, such as up to or up to about a 1.1-fold, 1.2-fold, 1.5-fold, 2.0-fold, 3.0-fold, 4.0-fold or more less than or decrease of, transduction as compared to transduction using the same or substantially similar amount and concentration of a corresponding viral vector containing substantially the same genome but that contains an unmodified or wild-type DNA Flap sequence in which is present the cPPT and CTS for formation of the DNA Flap structure. In some cases, where higher transduction efficiency is desired, transduction efficiency can be increased by increasing the volume or the concentration of the viral vector used to transduce the cells. In other cases, the number of transduced cells can be enriched or increased by cell sorting and expansion of transduced cells.

In some embodiments, the vector also can contain sequences for propagation in a host cell, such as a prokaryotic host cell. In some embodiments, the nucleic acid of the viral vector contains one or more origins of replication for propagation in a prokaryotic cell, such as a bacterial cell. In some embodiments, vectors that include a prokaryotic origin of replication also may contain a gene whose expression confers a detectable or selectable marker such as drug resistance.

3. Preparation of Viral Vector Particles

In some embodiments, the nucleic acid, e.g., one encoding the desired sequence, such as the polynucleotide or expression cassette, is inserted into the viral genome in the place of certain viral sequences to produce a virus that is replication defective. In order to produce virions, a packaging cell line containing the gag, pol, and env genes but without the LTR and packaging components may be constructed. A recombinant plasmid also can be employed containing a polynucleotide, such as expression cassette, containing nucleic acid encoding a recombinant protein under the operable control of a modified PRE. When a recombinant plasmid together with the retroviral LTR and packaging sequences is introduced into a special cell line (e.g., by calcium phosphate precipitation for example), the packaging sequence may permit the RNA transcript of the recombinant plasmid to be packaged into viral particles, which then may be secreted into the culture media. The media containing the recombinant retroviruses in some embodiments is then collected, optionally concentrated, and used for gene transfer.

In some embodiments, a packaging cell line is transfected with one or more plasmid vectors containing the components necessary to generate the particles. The packaging cell line can express or be made to express essential lentiviral (e.g. HIV-1) genes to allow the generation of lentiviral particles. These genes can be expressed by several plasmids. In some embodiments, multiple vectors are utilized to separate the various genetic components that generate the retroviral vector particles. In some such embodiments, providing separate vectors to the packaging cell reduces the chance of recombination events that might otherwise generate replication competent viruses.

In some embodiments, a packaging cell line can be transfected with a lentiviral expression plasmid containing a cis-acting psi (Ψ) packaging sequence and the transgene gene inserted between the lentiviral LTRs to allow target cell integration; a packaging plasmid or plasmids encoding the pol, gag, rev and/or tat viral genes and, in some cases, containing the rev-response element (RRE) and a pseudotyping plasmid, such as a plasmid encoding an envelope protein, such as the G protein of the Vesicular Stomatitis Virus (VSV-G) envelope gene.

In some embodiments, a packaging cell line is transfected with a plasmid containing the viral vector genome, including the LTRs, the cis-acting packaging sequence and the sequence of interest, i.e. a nucleic acid encoding a recombinant protein, (e.g. an antigen receptor, such as a CAR) along with several helper plasmids encoding the virus enzymatic and/or structural components, such as Env, Gag, pol and/or rev. In some embodiments, a GagPol packaging plasmid containing the gag and pol genes encoding for structural and enzymatic components and a Rev plasmid containing the rev gene encoding for Rev regulatory protein are separately introduced into a packaging cell line. In some embodiments, a single plasmid vector having all of the retroviral components can be used. In some embodiments, an envelope plasmid encoding an env gene also can be introduced, which, in some cases, can result in viral particles pseudotyped with alternative Env proteins. In some embodiments, the retroviral vector particle, such as lentiviral vector particle, is pseudotyped to increase the transduction efficiency of host cells. For example, a retroviral vector particle, such as a lentiviral vector particle, is pseudotyped with a VSV-G glycoprotein, which provides a broad cell host range extending the cell types that can be transduced.

The env gene can be derived from any appropriate virus, such as a retrovirus. In some embodiments, the env is an amphotropic envelope protein which allows transduction of cells of human and other species. Some embodiments use retroviral-derived env genes, including, but not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). In some embodiments, other env genes such as Vesicular stomatitis virus (VSV) protein G (VSVG), that of hepatitis viruses, and of influenza also can be used.

In some embodiments, the packaging plasmid providing the viral env nucleic acid sequence is associated operably linked with regulatory sequences, e.g., a promoter or enhancer. The regulatory sequence in some embodiments can be any eukaryotic promoter or enhancer, including for example, EF1α, PGK, the Moloney murine leukemia virus promoter-enhancer element, the human cytomegalovirus enhancer, the vaccinia P7.5 promoter or the like. In some cases, such as the Moloney murine leukemia virus promoter-enhancer element, the promoter-enhancer elements are located within or adjacent to the LTR sequences. In some embodiments, the regulatory sequence is one which is not endogenous to the lentivirus from which the vector is being constructed. Thus, if the vector is being made from SIV, the SIV regulatory sequence found in the SIV LTR may be replaced by a regulatory element which does not originate from SIV.

In some embodiments, the viral vectors and the packaging plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection. After cotransfection of the packaging plasmids and the transfer vector to the packaging cell line, the viral vector particles are recovered from the culture media and tittered by standard methods used by those of skill in the art. Thus, the packaging plasmids in some embodiments are introduced into human cell lines by these methods, generally together with a dominant selectable marker, such as neomycin, DHFR, Glutamine synthetase or ADA, followed by selection in the presence of the appropriate drug and isolation of clones. The selectable marker gene can be linked physically to the packaging genes in the construct.

In some embodiments, viral vector particles can be produced by stable cell lines wherein the packaging functions are configured to be expressed. Suitable packaging cells are known including, for example, U.S. Pat. No. 5,686,279; and Ory et al., (1996). The packaging cells with a lentiviral vector incorporated in them form producer cells. Producer cells are thus cells or cell-lines that can produce or release viral vector particles carrying the gene of interest. In some embodiments, these cells can further be anchorage dependent, which means that these cells will grow, survive, or maintain function optimally when attached to a surface such as glass or plastic. In some embodiments, the producer cells may be neoplastically transformed cells. In some embodiments, host cells for transfection with the lentiviral vector and packaging plasmids include, for example, mammalian primary cells; established mammalian cell lines, such as COS, CHO, HeLa, NIH3T3, 293T and PC12 cells; amphibian cells, such as *Xenopus* embryos and oocytes; other vertebrate cells; insect cells (for example, *Drosophila*), yeast cells (for example, *S. cerevisiae, S. pombe*, or *Pichia pastoris*) and prokaryotic cells (for example, *E. coli*).

In some embodiments, lentiviral vectors can be produced in a packaging cell line, such as an exemplary HEK 293T cell line, by introduction of plasmids to allow generation of lentiviral particles. Approximately two days after transfection of cells, e.g. HEK 293T cells, the cell supernatant contains recombinant lentiviral vectors, which can be used to transduce the target cells. Once in the target cells, the viral RNA is reverse-transcribed, imported into the nucleus and stably integrated into the host genome. One or two days after the integration of the viral RNA, the expression of the recombinant protein can be detected.

D. Methods of Production and Methods of Engineering Cells

Also provided are methods of producing the polynucleotides containing the modified PREs, and/or cassettes, vectors, and/or engineered cells containing the same. In some embodiments, the methods include introducing the modification(s) into a wild-type or unmodified PRE sequence or another starting modified PRE sequence, such as one known to have a particular degree of activity. In some embodiments, such modifications are effected by mutating an existing vector.

The methods further include those for engineering cells by introducing into a cell a polynucleotide containing a modified PRE as provided herein, operably linked to a nucleic acid encoding the recombinant molecule, such as the recombinant protein, such as the heterologous protein, e.g. an antigen receptor, such as a TCR or CAR, or other chimeric receptor. The polynucleotide can be introduced into the cells in the context of a viral vector particle containing in its genome the provided polynucleotide, including the nucleic acid encoding the recombinant molecule, such as the heterologous protein. Also provided are cells containing the polynucleotides, cassettes, and/or vectors with the modified PREs and nucleic acids and compositions containing the same and/or produced by the provided methods.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some embodiments, the cells are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MALT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

The genetic engineering generally involves introduction of the polynucleotide(s) into the cell, such as by retroviral transduction, transfection, or transformation, as described above.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the subject to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments, preparation of the engineered cells includes one or more culture and/or preparation steps. The cells for introduction of the nucleic acid encoding the modified PRE may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished in a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched CD8$^+$ T cells and CD4$^+$ T cells further enhances efficacy.

In embodiments, memory T cells are present in both CD62L$^+$ and CD62L$^-$ subsets of CD8$^+$ peripheral blood lymphocytes. PBMC can be enriched for or depleted of CD62L$^-$CD8$^+$ and/or CD62L$^+$CD8$^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8$^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naive CD4$^+$ T lymphocytes are CD45RO$^-$, CD45RA$^+$, CD62L$^+$, CD4$^+$ T cells. In some embodiments, central memory CD4$^+$ cells are CD62L$^+$ and CD45RO$^+$. In some embodiments, effector CD4$^+$ cells are CD62L$^-$ and CD45RO$^-$.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unit that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

II. Compositions, Methods and Uses

A. Pharmaceutical Compositions and Formulations

Also provided are compositions including the polynucleotides, cassettes, vectors, viral particles and/or cells into which such polynucleotides have been introduced or otherwise containing the same. In some embodiments, provided are pharmaceutical compositions containing cells that have been engineered to express a recombinant protein by transduction methods employing any of the provided vectors or viral particles containing the same. Among the compositions are compositions for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

In some embodiments, the composition includes the cells in an amount effective to reduce burden of the disease or condition, and/or in an amount that does not result in CRS or severe CRS in the subject and/or to effect any of the other outcomes of the methods as described herein.

The cells and compositions may be administered using standard administration techniques, formulations, and/or devices. Administration of the cells can be autologous or allogeneic. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. Parenteral infusions may include intramuscular, intravenous, intraarterial, intraperitoneal, intrathoracic, intracranial, and/or subcutaneous administration. In some embodiments, a given dose is administered by a single bolus administration of the cells. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

B. Therapeutic and Prophylactic Methods and Uses

Provided are methods of treating a disease or condition in a subject using the provided polynucleotides, cassettes, vectors, cells containing the same, proteins and other molecules encoded thereby, and compositions thereof, such as those in which the recombinant or heterologous molecule encoded by the nucleic acid is a recombinant receptor, such as an antigen receptor, e.g. a CAR or a TCR. In some embodiments, the provided methods include administering to a subject having a disease or condition the provided cells or populations of cells, or pharmaceutical compositions thereof, that have been engineered to express a recombinant protein by transduction methods employing any of the provided vectors or viral particles containing the same. Also provided are uses and compositions for use in treating a disease or condition in a subject employing the provided cells or populations of cells, or compositions thereof, engineered to contain a recombinant receptor, such as an antigen receptor, e.g. a CAR or a TCR.

In some embodiments, the disease or condition treated or prevented is a cancer, an autoimmune disorder, and/or an infectious disease, such as a viral disease, and/or is one or more other diseases, conditions, and/or disorders.

In some embodiments, the cells, compositions, and/or polynucleotides, e.g., vectors, are administered to a subject or patient having the particular disease or condition to be treated, e.g., via adoptive cell therapy, such as adoptive T cell therapy. In some embodiments, cells and compositions prepared by the provided methods, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

In the provided methods or uses, the recombinant or heterologous protein may comprise a recombinant receptor, such as an antigen receptor, e.g. a CAR or a TCR, that specifically binds to a ligand expressed by the disease or condition or a cell or tissue thereof. For example, in some embodiments, the receptor is an antigen receptor and the ligand is an antigen specific for and/or associated with the disease or condition.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The subject, e.g., patient, to whom the cells, cell populations, or compositions are administered is a mammal, and typically is a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

Among the diseases, conditions, and disorders are tumors, including solid tumors, hematologic malignancies, and melanomas, and infectious diseases, such as infection with a virus or other pathogen, e.g., HIV, HCV, HBV, HPV, CMV, and parasitic disease. In some embodiments, the disease or condition is a tumor, cancer, malignancy, neoplasm, or other proliferative disease. Such diseases include but are not limited to leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin (including melanoma), bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

As used herein, a "post-transcriptional regulatory element (PRE)," such as a hepatitis PRE, refers to a DNA sequence that, when transcribed creates a tertiary structure capable of exhibiting post-transcriptional activity to enhance or promote expression of an associated gene operably linked thereto.

As used herein, "post-transcriptional activity" refers to activity of a regulatory element to control or regulate gene expression at the RNA level. Post-transcriptional activity can be manifested by activity that promotes RNA export from the nucleus, provides binding sites for cellular proteins, increases the total amount of RNA, e.g. recombinant and/or heterologous RNA, transcripts, increases RNA stability, increases the number of poly-adenylated transcripts and/or augments the size of the poly-adenylated tails in such transcripts.

As used herein "operably linked" refers to the association of components, such as a DNA sequence, e.g. a heterologous nucleic acid) and a regulatory sequence(s), in such a way as to permit gene expression when the appropriate molecules (e.g. transcriptional activator proteins) are bound to the regulatory sequence. Hence, it means that the components described are in a relationship permitting them to function in their intended manner.

As used herein, "unmodified" with reference to a PRE, an X gene or a Flap sequence refers to a starting polynucleotide that is selected for modification as provided. The starting polynucleotide can be a naturally-occurring, wild-type form of a polynucleotide. In some embodiments, the starting polynucleotide can be altered or mutated, such that it differs from a native wild-type form but is nonetheless referred to as a starting unmodified polynucleotide relative to the subsequently modified polynucleotides as provided. An unmodified polynucleotide does not contain a provided modification (e.g. stop codon, degradation sequence or deletion of all or a portion of a cPPT or CTS as provided) in its sequence. In some embodiments, the unmodified nucleic acid, e.g., PRE, is one that is known to possess or exhibit a desired degree of functionality or activity, such as a PRE with a known degree of post-transcriptional activity, e.g., ability to enhance gene expression. Exemplary of an unmodified PRE sequences are those set forth in SEQ ID NOS:1, 12-27, 119, 120, 125 or 216. Exemplary of an unmodified Flap sequence is set forth in SEQ ID NOS: 121.

As used herein, "wild-type" with reference to a PRE or an X gene refers to a sequence derived from a naturally occurring nucleic acid sequence of a PRE or an X gene that is present as such in a virus or virus genome, such as a hepadnavirus, e.g. an orthohepandanvirus, such as a hepadnavirus isolated from a mammal, in nature. Reference to wild-type without reference to a species is intended to encompass a virus sequence that includes an X gene isolated from any species. Exemplary of a wild-type PRE or X gene are any having a nucleic acid sequence obtained from or that has a sequence that is the same as a PRE or X gene sequence present in a hepadnavirus, including any hepadnavirus found or isolated from a mammalian species, such as a human, a primate, or a squirrel, for example a woodchuck. Examples of a wild-type PRE are those set forth in SEQ ID NOS:1, 12-27 or 125.

As used herein, "wild-type" with reference to a Flap sequence refers to a sequence derived from a naturally occurring viral nucleic acid sequence that contains cPPT and CTS regions for forming a DNA Flap present as such in a virus or virus genome, such as a retrovirus, e.g. a lentivirus, such as HIV-1. Exemplary of a wild-type Flap sequence are any having a nucleic acid sequence obtained from or that has a sequence that is the same as a viral nucleic acid sequence containing cPPT and CTS regions present in a retrovirus, including a lentivirus (e.g. HIV-1). Exemplary of viral nucleic acid containing a wild-type DNA Flap sequence is set forth in SEQ ID NOS:121.

As used herein, "percent (%) sequence identity" and "percent identity" when used with respect to a nucleotide sequence (reference nucleotide sequence) is defined as the percentage of nucleotide residues in a candidate sequence (e.g., the subject PRE or X gene, such as a modified PRE or variant X gene) that are identical with the nucleotide residues in the reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, "at a position corresponding to" or recitation that nucleotides, amino acid positions or regions "correspond to" nucleotides, amino acid positions or regions in a disclosed sequence, such as set forth in the Sequence listing, refers to positions of nucleotides or amino acids or a region or domain containing nucleotides or amino acids identified upon alignment with the disclosed sequence to maximize identity using a standard alignment algorithm, such as the GAP algorithm. Exemplary described corresponding residues or regions can be identified by alignment of a sequence with an exemplary PRE sequence set forth in SEQ ID NO:1 (or SEQ ID NO:125, which is residues 1-589 of SEQ ID NO:1). By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073). FIG. 2A to 2E exemplifies exemplary alignments and identification of exemplary corresponding residues.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section heading used herein are for organizational purposes only and are not to be construed as limiting the subject matter described.

III. Exemplary Embodiments

Among the embodiments provided herein are:
1. A polynucleotide, comprising:
a nucleic acid encoding a recombinant protein;
a modified post-transcriptional regulatory element (PRE) operably linked to said nucleic acid, said modified PRE comprising a variant of a wild-type or unmodified hepatitis virus X gene, said variant X gene comprising a stop codon not present in the wild-type or unmodified X gene.
2. The polynucleotide of embodiment 1, wherein the stop codon comprises at least one stop codon selected from among:
a stop codon beginning at a position within 36 or 24 nucleotides in the 3' direction from a position in the variant X gene corresponding to the 5' position of a start codon of the wild-type X protein open reading frame; and/or
a stop codon beginning at a position within 36 or 24 nucleotides in the 3' direction from a position corresponding to residue 411 of WHV post-transcriptional regulatory element (WPRE) sequence set forth in SEQ ID NO: 1 or SEQ ID NO:125 and/or residue 1503 of the WHV sequence set forth as SEQ ID NO: 2.
3. The polynucleotide of embodiment 1 or embodiment 2, wherein said variant X gene does not comprise an open reading frame of greater than at or about 39 nucleotides in length or greater than at or about 27 nucleotides in length.
4. A polynucleotide, comprising a modified post-transcriptional regulatory element (PRE), said modified PRE comprising a variant of a wild-type or unmodified hepatitis virus X gene, said variant X gene comprising a stop codon not present in the wild-type or unmodified X gene, wherein the stop codon comprises at least one stop codon selected from among:
a stop codon beginning at a position within 32 or 30 nucleotides in the 3' direction from a position in the variant X gene corresponding to the 5' position of a start codon of the wild-type X protein open reading frame; and/or
a stop codon beginning at a position within 32 or 30 nucleotides in the 3' direction from a position in the variant X gene corresponding to residue 411 of WHV post-transcriptional regulatory element (WPRE) sequence set forth in SEQ ID NO: 1 or SEQ ID NO:125 and/or residue 1503 of the WHV sequence set forth as SEQ ID NO: 2.
5. The polynucleotide of embodiment 4, wherein said variant X gene comprises an open reading frame of less than or equal to 33 nucleotides in length.
6. The polynucleotide of any of embodiments 1-5, wherein said stop codon comprises a plurality of stop codons.
7. The polynucleotide of embodiment 6, wherein said plurality of stop codons comprises at least one stop codon in each reading frame present in said variant X gene and/or comprises at least two stop codons in the same reading frame.
8. A polynucleotide, comprising a modified post-transcriptional regulatory element (PRE), said modified PRE comprising a variant of a wild-type or unmodified hepatitis virus X gene, said variant X gene comprising a plurality of stop codons not present in the wild-type or unmodified X gene.
9. The polynucleotide of embodiment 8, wherein the plurality of stop codons comprises at least one stop codon selected from among:
a stop codon beginning at a position within 36, 30 or 24 nucleotides in the 3' direction from a position in the variant X gene corresponding to the 5' position of a start codon of the wild-type X protein open reading frame; and/or
a stop codon beginning at a position within 36, 30 or 24 nucleotides in the 3' direction from a position in the variant X gene corresponding to residue 411 of WHV post-transcriptional regulatory element (WPRE) sequence set forth in SEQ ID NO: 1 or SEQ ID NO:125 and/or residue 1503 of the WHV sequence set forth as SEQ ID NO: 2.
10. The polynucleotide of embodiment 9, wherein said variant X gene does not comprise an open reading frame of greater than at or about 39 nucleotides in length, greater than at or about 33 nucleotides in length or greater than at or about 27 nucleotides in length.
11. The polynucleotide of any of embodiments 8-10, wherein the variant X gene comprises at least 2 stop codons, at least 3 stop codons or at least 4 stop codons.

12. The polynucleotide of any of embodiments 8-11, wherein the variant X gene comprises a stop codon in each reading frame present in said variant X gene.

13. The polynucleotide of any of embodiments 4-12, further comprising a nucleic acid encoding a recombinant protein operably linked to the modified PRE.

14. The polynucleotide of any of embodiments 1-13, wherein the stop codon comprises at least one stop codon selected from among:

a stop codon beginning at a position within or within at least 9, 12, 15, or 18 nucleotides in the 3' direction from a position in the variant X gene corresponding to the 5' position of a start codon of the wild-type or unmodified X protein open reading frame; and/or a stop codon beginning at a position within or within at least 9, 12, 15, or 18 nucleotides in the 3' direction from a position in the variant X gene corresponding to residue 411 of WHV post-transcriptional regulatory element (WPRE) sequence set forth in SEQ ID NO: 1 and/or residue 1503 of the WHV sequence set forth as SEQ ID NO: 2.

15. The polynucleotide of embodiment 14, wherein said variant X gene does not comprise an open reading frame of greater than at or about 21 nucleotides in length, greater than at or about 18 nucleotides in length, greater than at or about 15 nucleotides in length, or greater than at or about 12 nucleotides in length.

16. The polynucleotide of any of embodiments 1-15, wherein:

the modified PRE contains a beta stem loop corresponding to nucleotide residues 448-470 of SEQ ID NO:1 or SEQ ID NO:125; and/or the modified PRE does not contain a nucleotide change in a position within the beta stem loop corresponding to nucleotides 448-470 of SEQ ID NO:1 or SEQ ID NO:125; and/or said stop codon or stop codons does not comprise a nucleotide in a position within the beta stem loop corresponding to nucleotides 448-470 of SEQ ID NO:1 or SEQ ID NO:125.

17. The polynucleotide of any of embodiments 1-16, wherein said stop codon is selected from an amber (TAG), ochre (TAA), or opal (TGA) stop codons.

18. The polynucleotide of any of embodiments 1-17, wherein said stop codon is introduced by nucleotide substitution, deletion or insertion.

19. The polynucleotide of any of embodiments 1-18, wherein said stop codon is selected from among:

a stop codon beginning at position 9 in the 3' direction from a position in the variant X gene corresponding to the 5' position of a start codon of the wild-type or unmodified X protein open reading frame and/or at a nucleotide position corresponding to position 420 in the sequence set forth in SEQ ID NO:1 or SEQ ID NO:125;

a stop codon beginning at position 13 in the 3' direction from a position in the variant X gene corresponding to the 5' position of a start codon of the wild-type or unmodified X protein open reading frame and/or at a nucleotide position corresponding to position 424 in the sequence set forth in SEQ ID NO:1 of SEQ ID NO:125;

a stop codon beginning at position 17 in the 3' direction from a position in the variant X gene corresponding to the 5' position of a start codon of the wild-type or unmodified X protein open reading frame and/or at a nucleotide position corresponding to position 428 in the sequence set forth in SEQ ID NO:1 of SEQ ID NO:125;

a stop codon beginning at position 21 in the 3' direction from a position in the variant X gene corresponding to the 5' position of a start codon of the wild-type or unmodified X protein open reading frame and/or at a nucleotide position corresponding to position 432 in the sequence set forth in SEQ ID NO:1 of SEQ ID NO:125.

20. The polynucleotide of any of embodiments 17-19, wherein said stop codon is an amber (TAG) or opal (TGA) stop codon.

21. The polynucleotide of any of embodiments 1-20, wherein:

said variant X gene is no more than 180 nucleotides in length or is no more than at or about 210 nucleotides in length; and/or said variant X gene is at least at or about 90 nucleotides in length or at least about 120 nucleotides in length or is at least at or about 180 nucleotides in length.

22. The polynucleotide of any of embodiments 1-21, wherein:

said variant X gene is a variant of a wild-type or unmodified mammalian hepatitis X gene or a truncated portion thereof, which is, optionally, a truncated portion present in a PRE; or the modified PRE comprises a variant X gene comprising SEQ ID NO:28.

23. The polynucleotide of embodiment 22, wherein said wild-type or unmodified mammalian hepatitis X gene is a wild-type woodchuck hepatitis virus (WHV) X gene or a truncated portion thereof, which is optionally, a truncated portion present in a wild-type or unmodified PRE.

24. The polynucleotide of embodiment 23, wherein the wild-type or unmodified WHV X gene or the truncated portion of a wild-type X gene present in a PRE comprises the sequence of nucleotides set forth as nucleotides 411-592 of any of SEQ ID NOS: 1 and 12-20 or set forth as nucleotides 411-589 of SEQ ID NO:125.

25. The polynucleotide of embodiment 23 or embodiment 24, wherein said wild-type WHV X gene comprises the nucleotide sequence of SEQ ID NO: 9 or is a truncated portion thereof, which is, optionally, set forth in SEQ ID NO:10 or is a truncated portion present in a wild-type or unmodified PRE.

26. The polynucleotide of any of embodiments 1-25, wherein said modified PRE comprises at least two or at least three cis-acting post-transcriptional regulatory subelements of a wild-type or unmodified hepatitis virus PRE or functional variant(s) thereof.

27. The polynucleotide of embodiment 26, wherein said at least two or at least three subelements comprise a wild-type or unmodified PRE alpha subelement or functional variant thereof, a functional variant of a wild-type or unmodified PRE beta subelement, and/or a wild-type or unmodified PRE gamma subelement or functional variant thereof.

28. The polynucleotide of any of embodiments 1-27, wherein said modified PRE comprises an alpha subelement of a wild-type or unmodified hepatitis virus PRE or functional variant thereof and a functional variant of a wild-type or unmodified PRE beta subelement.

29. The polynucleotide of embodiment 27 or embodiment 28, wherein said alpha subelement comprises the sequence of SEQ ID NO: 3 or a variant thereof, said beta subelement comprises a variant of the sequence of SEQ ID NO: 6, and/or said gamma subunit comprises the sequence of SEQ ID NO: 8 or variant thereof.

30. The polynucleotide of any of embodiments 1-29, wherein the modified PRE comprises nucleotide modifications compared to a wild-type or unmodified hepatitis virus PRE that is a wild-type mammalian hepatitis PRE.

31. The polynucleotide of embodiment 30, wherein said wild-type or unmodified mammalian hepatitis virus PRE comprises the sequence of nucleotides set forth in any of SEQ ID NOS: 1, 12-27 and 125.

32. The polynucleotide of embodiment 30 or embodiment 31, wherein said wild-type or unmodified mammalian hepatitis PRE is a wild-type woodchuck hepatitis virus PRE (WPRE).

33. The polynucleotide of any of embodiments 1-32, wherein the wild-type or unmodified hepatitis PRE comprises:

a) the sequence of nucleotides set forth in SEQ ID NO:1 or SEQ ID NO:125 or a sequence of nucleotides that exhibits at least 94% sequence identity to SEQ ID NO:1 or SEQ ID NO:125, that exhibits substantially the same, such as at least 85%, 86%, 87%, 88%, 89%, 90%, 91%, 92%, 93%, 94%, 95%, 96%, 97%, 98% or 99% of the, post-transcriptional activity of SEQ ID NO:1 or SEQ ID NO:125; and b) a modified PRE comprising a portion of the sequence of nucleotides of a), wherein the portion exhibits or retains the post-transcriptional activity.

34. The polynucleotide of embodiment 33, wherein the wild-type or unmodified hepatitis PRE comprises a sequence of nucleotides that exhibits at least 95%, 96%, 97%, 98%, 99%, sequence identity to SEQ ID NO:1 or SEQ ID NO:125.

35. The polynucleotide of any of embodiments 1-34, wherein said wild-type or unmodified hepatitis PRE comprises the sequence of nucleotides set forth in any of SEQ ID NOS: 1, 12-20 and 125.

36. The polynucleotide of any of embodiments 1-35, wherein said wild-type or unmodified hepatitis PRE comprises the nucleotide sequence of SEQ ID NO: 1 or SEQ ID NO:125.

37. The polynucleotide of any of embodiments 1-36, wherein said variant X gene comprises a start codon beginning at a position corresponding to position 411 of SEQ ID NO: 1 or SEQ ID NO:125.

38. The polynucleotide of embodiment 37, wherein said start codon is an ATG start codon.

39. The polynucleotide of any of embodiments 1-38, wherein the variant X gene further comprises a promoter operably linked to said variant X gene.

40. The polynucleotide of embodiment 39, wherein said promoter is a wild-type or unmodified X-gene promoter comprising the sequence set forth in SEQ ID NO: 11 or a wild-type WHV X gene promoter sequence.

41. The polynucleotide of any of embodiments 1-40, wherein the modified PRE is selected from among:

a) a modified PRE comprising a sequence of nucleotides that exhibits at least 65% sequence identity to SEQ ID NO:1 or SEQ ID NO:125, said modified PRE containing a variant X gene comprising at least one stop codon not present in SEQ ID NO:1 or SEQ ID NO:125; and b) a modified PRE comprising a portion of the sequence of nucleotides of a), said portion comprising a variant X gene comprising the at least one stop codon, wherein the portion exhibits post-transcriptional activity.

42. The polynucleotide of embodiment 41, wherein the modified PRE comprises a sequence of nucleotides that exhibits at least 70%, 75%, 80%, 85%, 86%, 87%, 88%, 89%, 90%, 91%, 92%, 93%, 94%, 95%, 96%, 97%, 98% or 99%, sequence identity to SEQ ID NO:1 or SEQ ID NO:125.

43. The polynucleotide of embodiment 41 or embodiment 42, wherein the variant X gene comprises at least 2 stop codons, at least 3 stop codons or at least 4 stop codons.

44. The polynucleotide of any of embodiments 41-43, wherein the variant X gene comprises a stop codon in each reading frame present in said variant X gene.

45. The polynucleotide of any of embodiments 1-44, wherein the variant X gene comprises the sequence of nucleotides set forth in any of SEQ ID NOS: 44-58 or SEQ ID NOS: 141-155 and/or the modified PRE comprises the sequence of nucleotides set forth in any of SEQ ID NOS: 29-43 or SEQ ID NOS: 126-140.

46. The polynucleotide of any of embodiments 1-45, wherein the modified PRE does not contain any modifications in addition to the at least one stop codon not present in the wild-type or unmodified PRE.

47. The polynucleotide of any of embodiments 1-46, wherein the modified PRE contains additional modifications in addition to the at least one stop codon not present in the wild-type or unmodified PRE.

48. The polynucleotide of any of embodiments 1-47, wherein said variant X gene further comprises a variant of a start codon comprising one or more nucleotide differences compared to a wild-type or unmodified hepatitis virus X gene start codon and/or compared to the start codon corresponding to nucleotide positions 411-413 of SEQ ID NO: 1 or SEQ ID NO:125.

49. The polynucleotide of embodiment 48, wherein said one or more differences results in restricted or prevented translation initiation from said start codon.

50. The polynucleotide of any of embodiments 47-49, wherein said variant X gene comprises the sequence of nucleotides set forth in any of SEQ ID NOS: 74-88 or 171-185 and/or the modified PRE comprises the sequence of nucleotides set forth in any of SEQ ID NOS:59-73 or 156-170.

51. The polynucleotide of any of embodiments 1-50, wherein said variant X gene comprises a variant promoter operably linked to said variant X gene, said variant promoter comprising one or more nucleotide differences compared to a wild-type or unmodified hepatitis virus X gene promoter and/or compared to a promoter of SEQ ID NO: 11.

52. The polynucleotide of embodiment 51, wherein said one or more differences results in restricted or prevention of transcription from said promoter.

53. The polynucleotide of embodiment 51 or 52, wherein said modified PRE comprises the sequence of nucleotides set forth in any of SEQ ID NOS: 89-118 or 186-215.

54. The polynucleotide of any of embodiments 1-53, wherein upon introduction into a eukaryotic cell, no polypeptide of a length greater than 12, 11, 10, 9, or 8 amino acids in length encoded by said variant X gene is produced; and/or said polynucleotide is incapable of producing a polypeptide of a length greater than 12, 11, 10, 9, or 8 amino acids in length encoded by said variant X gene.

55. The polynucleotide of any of embodiments 1-54, wherein said modified PRE encodes an RNA that promotes nuclear RNA export and/or increases mRNA stability.

56. The polynucleotide of any of embodiments 1-55, wherein said modified PRE encodes an RNA polynucleotide that promotes nuclear RNA export and/or increases mRNA stability, wherein said promotion of nuclear RNA export and/or mRNA stability increases expression of the recombinant protein.

57. The polynucleotide of any of embodiments 1-56, wherein the modified PRE retains the post-transcriptional activity of the corresponding wild-type or unmodified hepatitis PRE and/or the PRE set forth in SEQ ID NO:1, SEQ ID NO:119, SEQ ID NO:120, SEQ ID NO:125 and/or SEQ ID NO:216, which, in some cases, is at least or about at least 65%, 70%, 75%, 80%, 85%, 90% or 95% of the post-transcriptional activity of the wild-type or unmodified hepatitis PRE and/or the PRE set forth in SEQ ID NO:1, SEQ ID NO:119, SEQ ID NO:120, SEQ ID NO:125 or SEQ ID NO:216.

58. The polynucleotide of any of embodiments 1-57, wherein the variant X gene further comprises a sequence encoding a post-translational modification signal not present in the wild-type or unmodified hepatitis virus X gene.

59. A polynucleotide, comprising a modified post-transcriptional regulatory element (PRE), said modified PRE comprising a variant of a wild-type or unmodified hepatitis virus X gene, said variant X gene comprising a sequence encoding a post-translational modification signal not present in the wild-type or unmodified hepatitis virus X gene.

60. The polynucleotide of embodiment 58 or embodiment 59, wherein said post-translational modification signal comprises a ubiquitination site.

61. The polynucleotide of embodiment 58 or embodiment 59, wherein said post-translational modification signal comprises:

a first codon beginning at a position within or within at least 2, 3, 4, 5 or 6 nucleotides in the 3' direction from a position in the variant X gene corresponding to the 5' position of a start codon of the X protein open reading frame, wherein the first codon encodes a glycine, arginine, glutamic acid, phenylalanine, aspartate, cysteine, lysine, asparagine, serine, tyrosine, tryptophan, histidine, or leucine residue according to the N-end rule; and optionally a second codon beginning at a position within or within at least 2, 3, 4, 5 or 6 nucleotides in the 3' direction from a position in the variant X gene corresponding to the 5' position of a start codon of the X protein open reading frame, wherein the second codon encodes a glutamic acid or asparagine residue according to the N-end rule.

62. The polynucleotide of embodiment 58 or embodiment 59, wherein said post-translational modification signal comprises one or more PEST sequences.

63. The polynucleotide of any of embodiments 59-62, further comprising a nucleic acid encoding a recombinant or protein operably linked to the modified PRE.

64. The polynucleotide of any of embodiments 59-63, wherein:

said variant X gene comprising a sequence encoding a post-translational modification signal contains a beta stem loop corresponding to nucleotide residues 448-470 of SEQ ID NO:1; and/or said variant X gene comprising a sequence encoding a post-translational modification signal does not contain a nucleotide change in a position within the beta stem loop corresponding to nucleotides 448-470 of SEQ ID NO:1.

65. The polynucleotide of any of embodiments 59-64, wherein:

said variant X gene is no more than 180 nucleotides in length or is no more than at or about 210 nucleotides in length; and/or said variant X gene is at least at or about 90 nucleotides in length or at least about 120 nucleotides in length or is at least at or about 180 nucleotides in length.

66. The polynucleotide of any of embodiments 59-65, wherein said variant X gene is a variant of a wild-type or unmodified mammalian hepatitis X gene or a truncated portion thereof, which is, optionally, a truncated portion present in a PRE.

67. The polynucleotide of embodiment 66, wherein said wild-type or unmodified mammalian hepatitis X gene is a wild-type woodchuck hepatitis virus (WHV) X gene or a truncated portion thereof, which is optionally, a truncated portion present in a wild-type or unmodified PRE.

68. The polynucleotide of embodiment 67, wherein the wild-type or unmodified WHV X gene or the truncated portion of a wild-type X gene present in a PRE comprises the sequence of nucleotides set forth as nucleotides 1503-1928 of SEQ ID NO: 2, the sequence of nucleotides set forth as nucleotides 411-592 of any of SEQ ID NOS: 1 and 12-20 or the sequence of nucleotides set forth as nucleotides 411-589 of SEQ ID NO:125.

69. The polynucleotide of embodiment 67 or embodiment 68, wherein said wild-type WHV X gene comprises the nucleotide sequence of SEQ ID NO: 9 or is a truncated portion thereof, which is, optionally, set forth in SEQ ID NO:10 or is a truncated portion present in a wild-type or unmodified PRE.

70. The polynucleotide of any of embodiments 59-69, wherein said modified PRE comprises at least two or at least three cis-acting post-transcriptional regulatory subelements of a wild-type or unmodified hepatitis virus PRE or functional variant(s) thereof.

71. The polynucleotide of embodiment 70, wherein said at least two or at least three subelements comprise a wild-type or unmodified PRE alpha subelement or functional variant thereof, a functional variant of a wild-type or unmodified PRE beta subelement, and/or a wild-type or unmodified PRE gamma subelement or functional variant thereof.

72. The polynucleotide of any of embodiments 59-71, wherein said modified PRE comprises an alpha subelement of a wild-type or unmodified hepatitis virus PRE or functional variant thereof and a functional variant of a wild-type or unmodified PRE beta subelement.

73. The polynucleotide of embodiment 71 or embodiment 72, wherein said alpha subelement comprises the sequence of SEQ ID NO: 3 or a variant thereof, said beta subelement comprises a variant of the sequence of SEQ ID NO: 6, and/or said gamma subunit comprises the sequence of SEQ ID NO: 8 or variant thereof.

74. The polynucleotide of any of embodiments 1-73, wherein the modified PRE comprises nucleotide modifications compared to a wild-type or unmodified hepatitis virus PRE that is a wild-type mammalian hepatitis PRE.

75. The polynucleotide of embodiment 74, wherein said wild-type or unmodified mammalian hepatitis virus PRE comprises the sequence of nucleotides set forth in any of SEQ ID NOS: 1, 12-27 and 125.

76. The polynucleotide of embodiment 74 or embodiment 75, wherein said wild-type or unmodified mammalian hepatitis PRE is a wild-type woodchuck hepatitis virus PRE (WPRE).

77. The polynucleotide of any of embodiments 1-76, wherein the wild-type or unmodified hepatitis PRE comprises:

a) the sequence of nucleotides set forth in SEQ ID NO:1 or SEQ ID NO:125 or a sequence of nucleotides that exhibits at least 94% sequence identity to SEQ ID NO:1 or SEQ ID NO:125 that exhibits substantially the same, such as at least 85%, 86%, 87%, 88%, 89%, 90%, 91%, 92%, 93%, 94%, 95%, 96%, 97%, 98% or 99% of the, post-transcriptional activity of SEQ ID NO:1 or SEQ ID NO:125; and b) a modified PRE comprising a portion of the sequence of nucleotides of a), wherein the portion exhibits or retains the post-transcriptional activity.

78. The polynucleotide of embodiment 77, wherein the wild-type or unmodified hepatitis PRE comprises a sequence of nucleotides that exhibits at least 95%, 96%, 97%, 98%, 99%, sequence identity to SEQ ID NO:1 or SEQ ID NO:125.

79. The polynucleotide of any of embodiments 59-78, wherein said wild-type or unmodified hepatitis PRE comprises the sequence of nucleotides set forth in any of SEQ ID NOS: 1, 12-20 and 125.

80. The polynucleotide of any of embodiments 59-79, wherein said wild-type or unmodified hepatitis PRE comprises the nucleotide sequence of SEQ ID NO: 1 or SEQ ID NO:125.

81. The polynucleotide of any of embodiments 59-80, wherein said variant X gene comprises a start codon beginning at a position corresponding to position 411 of SEQ ID NO: 1 or SEQ ID NO:125.

82. The polynucleotide of embodiment 81, wherein said start codon is an ATG start codon.

83. The polynucleotide of any of embodiments 59-82, wherein the variant X gene further comprises a promoter operably linked to said variant X gene.

84. The polynucleotide of embodiment 83, wherein said promoter is a wild-type or unmodified X-gene promoter comprising the sequence set forth in SEQ ID NO: 11 or a wild-type WHV X gene promoter sequence.

85. The polynucleotide of any of embodiments 59-84, wherein the modified PRE is selected from among:
a) a modified PRE comprising a sequence of nucleotides that exhibits at least 65% sequence identity to SEQ ID NO:1 or SEQ ID NO:125, said modified PRE containing a variant X gene comprising a sequence encoding a post-translational modification signal not present in SEQ ID NO:1 or SEQ ID NO:125; and
b) a modified PRE comprising a portion of the sequence of nucleotides of a), said portion comprising a variant X gene comprising the sequence encoding a post-translational modification, wherein the portion exhibits post-transcriptional activity.

86. The polynucleotide of embodiment 85, wherein the modified PRE comprises a sequence of nucleotides that exhibits at least 70%, 75%, 80%, 85%, 86%, 87%, 88%, 89%, 90%, 91%, 92%, 93%, 94%, 95%, 96%, 97%, 98% or 99%, sequence identity to SEQ ID NO:1 or SEQ ID NO:125.

87. The polynucleotide of any of embodiments 1-86, wherein the variant X gene comprises up to 1, 2, 3, 4, 5, 6, 7, 8, 9, 10, 11 or 12 nucleotide changes.

88. The polynucleotide of any of embodiments 59-87, wherein the modified PRE does not contain any modifications in addition to the sequence encoding a post-translational modification signal.

89. The polynucleotide of any of embodiments 59-88, wherein the modified PRE contains additional modification(s) in addition to the sequence encoding a post-translational modification signal not present in the wild-type or unmodified hepatitis virus X gene.

90. The polynucleotide of embodiment 89, wherein the additional modification(s) are in the variant X gene.

91. The polynucleotide of embodiment 90, wherein the additional modification(s) results in a variant X gene encoding an inactive X protein and/or a truncated X protein.

92. The polynucleotide of any of embodiments 59-91, wherein said modified PRE encodes an RNA that promotes nuclear RNA export and/or increases mRNA stability.

93. The polynucleotide of any of embodiments 59-92, wherein said modified PRE encodes an RNA polynucleotide that promotes nuclear RNA export and/or increases mRNA stability, wherein said promotion of nuclear RNA export and/or mRNA stability increases expression of the recombinant protein.

94. The polynucleotide of any of embodiments 59-93, wherein the modified PRE retains the post-transcriptional activity of the corresponding wild-type or unmodified hepatitis PRE and/or the PRE set forth in SEQ ID NO:1, SEQ ID NO:119, SEQ ID NO:120, SEQ ID NO:125 and/or SEQ ID NO:216, which, in some cases, is at least or about at least 65%, 70%, 75%, 80%, 85%, 90% or 95% of the post-transcriptional activity of the wild-type or unmodified hepatitis PRE and/or the PRE set forth in SEQ ID NO:1, SEQ ID NO:119, SEQ ID NO:120, SEQ ID NO:125 or SEQ ID NO:216.

95. A polynucleotide, comprising a viral nucleic acid comprising a variant Flap, wherein the variant Flap contains a deletion of all or a portion of the nucleotides corresponding to the central polypurine tract (cPPT) and/or the central termination sequence (CTS) regions of a wild-type or unmodified Flap sequence.

96. The polynucleotide of embodiment 95, wherein the variant Flap comprises a deletion of all or a portion, which can be a contiguous portion, of the nucleotides corresponding to the cPPT and the CTS.

97. The variant Flap polynucleotide of embodiment 95 or 96, wherein:
the wild-type or unmodified Flap sequence comprises from or from about 80 to 200 contiguous nucleotides comprising the cPPT or CTS regions of a retrovirus, which optionally is a lentivirus, which optionally is HIV-1; and/or
the wild-type or unmodified Flap sequence comprises a) the sequence of nucleotides set forth in SEQ ID NO:121; b) a sequence of nucleotides comprising at least 85%, 86%, 87%, 88%, 89%, 90%, 91%, 92%, 93%, 94%, 95%, 96%, 97%, 98% or 99% sequence identity to the sequence of nucleotides set forth in SEQ ID NO:121 that contains the cPPT and/or CTS regions; or c) a contiguous portion of a) or b) that comprises the cPPT and/or CTS regions.

98. The variant Flap polynucleotide of any of embodiments 95-97, wherein:
the variant Flap comprises deletion of all or a portion, which can be a contiguous portion, of nucleotides corresponding to nucleotides of the cPPT region set forth in SEQ ID NO: 123; and/or
the variant Flap comprises deletion of all or a portion, which can be a contiguous portion, of nucleotides corresponding to the CTS region set forth in SEQ ID NO: 124.

99. The variant Flap polynucleotide of any of embodiment 95-98, wherein the variant Flap comprises deletion of all or a portion, which can be a contiguous portion, of the cPPT region set forth in SEQ ID NO:123 and comprises deletion of all or a portion, which can be a contiguous portion, of the CTS region set forth in SEQ ID NO:124.

100. The variant Flap polynucleotide of any of embodiments 95-99, wherein:
the viral nucleic acid comprising the variant Flap comprises a sequence of nucleotides that exhibits at least 65%, 70%, 75%, 80%, 85%, or 90% sequence identity to SEQ ID NO:121, said variant Flap lacking all or a portion of the cPPT and/or CTS regions; and/or
the viral nucleic acid comprises the variant Flap comprising the sequence set forth in SEQ ID NO:122.

101. The polynucleotide of any of embodiments 1-94, further comprises a polynucleotide comprising viral nucleic acid comprising a variant Flap of any of embodiments 95-100.

102. A polynucleotide of any of embodiments 95-101, comprising:
a variant Flap comprising the sequence of SEQ ID NO: 122 or a sequence having at least at or about 90%, 95%, 96%, 97%, 98%, or 99% sequence identity to SEQ ID NO:122; and the sequence of SEQ ID NO:29 or SEQ ID NO:126 or a sequence having at least at or about 90%, 95%, 96%, 97%, 98%, or 99% sequence identity to SEQ ID NO:29 or SEQ ID NO:126; and optionally, comprising nucleic acid encoding a recombinant protein.

103. The polynucleotide of any of embodiments 1-94 and 101-102, wherein the recombinant protein comprises a recombinant receptor.

104. The polynucleotide of embodiment 103, wherein the recombinant receptor is an antigen receptor and/or a chimeric receptor.

105. The polynucleotide of embodiment 104, wherein the recombinant receptor is a functional non-TCR antigen receptor or a transgenic TCR.

106. The polynucleotide of any of embodiments 103-105, wherein the recombinant receptor is a chimeric antigen receptor (CAR).

107. An expression cassette comprising the polynucleotide of any of embodiments 1-106 and a promoter operably linked to the nucleic acid encoding the recombinant protein.

108. A vector comprising the polynucleotide of any of embodiments 1-106 or the expression cassette of embodiment 107.

109. The vector of embodiment 108, which is a viral vector.

110. The vector of embodiment 109, wherein the viral vector is a lentiviral vector, which, optionally, is derived from HIV-1.

111. The vector of embodiment 109, wherein the viral vector is a retroviral vector.

112. A cell comprising the expression cassette of embodiment 107 or the vector of any of embodiments 108-111.

113. The cell of embodiment 112, wherein the cell is a T cell, a natural killer (NK) cell, an iPS cell, or an iPS-derived cell.

114. A virus particle, comprising the vector of any of embodiments 108-111.

115. A method, comprising introducing the expression cassette of embodiment 107, the vector of any of embodiments 108-111, or the virus particle of embodiment 114 to a cell, under conditions whereby expression of the recombinant protein is effected in the cell.

116. The method of embodiment 115, wherein:

said introduction is effected by transducing said cell with said vector or viral particle;

said introduction is effected by transfecting said cell with said vector; and/or said introduction is effected by electroporation of said cell with said vector.

117. The method of embodiment 116, wherein the recombinant protein is expressed at a level that is increased compared to that achieved by introducing a vector that is the same but that does not contain the modified PRE or does not contain a PRE.

118. A cell produced by the method of any of embodiments 115-117.

119. A pharmaceutical composition comprising the cell of embodiments 112, 113, or 118, and a pharmaceutically effective carrier.

120. A method of treatment, the method comprising administering to a subject having a disease or condition the vector of any of embodiments 108-111, the virus particle of embodiment 114, the cell of embodiment 112, 113, or 118, or the composition of embodiment 119.

121. The method of embodiment 120, wherein the recombinant protein comprises a recombinant receptor that specifically binds to a ligand expressed by the disease or condition or a cell or tissue thereof.

122. The method of embodiment 121, wherein the receptor is an antigen receptor and the ligand is an antigen specific for and/or associated with the disease or condition.

123. The method of embodiment 122, wherein the disease or condition is a cancer, and autoimmune disorder, or an infectious disease.

124. Use of a pharmaceutical composition of embodiment 119 for treating a disease or condition.

125. A pharmaceutical composition of embodiment 119 for use in the preparation of a medicament for treating a disease or condition.

126. The use of embodiment 124 or the pharmaceutical composition of embodiment 125, wherein the recombinant protein expressed by the cell comprises a recombinant receptor that specifically binds to a ligand expressed by the disease or condition or a cell or tissue thereof.

127. The use or pharmaceutical composition of any of embodiments 124-126, wherein the recombinant receptor is an antigen receptor and the ligand is an antigen specific for and/or associated with the disease or condition.

128. The use or pharmaceutical composition of any of embodiments 124-127, wherein the disease or condition is a cancer, an autoimmune disorder or an infectious disease.

IV. Examples

The following examples are included for illustrative purposes only and are not intended to limit the scope of the invention.

Example 1

Modified Woodchuck Hepatitis Virus Post-Transcriptional Regulatory Element

An exemplary modified woodchuck hepatitis virus post-transcriptional regulatory element (WPRE) polynucleotide was generated, which contained modifications at residues corresponding to positions in an exemplary wild-type WPRE sequence (SEQ ID NO: 1). Stop codons were introduced into each reading frame corresponding to a region of SEQ ID NO: 1 encoding a truncated portion of the WHV X protein (X gene fragment). Specifically, within this region, two stop codons were introduced in the open reading frame encoding the truncated X protein (beginning 9 and 21 nucleotides from the site corresponding to the 5' position of the X gene start codon), and one in each of the other two reading frames (beginning 13 and 17 nucleotides from the site corresponding to the 5' position of the start codon). The modified WPRE contained the nucleotide sequence set forth in SEQ ID NO: 126. In the following portion of this sequence, the stop codons are set forth in bold, and introduced mutations with reference to SEQ ID NO:1 are underlined: ATGGCTGCTTAGCTGAGTAGCTGA (SEQ ID NO:28). A control functional modified WPRE, containing the sequence set forth in SEQ ID NO: 216, also was generated. This control functional modified WPRE contains mutations in the WHV X gene promoter region and start codon compared to the wild-type WPRE sequence of SEQ ID NO: 1. It has been used in a plurality of viral vectors for transduction, demonstrating activity sufficient to promote expression of recombinant molecules encoded by such vectors (see, e.g., "Cloning vector pLV.MCS.WHVPRE, complete sequence," GenBank: JN622008.1; U.S. Pat. No. 7,384,738).

The modified WPRE polynucleotide containing the nucleotide sequence set forth in SEQ ID NO: 126 and the control modified WPRE containing the nucleotide sequence set forth in SEQ ID NO: 216 each were separately incorporated into an exemplary HIV-1-derived lentiviral vector containing mutations within the viral Flap region. Specifically, the lentiviral vector contained a variant Flap region in which the regions corresponding to SEQ ID NO:123 and SEQ ID NO:124 were deleted, resulting in a Flap variant vector, having a portion containing the nucleotide sequence set forth in SEQ ID NO:122 (designated Flap −/−).

A lentiviral vector in which the control modified WPRE of SEQ ID NO:119 was incorporated into an exemplary HIV-1 derived lentiviral vector that contained a complete Flap region also was generated. The lentiviral vector containing the complete Flap region (a wild-type Flap polynucleotide) containing the nucleotide sequence set forth in SEQ ID NO:121 (designated Flap +/+).

Sequences contained in the generated lentiviral vectors are summarized in the Table 4 below:

TABLE 4

|  | WPRE (SEQ ID NO) | Flap REGION |
|---|---|---|
| Control modified WPRE, Flap+/+ | 216 | 121 |
| Control modified WPRE, Flap−/− | 216 | 122 |
| Modified WPRE, Flap−/− | 126 | 122 |

The vector contained polynucleotides encoding chimeric antigen receptor and truncated epidermal growth factor (EGFRt) transduction marker separated by a T2A linker (see U.S. Pat. No. 8,802,374). Pseudotyped lentiviral vector particles were produced by standard procedures by transiently transfecting HEK-293T cells with the resulting vectors, helper plasmids (containing gagpol plasmids and rev plasmid), and a pseudotyping plasmid and used to transduce cells.

Example 2

Transduction of Cells with Viral Vectors Containing Modified WPRE

The lentiviral vector particles described in Example 1 were used to transduce cells from a human fibrosarcoma cell line (HT1080 ATCC® No. CCL-121™) and primary human T cells. Transduction efficiency was assessed by measuring surface expression of the recombinant EGFRt marker encoded by the vector.

2A. HT1080 Cells

In duplicate studies (A and B), HT1080 cells were transduced in 24-well plates with 250 μL or 125 μL volume of virus in the presence of 8 μg/mL of Polybrene with spinoculation (1200×g for 30 minutes). A sample of untransduced cells was used as a negative control.

Following culture of the cells for 48-72 hours, surface expression of the EGFRt marker was detected by flow cytometry with gating set based on the untransduced control sample. EGFRt was detected using a biotin-conjugated anti-EGFR antibody (cetuximab) followed by detection with a secondary V450-conjugated streptavidin. Table 5 lists the percentage of live cells exhibiting surface EGFRt expression for each of the various conditions in duplicates A and B.

As shown, transduction of HT1080 cells using a lentiviral vector having a variant Flap region and a modified WPRE with stop codons in the X gene fragment resulted in comparable EGFRt expression to that using a vector with a variant Flap region and a control modified WPRE. Thus, as compared to modifications in the X gene start codon and promoter region, the presence of stop codons in the X gene fragment did not interfere with the ability of a WPRE to promote the expression of recombinant protein encoded by the vector.

Also, as shown, a lentiviral vector having a variant Flap region successfully transduced HT1080 cells as detected by EGFRt expression.

TABLE 5

| Virus | | Percentage of live cells expressing surface EGFRt | |
|---|---|---|---|
| WPRE in vector | (vol.) | A | B |
| Untransduced control | N/A | 0.3% | 0.1% |
| Modified WPRE, Flap−/− | 250 μL | 58.9% | 56.3% |
|  | 125 μL | 26.2% | 20.5% |
| Control modified WPRE, Flap−/− | 250 μL | 62.1% | 41.4% |
|  | 125 μL | 34.2% | 18.7% |
| Control modified WPRE, Flap+/+ | 250 μL | 81% | 56.7% |
|  | 125 μL | 56.9% | 48.4% |

2B. Human T Cells

Primary human T cells were enriched via positive selection from peripheral blood mononuclear cells (PBMCs) obtained from human apheresis samples. The cells were activated using anti-CD3/anti-CD28 beads in the presence IL-2 (100 IU/mL). Activated T cells were transduced with one volume of virus in the presence of Polybrene (8 μg/mL) and spinoculation (1200×g for 30 min) in 24-well plates for each of the vectors described in Example 1. A sample of untransduced cells served as a negative control.

Surface expression of EGFRt was detected as described above in Example 2A. The results are shown in Table 6, including results from duplicate studies (A and B). As shown, transduction of primary human T cells using a lentiviral vector having a variant Flap region and a modified WPRE with stop codons in the X gene fragment resulted in comparable EGFRt expression to that using a vector with a variant Flap region and a control modified WPRE. Thus, as compared to modifications in the X gene start codon and promoter region, the presence of stop codons in the X gene fragment did not interfere with the ability of a WPRE to promote the expression of recombinant protein encoded by the vector. These results were consistent across multiple activation reagents, as similar results were obtained when human primary T cells were activated with various types of anti-CD3/anti-CD28 beads.

Also, as shown, a lentiviral vector having a variant Flap region successfully transduced T cells as observed by EGFRt expression.

TABLE 6

|  | Percentage of live cells expressing surface EGFRt | |
|---|---|---|
| WPRE in vector | A | B |
| Untransduced | 0.1% | N/D |
| Modified WPRE, Flap−/− | 24.4% | 22.5% |

TABLE 6-continued

| WPRE in vector | Percentage of live cells expressing surface EGFRt | |
|---|---|---|
| | A | B |
| Control modified WPRE, Flap−/− | 20.9% | 25.8% |
| Control modified WPRE, Flap+/+ | 39.1% | N/D |

Example 3

Transduction of Cells with Viral Vectors Containing a Complete Flap or Variant Flap Region Lentiviral vector particles were generated substantially as described in Example 1 in which each encoded a chimeric antigen receptor (CAR) containing a different anti-CD19 scFv antigen-binding domain. Each lentiviral vector also contained WPRE polynucleotides of a control functional modified WPRE that was null for the X gene ORF operably linked to the polynucleotides encoding the CAR, and either a wildtype Flap polynucleotide (Flap +/+) (SEQ ID NO:121) or a variant Flap polynucleotide (Flap −/−) (SEQ ID NO:122). For detection of expression of the CAR, the lentiviral vectors also encoded a truncated EGFR (EGFRt) transduction marker separated from the CAR by a self-cleaving T2A linker.

Primary human CD8+ T cells were enriched via positive selection from peripheral blood mononuclear cells (PBMCs) obtained from human apheresis samples. The lentiviral vector particles were used to transduce CD8+ T cells (essentially as described by Yam et al. (2002) Mol. Ther. 5:479; WO2015/095895). A sample of untransduced cells served as a negative control.

After transduction and expansion, staining with anti-EGFR antibody was used to verify expression of the EGFRt transduction marker on the surface of T cells by flow cytometry as described in Example 2A. Gating was set based on the untransduced control sample. Table 7 lists the percentage of live cells exhibiting surface EGFRt expression for each of the various conditions. As shown, the results confirmed that lentiviral vectors with a Flap −/− polynucleotide could successfully transduce CD8+ T cells.

TABLE 7

| CAR No. | Percentage of live CD8+ cells expressing surface EGFRt | |
|---|---|---|
| | Flap+/+ | Flap−/− |
| 1 | 48% | 26% |
| 2 | 38% | 24% |
| 3 | 51% | 21% |
| 4 | 35% | 23% |
| 5 | 45% | 25% |
| 6 | 47% | 17% |
| 7 | 59% | 23% |
| 8 | 55% | 24% |
| 9 | 41% | 21% |
| 10 | 50% | 22% |
| 11 | 60% | 27% |

Following transduction, T cells transduced with each CAR construct, including those containing the variant Flap −/− polynucleotide, were successfully selectively enriched and expanded (at or close to 100% EGFRt+ as confirmed by flow cytometry) by stimulation in the presence of irradiated CD19+ cell lines.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A polynucleotide, comprising a modified post-transcriptional regulatory element (PRE), said modified PRE comprising a variant of a wild-type hepatitis virus X gene, said variant X gene comprising a plurality of stop codons not present in the wild-type X gene, wherein the variant X gene comprises a stop codon in each reading frame present in said variant X gene.

2. The polynucleotide of claim 1, further comprising a nucleic acid encoding a recombinant protein operably linked to the modified PRE.

3. A vector comprising the polynucleotide of claim 2.

4. A cell comprising the polynucleotide of claim 2.

5. A polynucleotide, comprising a modified post-transcriptional regulatory element (PRE), said modified PRE comprising a variant of a wild-type hepatitis virus X gene, said variant X gene comprising a plurality of stop codons not present in the wild-type X gene; and,
  a nucleic acid encoding a recombinant protein that is a recombinant receptor operably linked to the modified PRE.

6. The polynucleotide of claim 5, wherein the stop codon comprises at least one stop codon selected from among:
  a stop codon beginning at a position within or within at least 9, 12, 15, or 18 nucleotides in the 3' direction from a position in the variant X gene corresponding to the 5' position of a start codon of the X protein open reading frame; and/or
  a stop codon beginning at a position within or within at least 9, 12, 15, or 18 nucleotides in the 3' direction from a position in the variant X gene corresponding to residue 411 of WHV post-transcriptional regulatory element (WPRE) sequence set forth in SEQ ID NO: 1 and/or residue 1503 of the WHV sequence set forth as SEQ ID NO: 2.

7. The polynucleotide of claim 5, wherein the variant X gene further comprises a sequence encoding a post-translational modification signal not present in the wild-type hepatitis virus X gene.

8. The polynucleotide of claim 5, wherein said variant X gene is a variant of a wild-type mammalian hepatitis virus X gene.

9. The polynucleotide of claim 8, wherein said wild-type mammalian hepatitis virus X gene is a wild-type woodchuck hepatitis virus (WHV) X gene.

10. The polynucleotide of claim 5, wherein the modified PRE comprises nucleotide modifications compared to a wild-type or unmodified hepatitis virus PRE that is a mammalian hepatitis PRE.

11. The polynucleotide of claim 10, wherein said wild-type or unmodified mammalian hepatitis PRE is a wild-type woodchuck hepatitis virus PRE (WPRE).

12. The polynucleotide of claim 10, wherein the wild-type or unmodified hepatitis virus PRE comprises:
  a) the sequence of nucleotides set forth in SEQ ID NO:1 or 125 or a sequence of nucleotides that exhibits at least 94%, 95%, 96%, 97%, 98%, or 99% sequence identity to SEQ ID NO:1 or 125; or
  b) a portion of the sequence of nucleotides of a), wherein the portion exhibits post-transcriptional activity.

13. The polynucleotide of claim 5, wherein the modified PRE is selected from among:
  a) a modified PRE comprising a sequence of nucleotides that exhibits at least 95% sequence identity to SEQ ID NO:1 or 125, said modified PRE containing a variant X gene comprising at least one stop codon not present in SEQ ID NOS:1 or 125; and
  b) a modified PRE comprising a portion of the sequence of nucleotides of a), said portion comprising a variant X gene comprising the plurality of stop codons, wherein the portion exhibits post-transcriptional activity.

14. The polynucleotide of claim 5, wherein the variant X gene comprises the sequence of nucleotides set forth in any of SEQ ID NOS: 44-54 or 141-151 and/or the modified PRE comprises the sequence of nucleotides set forth in any of SEQ ID NOS:29-39 or 126-136.

15. The polynucleotide of claim 5, wherein said variant X gene further comprises a variant of a start codon comprising one or more nucleotide differences compared to a wild-type hepatitis virus X gene start codon and/or compared to the start codon corresponding to nucleotide positions 411-413 of SEQ ID NO: 1, wherein the one or more nucleotide differences results in restricted or prevented translation initiation from said start codon.

16. The polynucleotide of claim 5, wherein said variant X gene comprises a variant promoter operably linked to said variant X gene, said variant promoter comprising one or more nucleotide differences compared to a wild-type hepatitis virus X gene promoter and/or compared to a promoter of SEQ ID NO: 11, wherein said one or more differences results in restricted or prevention of transcription from said promoter.

17. The polynucleotide of claim 5, wherein:
  upon introduction into a eukaryotic cell, no polypeptide of a length greater than 12, 11, 10, 9, or 8 amino acids in length encoded by said variant X gene is produced; and/or
  said polynucleotide is incapable of producing a polypeptide of a length greater than 12, 11, 10, 9, or 8 amino acids in length encoded by said variant X gene.

18. The polynucleotide of claim 5, wherein the variant X gene comprises up to 1, 2, 3, 4, 5, 6, 7, 8, 9, 10, 11 or 12 nucleotide changes.

19. The polynucleotide of claim 5, wherein said modified PRE encodes an RNA that promotes nuclear RNA export and/or increases mRNA stability.

20. The polynucleotide of claim 5, further comprising a viral nucleic acid comprising a variant Flap, wherein the variant Flap contains a deletion of all or a portion of the nucleotides corresponding to the central polypurine tract (cPPT) and/or the central termination sequence (CTS) regions of a wild-type or unmodified Flap sequence.

21. The polynucleotide of claim 20, wherein the variant Flap comprises deletion of all or a contiguous portion of nucleotides corresponding to nucleotides in the cPPT region set forth in SEQ ID NO:123 and comprises deletion of all or a contiguous portion of nucleotides corresponding to nucleotides in the CTS region set forth in SEQ ID NO:124.

22. The polynucleotide of claim 20, comprising:
  a variant Flap comprising the sequence of SEQ ID NO: 122 or a sequence having at least at or about 90%, 95%, 96%, 97%, 98%, or 99% sequence identity to SEQ ID NO:122; and
  a modified PRE comprising the sequence of SEQ ID NO:29 or 126 or a sequence having at least at or about 90%, 95%, 96%, 97%, 98%, or 99% sequence identity to SEQ ID NO:29 or 126.

23. The polynucleotide of claim 5, wherein the recombinant receptor is an antigen receptor and/or a chimeric receptor.

24. An expression cassette comprising the polynucleotide of claim 5 and a promoter operably linked to the nucleic acid encoding the recombinant protein.

25. The polynucleotide of claim 5, wherein said stop codon is selected from among:
- a stop codon beginning at a nucleotide position corresponding to position 420 in the sequence set forth in SEQ ID NO:1;
- a stop codon beginning at a nucleotide position corresponding to position 424 in the sequence set forth in SEQ ID NO:1;
- a stop codon beginning at a nucleotide position corresponding to position 428 in the sequence set forth in SEQ ID NO:1; and
- a stop codon beginning at a nucleotide position corresponding to position 432 in the sequence set forth in SEQ ID NO:1.

26. The polynucleotide of claim 25, wherein said stop codon is an amber (TAG) or opal (TGA) stop codon.

27. A vector comprising the polynucleotide of claim 5.

28. The vector of claim 27, which is a viral vector.

29. A cell comprising the polynucleotide of claim 5.

30. A virus particle, comprising the vector of claim 27.

31. A pharmaceutical composition comprising the cell of claim 29 and a pharmaceutically effective carrier.

32. A method, comprising introducing the vector of claim 27 to a cell, under conditions whereby expression of the recombinant protein is effected in the cell.

33. A polynucleotide, comprising a modified post-transcriptional regulatory element (PRE), said modified PRE comprising a variant of a wild-type hepatitis virus X gene, said variant X gene comprising a plurality of stop codons not present in the wild-type X gene, wherein said stop codon is selected from among:
- a stop codon beginning at a nucleotide position corresponding to position 420 in the sequence set forth in SEQ ID NO:1;
- a stop codon beginning at a nucleotide position corresponding to position 424 in the sequence set forth in SEQ ID NO:1;
- a stop codon beginning at a nucleotide position corresponding to position 428 in the sequence set forth in SEQ ID NO:1; and
- a stop codon beginning at a nucleotide position corresponding to position 432 in the sequence set forth in SEQ ID NO:1.

34. The polynucleotide of claim 33, wherein said stop codon is an amber (TAG) or opal (TGA) stop codon.

35. The polynucleotide of claim 33, further comprising a nucleic acid encoding a recombinant protein operably linked to the modified PRE.

36. A vector comprising the polynucleotide of claim 35.

37. A cell comprising the polynucleotide of claim 35.

38. A pharmaceutical composition comprising the cell of claim 37 and a pharmaceutically effective carrier.

39. A polynucleotide, comprising a modified post-transcriptional regulatory element (PRE), said modified PRE comprising a variant of a wild-type hepatitis virus X gene, said variant X gene comprising a sequence encoding a post-translational modification signal not present in the wild-type hepatitis virus X gene.

40. The polynucleotide of claim 39, further comprising a nucleic acid encoding a recombinant protein operably linked to the modified PRE.

41. A vector comprising the polynucleotide of claim 40.

42. A cell comprising the polynucleotide of claim 40.

43. A pharmaceutical composition comprising the cell of claim 42 and a pharmaceutically effective carrier.

44. A polynucleotide, comprising a viral nucleic acid comprising a variant Flap, wherein the variant Flap contains a deletion of all or a portion of the nucleotides corresponding to the central polypurine tract (cPPT) and/or the central termination sequence (CTS) regions of a wild-type or unmodified Flap sequence.

45. The polynucleotide of claim 44, further comprising a nucleic acid encoding a recombinant protein operably linked to the variant Flap.

46. A cell comprising the polynucleotide of claim 45.

* * * * *

SEQUENCE LISTING

```
<160> NUMBER OF SEQ ID NOS: 221

<210> SEQ ID NO 1
<211> LENGTH: 592
<212> TYPE: DNA
<213> ORGANISM: Woodchuck hepatitis virus

<400> SEQUENCE: 1
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga ctttcgcttt ccccctcct      300 attgccacgg cggaactcat cgccgcctgc cttgcccgct gctggacagg ggctcggctg     360
ttgggcactg acaattccgt ggtgttgtcg gggaagctga cgtcctttcc atggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgcc tg            592
```

<210> SEQ ID NO 2
<211> LENGTH: 3323
<212> TYPE: DNA
<213> ORGANISM: Woodchuck hepatitis virus

<400> SEQUENCE: 2

```
aattcgggac ataccacgtg gtttagttcc gcctcaaact ccaacaaatc gagatcaagg      60
gagaaagcct actcctccaa ctccacctct aagagatact caccccccact taactatgaa    120
aaatcagact tttcatctcc aggggttcgt agacggatta cgagacttga caacaacgga    180
acgccaacac aatgcctatg gagatccttt tacaacacta agccctgcgg ttcctactgt    240
atccaccata ttgtctcctc cctcgacgac tggggaccct gcactgtcac cggagatgtc    300
accatcaagt ctcctaggac tcctcgcagg attacaggtg gtgtatttct tgtggacaaa    360
aatcctaaca atagctcaga atctagattg gtggtggact tctctcagtt ttccagggg    420
cataccagag tgcactggcc aaaattcgca gttccaaact tgcaaacact tgccaacctc    480
ctgtccacca acttgcaatg gctttcgttg gatgtatctg cggcgtttta tcatatacct    540
attagtcctg ctgctgtgcc tcatcttctt gttggttctc ctggactgga aaggtttaat    600
acctgtctgt cctcttcaac ccacaacaga acaacagtc aattgcagac aatgcacaat    660
ctctgcacaa gacatgtata ctcctcctta ctgttgttgt ttaaaaccta cggcaggaaa    720
ttgcacttgt tgggccatcc cttcatcatg ggctttagga aattacctat gggagtgggc    780
cttagcccgt ttctcttggc tcaatttact agtgcccttg cttcaatggt taggaggaat    840
ttccctcatt gcgtggtttt tgcttatatg gatgatttgg ttttgggggc ccgcacttct    900
gagcatctta ccgccattta ttcccatatt tgttctgttt ttcttgattt gggtatacat    960
ttgaatgtca ataaaacaaa atggtggggc aatcatctac atttcatggg atatgtgatt   1020
actagttcag gtgtattgcc acaagacaaa catgttaaga aaatttcccg ttatttgcac   1080
tctgttcctg ttaatcaacc tctggattac aaaatttgtg aaagattgac tggtattctt   1140
aactatgttg ctcctttac gctatgtgga tacgctgctt taatgccttt gtatcatgct   1200
attgcttccc gtatggcttt catttctctc tccttgtata atcctggtt gctgtctctt   1260
tatgaggagt tgtggcccgt tgtcaggcaa cgtggcgtgg tgtgcactgt gtttgctgac   1320
gcaaccccca ctggttgggg cattgccacc acctgtcagc tcctttccgg gactttcgct   1380
ttccccctcc ctattgccac ggcggaactc atcgccgcct gccttgcccg ctgctggaca   1440
ggggctcggc tgttgggcac tgacaattcc gtggtgttgt cggggaagct gacgtccttt   1500
ccatggctgc tcgcctgtgt tgccacctgg attctgcgcg gacgtccttt ctgctacgtc   1560
ccttcggccc tcaatccagc ggaccttcct tcccgcggcc tgctgccggc tctgcggcct   1620
cttccgcgtc ttcgccttcg ccctcagacg agtcggatct ccctttgggc cgcctccccg   1680
cctgtttcgc ctcggcgtcc ggtccgtgtt gcttggtctt cacctgtgca gacttgcgaa   1740
ccatggattc caccgtgaac tttgtctcct ggcatgcaaa tcgtcaactt ggcatgccaa   1800
gtaaggacct ttggactcct tatataaaag atcaattatt aactaaatgg gaggagggca   1860
gcattgatcc tagattatca atatttgtat taggaggctg taggcataaa tgcatgcgac   1920
ttctgtaacc atgtatcttt tcacctgtg ccttgttttt gcctgtgttc catgtcctac   1980
ttttcaagcc tccaagctgt gccttggatg gctttgggc atggacatag atccctataa   2040
agaatttggt tcatcttatc agttgttgaa ttttcttcct ttggacttct ttcctgacct   2100
taatgctttg gtggacactg ctactgcctt gtatgaagaa gagctaacag gtagggaaca   2160
```

```
ttgctctccg caccatacag ctattagaca agctttagta tgctgggatg aattaactaa    2220
attgatagct tggatgagct ctaacataac ttctgaacaa gtaagaacaa tcatagtaaa    2280
tcatgtcaat gatacctggg gacttaaggt gagacaaagt ttatggtttc atttgtcatg    2340
tctcactttc ggacaacata cagttcaaga attttagta agttttggag tatggatcag    2400
aactccagct ccatatagac ctcctaatgc acccattctc tcgactcttc cggaacatac    2460
agtcattagg agaagaggag gtgcaagagc ttctaggtcc cccagaagac gcactccctc    2520
tcctcgcagg agaagatctc aatcaccgcg tcgcagacgc tctcaatctc catctgccaa    2580
ctgctgatct tcaatgggta cataaaacta atgcaattac aggtctttac tctaaccaag    2640
ctgctcagtt caatccgaat tggattcaac ctgagtttcc tgaacttcat ttacataatg    2700
atttaattca aaaattgcaa cagtattttg gtcctttgac tataaatgaa agagaaaat    2760 tgcaattaaa ttttcctgcc agattttcc ccaaagctac taaatatttc ccttaatta     2820 aaggcataaa aaacaattat cctaattttg ctttagaaca tttctttgct accgcaaatt    2880
atttgtggac tttatgggaa gctggaattt tgtatttaag gaagaatcaa acaactttga    2940
cttttaaagg taaaccatat tcttgggaac acagacagct agtgcaacat aatgggcaac    3000
aacataaaag tcaccttcaa tccagacaaa atagcagcat ggtggcctgc agtgggcact    3060
tattacacaa ccacttatcc tcagaatcag tcagtgtttc aaccaggaat ttatcaaaca    3120
acatctctga taaatcccaa aaatcaacaa gaactggact ctgttcttat aaacagatac    3180
aaacagatag actggaacac ttggcaagga tttcctgtgg atcaaaaatt ttcattggtc    3240
agcagggatc ctccccccaaa accttatata aatcaatcag ctcaaacttt cgaaatcaaa    3300
cctgggccta taatagttcc cgg                                            3323

<210> SEQ ID NO 3
<211> LENGTH: 80
<212> TYPE: DNA
<213> ORGANISM: Woodchuck hepatitis virus

<400> SEQUENCE: 3
gccacggcgg aactcatcgc cgcctgcctt gcccgctgct ggacaggggc tcggctgttg     60
ggcactgaca attccgtggt                                                 80

<210> SEQ ID NO 4
<211> LENGTH: 208
<212> TYPE: DNA
<213> ORGANISM: Woodchuck hepatitis virus

<400> SEQUENCE: 4
gtgtgcactg tgtttgctga cgcaaccccc actggttggg gcattgccac cacctgtcag     60
ctcctttccg ggactttcgc tttccccctc cctattgcca cggcggaact catcgccgcc    120
tgccttgccc gctgctggac aggggctcgg ctgttgggca ctgacaattc cgtggtgttg    180
tcggggaagc tgacgtcctt tccatggc                                       208

<210> SEQ ID NO 5
<211> LENGTH: 38
<212> TYPE: DNA
<213> ORGANISM: Woodchuck hepatitis virus

<400> SEQUENCE: 5
gccttgcccg ctgctggaca ggggctcggc tgttgggc                             38
```

<210> SEQ ID NO 6
<211> LENGTH: 177
<212> TYPE: DNA
<213> ORGANISM: Woodchuck hepatitis virus

<400> SEQUENCE: 6

```
tgctcgcctg tgttgccacc tggattctgc gcgggacgtc cttctgctac gtcccttcgg      60
ccctcaatcc agcggacctt ccttcccgcg gcctgctgcc ggctctgcgg cctcttccgc     120
gtcttcgcct tcgccctcag acgagtcgga tctccctttg ggccgcctcc ccgcctg       177
```

<210> SEQ ID NO 7
<211> LENGTH: 23
<212> TYPE: DNA
<213> ORGANISM: Woodchuck hepatitis virus

<400> SEQUENCE: 7

```
gggacgtcct tctgctacgt ccc                                              23
```

<210> SEQ ID NO 8
<211> LENGTH: 158
<212> TYPE: DNA
<213> ORGANISM: Woodchuck hepatitis virus

<400> SEQUENCE: 8

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggtt                             158
```

<210> SEQ ID NO 9
<211> LENGTH: 426
<212> TYPE: DNA
<213> ORGANISM: Woodchuck hepatitis virus

<400> SEQUENCE: 9

```
atggctgctc gcctgtgttg ccacctggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgcc     180
tgtttcgcct cggcgtccgg tccgtgttgc ttggtcttca cctgtgcaga cttgcgaacc     240
atggattcca ccgtgaactt tgtctcctgg catgcaaatc gtcaacttgg catgccaagt     300
aaggaccttt ggactcctta tataaaagat caattattaa ctaaatggga ggagggcagc     360
attgatccta gattatcaat atttgtatta ggaggctgta ggcataaatg catgcgactt     420
ctgtaa                                                                426
```

<210> SEQ ID NO 10
<211> LENGTH: 182
<212> TYPE: DNA
<213> ORGANISM: Woodchuck hepatitis virus

<400> SEQUENCE: 10

```
atggctgctc gcctgtgttg ccacctggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgcc     180
tg                                                                     182
```

<210> SEQ ID NO 11
<211> LENGTH: 21
<212> TYPE: DNA
<213> ORGANISM: Woodchuck hepatitis virus

<400> SEQUENCE: 11
ggggaagctg acgtcctttc c                                              21

<210> SEQ ID NO 12
<211> LENGTH: 592
<212> TYPE: DNA
<213> ORGANISM: Woodchuck hepatitis virus

<400> SEQUENCE: 12
aatcaacctc tggattacaa aatttgtgaa agattgactg atattcttaa ctatgttgct    60
ccttttacgc tgtgtggata tgctgcttta atgcctctgt atcatgctat tgcttcccgt   120
acggctttcg ttttctcctc cttgtataaa tcctggttgc tgtctcttta tgaggagttg   180
tggcccgttg tccgtcaacg tggcgtggtg tgctctgtgt ttgctgacgc aaccccccact  240 ggctggggca ttgccaccac ctgtcaactc cttctgggga cttttcgcttt cccctcccg   300 atcgccacgg cagaactcat cgccgcctgc cttgcccgct gctggacagg ggctaggttg   360
ctgggcactg ataattccgt ggtgttgtcg gggaagctga cgtcctttcc atggctgctc   420
gcctgtgttg ccaactggat cctgcgcggg acgtccttct gctacgtccc ttcggctctc   480
aatccagcgg acctcccttc ccgaggcctt ctgccggttc tgcggcctct cccgcgtctt   540
cgctttcggc ctccgacgag tcggatctcc ctttgggccg cctccccgcc tg           592

<210> SEQ ID NO 13
<211> LENGTH: 592
<212> TYPE: DNA
<213> ORGANISM: Woodchuck hepatitis virus

<400> SEQUENCE: 13
aatcaacctc tggattacaa aatttctgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact  240 ggttggggca ttgccaccac ctgtcaactc ctttccggga cttacgcttt cccctccct   300 attgccacgg cggaactcat cgccgcctgc cttgcccgct gctggacagg ggctcggctg   360
ttgggcactg acaattccgt ggtgttgtcg gggaagctga cgtcctttcc atggctgctc   420
gcctgtgttg ccacctggat tctgcgcggg acgtccttct gctacgtccc ttcggccctc   480
aatccagcgg accttccttc ccgcggcctg ctgccggctc tgcggcctct ccgcgtctt    540 cgccttcgcc ctcagacgac tcggatctcc ctttgggccg cctccccgcc tg           592

<210> SEQ ID NO 14
<211> LENGTH: 592
<212> TYPE: DNA
<213> ORGANISM: Woodchuck hepatitis virus

<400> SEQUENCE: 14
aatcaacctc tggattacaa aatttgtgaa agattgactg gtattcttaa ctatgttgct    60
ccttttacgc tatgtggata cgctgcttta atgcctttgt atcatgctat tacttcccgt   120
acggctttca ttttctcctc cttgtataaa tcctggttgc tgtctcttta tgaggagttg   180

```
tggcccgttg tcaggcaacg tggcgtggtg tgcactgtgt ttgctgacgc aaccccccact    240 ggttggggca ttgccaccac ctatcaactc ctttccggga ctttcgcttt ccccctccct    300
attgccacgg cggaactcat tgccgcctgc cttgcccgct gctggacagg ggctcggctg    360
ttgggcactg acaattccgt ggtgttgtcg gggaagctga cgtcctttcc atggctgctc    420
gcctgtgttg ccaactggat tctgcgcggg acgtccttct gctacgtccc ttcggccctc    480
aatccagcgg accttccttc ccgcggcctg ctgccggttc tgcggcctct tccgcgtctt    540
cgccttcgcc ctcagacgag tcggatctcc ctttgggccg cctccccgcc tg            592

<210> SEQ ID NO 15
<211> LENGTH: 592
<212> TYPE: DNA
<213> ORGANISM: Woodchuck hepatitis virus

<400> SEQUENCE: 15
aatcaacctc tagattacaa aatttgtgaa agattgactg gtattcttaa ctatgttgct    60
ccttttacgc tgtgtggata tgctgcttta atgcctctgt atcatgctat tgcttcccgt    120
acggctttca ttttctcctc cttgtataaa tcctggttac tgtctcttta tgaggagttg    180
tggcccgttg tcaggcaacg tggcgtggtg tgcactgtgt ttgctgacgc aaccccccact    240 ggctggggca ttgccaccac ctgtcaactc ctttccggga ctttcgcttt ccccctccct    300
atcgccacgg cggaactcat cgccgcctgc cttgcccgct gctggacagg ggctcggctg    360
ttgggcactg acaattccgt ggtgttgtcg gggaagctga cgtcctttcc atggctgctc    420
gcctgtgttg ccaactggat tctgcgcggg acgtccttct gctacgtccc ttcggccctc    480
aatccagcgg acctcccttc ccgcggcctg ctgccggttc tgcggcctct tccacgtctt    540
cgccttcgcc ctcagacgag tcggatctcc ctttgggccg cctccccgcc tg            592

<210> SEQ ID NO 16
<211> LENGTH: 592
<212> TYPE: DNA
<213> ORGANISM: Woodchuck hepatitis virus

<400> SEQUENCE: 16
aatcaacctc tggattacaa aatttgtgaa agattgactg gtattcttaa ctatgttgct    60
ccttttacgc tgtgtggata tgctgcttta atacctctgt atcatgctat tgcttcccgt    120
acggctttcg ttttctcctc cttgtataaa tcctggttgc tgtctcttta tgaggagttg    180
tggcccgttg tccgccaacg tggcgtggtg tgctctgtgt ttgctgacgc aaccccccact    240 ggctggggca ttgccaccac ctgtcaactc ctttctggga ctttcgcttt ccccctcccg    300
atcgccacgg cagaactcat cgccgcctgc cttgcccgct gctggacagg ggctaggttg    360
ttgggcactg ataattccgt ggtgttgtcg gggaagctga cgtcctttcc atggctgctc    420
gcctgtgttg ccaactggat cctacgcggg acgtccttct gctacgtccc ttcagctctc    480
aatccagcgg acctcccttc ccgaggcctt ctgccggttc tgcggcctct cccgcgtctt    540
cgctttcggc ctccgacgag tcggatctcc ctttgggccg cctccccgcc tg            592

<210> SEQ ID NO 17
<211> LENGTH: 592
<212> TYPE: DNA
<213> ORGANISM: Woodchuck hepatitis virus

<400> SEQUENCE: 17
aatcaacctc tggattacaa aatttgtgaa agattgactg gtattcttaa ctatgttgct    60
```

```
ccttttacgc tgtgtggata tgctgcttta atgcctctgt atcatgctat tgcttcccgt      120
acggctttcg ttttctcctc cttgtataaa tcctggttgc tgtctcttta tgaggagttg      180
tggcccgttg tccgccaacg tggcgtggtg tgctctgtgt ttgctgacgc aaccccact       240 ggctggggca ttgccaccac ctgtcaactc ctttctggga ctttcgcttt ccccctcccg      300
atcgccacgg cagaactcat cgccgcctgc cttgcccgct gctggacggg ggctaggttg      360
ttgggcactg ataattccgt ggtgttgtcg gggaagctga cgtcctttcc atggctgctc      420
gcctgtgttg ccaactggat cctacgcggg acgtccttct gctacgtccc ttcagctctc      480
aatccagcgg acctcccttc ccgaggcctt ctgccggttc tgcggcctct cccgcgtctt      540
cgctttcggc ctccgacgag tcggatctcc ctttgggccg cctccccgcc tg              592
```

<210> SEQ ID NO 18
<211> LENGTH: 592
<212> TYPE: DNA
<213> ORGANISM: Woodchuck hepatitis virus

<400> SEQUENCE: 18

```
aatcaacctc tggattacaa aatttgtgaa agattgactg gtattcttaa ctatgttgct      60
ccttttacgc tgtgtggata tgctgcttta atgcctctgt atcatgctat tgcttcccgt      120
acggctttcg ttttctcctc cttgtataaa tcctggttgc tgtctcttta tgaggagttg      180
tggcccgttg tccgccaacg tggcgtggtg tgctctgtgt ttgctgacgc aaccccact       240 ggctggggca ttgccaccac ctgtcaactc ctttctggga ctttcgcttt ccccctcccg      300
atcgccacgg cagaactcat cgccgcctgc cttgcccgct gctggacggg ggctaggttg      360
ttgggcactg ataattccgt ggtgttgtcg gggaagctga cgtcctttcc atggctgctc      420
gcctgtgttg ccaactggat cctacgcggg acgtccttct gctacgtccc ttcagctctc      480
aatccagcgg acctcccttc ccgaggcctt ctgccggttc tgcggcctct cccgcgtctt      540
cgctttcgac ctccgacgag tcggatctcc ctttgggccg cctccccgcc tg              592
```

<210> SEQ ID NO 19
<211> LENGTH: 592
<212> TYPE: DNA
<213> ORGANISM: Woodchuck hepatitis virus

<400> SEQUENCE: 19

```
aatcaacctc tggattacaa aatttgtgaa agattgactg gtattcttaa ctatgttgct      60
ccttttacgc tgtgtggata tgctgcttta ataccctctgt atcatgctat tgcttcccgt     120
acggctttcg ttttctcctc cttgtataaa tcctggttgc tgtctcttta tgaggagttg      180
tggcccgttg tccgccaacg tggcgtggtg tgctctgtgt ttgctgacgc aaccccact       240 ggctggggca ttgccaccac ctgtcaactc ctttctggga ctttcgcttt ccccctcccg      300
atcgccacgg cagaactcat cgccgcctgc cttgcccgct gctggacggg ggctaggttg      360
ttgggcactg ataattccgt ggtgttgtcg gggaagctga cgtcctttcc atggctgctc      420
gcctgtgttg ccaactggat cctacgcggg acgtccttct gctacgtccc ttcagctctc      480
aatccagcgg acctcccttc ccgaggcctt ctgccggttc tgcggcctct cccgcgtctt      540
cgctttcggc ctccgacgag tcggatctcc ctttgggccg cctccccgcc tg              592
```

<210> SEQ ID NO 20
<211> LENGTH: 592
<212> TYPE: DNA

<213> ORGANISM: Woodchuck hepatitis virus

<400> SEQUENCE: 20

| | | | | | |
|---|---|---|---|---|---|
| aatcaacctc | tggattacaa | aatttgtgaa | agattgactg | gtattcttaa | ctatgttgct | 60 |
| ccttttacgc | tgtgtggata | tgctgcttta | atacctctgt | atcgtgctat | tgcttcccgt | 120 |
| acggctttcg | ttttctcctc | cttgtataaa | tcctggttgc | tgtctcttta | tgaggagttg | 180 |
| tggcccgttg | tccgccaacg | tggcgtggtg | tgctctgtgt | ttgctgacgc | aacccccact | 240 |
| ggctggggca | ttgccaccac | ctgtcaactc | ctttctggga | ctttcgcttt | cccctcccg | 300 |
| atcgccacgg | cagaactcat | cgccgcctgc | cttgcccgct | gctggacggg | gctaggttg | 360 |
| ttgggcactg | ataattccgt | ggtgttgtcg | gggaagctga | cgtcctttcc | atggctgctc | 420 |
| gcctgtgttg | ccaactggat | cctacgcggg | acgtccttct | gctacgtccc | ttcagctctc | 480 |
| aatccagcgg | acctcccttc | ccgaggcctt | ctgccggttc | tgcggcctct | cccgcgtctt | 540 |
| cgctttcggc | ctccgacgag | tcggatctcc | ctttgggccg | cctccccgcc | tg | 592 |

<210> SEQ ID NO 21
<211> LENGTH: 722
<212> TYPE: DNA
<213> ORGANISM: Human hepatitis B virus

<400> SEQUENCE: 21

| | | | | | |
|---|---|---|---|---|---|
| aaacaggcct | attgattgga | aagtttgtca | acgaattgtg | ggtctttttgg | ggtttgctgc | 60 |
| ccttttacg | caatgtggat | atcctgcttt | aatgccttta | tatgcatgta | tacaagcaaa | 120 |
| acaggctttt | actttctcgc | caacttacaa | ggcctttctc | agtaaacagt | atatgaccct | 180 |
| ttaccccgtt | gctcggcaac | ggcctggtct | gtgccaagtg | tttgctgacg | caacccccac | 240 |
| tggttggggc | ttggccatag | gccatcagcg | catgcgtgga | acctttgtgt | ctcctctgcc | 300 |
| gatccatact | gcggaactcc | tagccgcttg | ttttgctcgc | agcaggtctg | gagcaaacct | 360 |
| catcgggacc | gacaattctg | tcgtactctc | ccgcaagtat | acatcgtttc | catggctgct | 420 |
| aggctgtgct | gccaactgga | tcctgcgcgg | gacgtccttt | gtttacgtcc | gtcggcgct | 480 |
| gaatcccgcg | gacgacccct | cccggggccg | cttggggctc | taccgcccgc | ttctccgtct | 540 |
| gccgtaccgt | ccgaccacgg | ggcgcacctc | tctttacgcg | gactcccgt | ctgtgccttc | 600 |
| tcatctgccg | gaccgtgtgc | acttcgcttc | acctctgcac | gtcgcatgga | gaccaccgtg | 660 |
| aacgcccacc | ggaacctgcc | caaggtcttg | cataagagga | ctcttggact | ttcagcaatg | 720 |
| tc | | | | | | 722 |

<210> SEQ ID NO 22
<211> LENGTH: 722
<212> TYPE: DNA
<213> ORGANISM: Human hepatitis B virus

<400> SEQUENCE: 22

| | | | | | |
|---|---|---|---|---|---|
| aaacaggcct | attgattgga | aagtatgtca | acgaattgtg | ggtctattgg | ggtttgccgc | 60 |
| ccttttaca | caatgtggat | atcctgctct | aatgccttta | tatgcatgta | tacaagcaaa | 120 |
| acaggctttt | actttctcgc | caacttacaa | ggcctttcta | gtaaacagt | atctgaacct | 180 |
| ttaccccgtt | gctcggcaac | ggcctggtct | gtgccaagtg | tttgctgacg | caacccccac | 240 |
| tggttgggc | ttggcgatag | gccatcagcg | catgcgtggg | acctttctgt | ctcctctgcc | 300 |
| gatccatact | gcggaactcc | tagcagcttg | ttttgctcgc | agcaggtctg | gggcaaaact | 360 |
| catcgggact | gacaattctg | tcgtactctc | ccgcaagtat | acatcatttc | catggctgct | 420 |

```
aggctgtgct gccaactgga tcctgcgcgg gacgtccttt gtttacgtcc cgtcggcgct    480
gaatcccgcg gacgacccct cgcggggccg cttggggctc taccgcccgc ttctccgcct    540
gttctaccga ccgaccacgg ggcgcacctc tctttacgcg gactcccgt ctgtgccttc    600 tcatctgccg gaccgtgtgc acttcgcttc acctctgcac gtcgcatgga gaccaccgtg    660
aacgcccaca ggaacctgcc caaggtcttg cataagagga ctcttggact ttcagcaatg    720
tc                                                                   722

<210> SEQ ID NO 23
<211> LENGTH: 722
<212> TYPE: DNA
<213> ORGANISM: Orangutan hepatitis B virus

<400> SEQUENCE: 23
caacaggcct attgattgga aagtatgtca acgaattgta ggactattgg gctttgccgc    60
tccttttact caatgtggct atcctgcttt aatgccttttg tataactgta tacacaatcg    120
tcaggctttt actttctcgc caacttacaa ggcctttctg cgtacacaat atctgaccct    180
ttaccccgtt gctcggcaac gaccgggact gtgccaagtg tttgctgacg caaccccac    240 tggctggggc ttggcgctag gtccccagcg catgcgtgga acctttgtgg ctcctctgcc    300
gatccatact gcggaactcc tagccgcttg ttttgctcgc agcaggtctg gagcaaacat    360
tatcggtact gacaactctg ttgtgttgtc gcggaaatat acatcttttc catggctgct    420
aggttgtgct gccaactgga tactgcgcgg gacgtccttt gtctacgtcc cgtcggcgct    480
gaatcccgcg gacgaccctt ctcggggtcg gttgggctc taccgccctc ttctccgcct    540
gccgttccgg ccgaccacgg ggcgcacctc tctttacgcg gtctcccgt ctgtgccttc    600 tcatctgccg gtccgtgtgc acttcgcttc acctctgcac gttgcatgga gaccaccgtg    660 aacgccccc ggaacttgcc aaaggtcttg cataagagga ctcttggact gtcaacaatg    720
tc                                                                   722

<210> SEQ ID NO 24
<211> LENGTH: 721
<212> TYPE: DNA
<213> ORGANISM: Chimpanzee hepatitis B virus

<400> SEQUENCE: 24
aacagaccta tagattggaa agtatgtcaa agaattgtgg gtcttttggg atttgctgcc    60
ccttttacgc aatgtggtta tcctgcgtta atgccattgt atgcatgtat acaagcaaaa    120
caggctttca ctttctcgcc aacttataag gcctttctaa gtcaacaata ttcgaccctt    180 tacccgttg cccggcaacg gtccggtctg tgccaagtgt ttgctgacgc aaccccact    240 ggctggggct tggtcatggg ccatcagcgc atgcgtggaa cctttgtggc tcctctgccg    300
atccatactg cggaactcct agcagcttgt tttgctcgca gccggtctgg agcaaaactt    360
atcggaactg acaattctgt cgtcctctct cggaaatata catcttttcc atggctgcta    420
ggttgtgctg ccaactggat acttcgcggg acgtccttttg tttacgtccc gtcggcgctg    480
aatcctgcgg acgaccttc tcgggccgc ttagggctct accgccctct catccgtctg    540
ctcttccaac cgactacggg gcgcacctct ctttacgcgg tctcccgtc tgtgccttct    600 catctgccgg tccgtgtgca cttcgcttca cctctgcacg ttgcatggag accaccgtga    660 acgcccacg gaacctgcca aaagtcttgc ataagaggac tcttggactt tcagcaatgt    720
```

```
c                                                                       721

<210> SEQ ID NO 25
<211> LENGTH: 721
<212> TYPE: DNA
<213> ORGANISM: Gorilla hepatitis B virus

<400> SEQUENCE: 25
aacagaccta ttgattggaa ggtatgtcaa agaattgtgg gtcttttagg atttgctgcc        60
ccttttacac aatgtggtta tcctgccttg atgcctttgt atgcatgtat acaagctaag       120
caggctttca ctttctcgcc aatttacaag gcctttctaa gtaaacaata tgcaacccct       180
taccccgttg ctcggcaacg ggccggtctg tgccaagtgt ttgctgacgc aacccccact       240
ggytggggct tggtcatagg ccagcagcgc atgcgtggaa cctttgtggc tcctctgccg       300
atccatactg cggaactcct agcagcttgt tttgctcgca gcaggtctgg ggcaaacatt       360
atcgggactg acaattctgt cgtcctttca cggaaatata catcctttcc atggctgcta       420
ggctgtgctg ccaactggat cctgcgcggg acgtcctttg tttacgtccc gtcggcgctg       480
aaccctgccg acgacccgtc tcggggtcgc ttaggactct cccgtcctct ctgccgtctg       540
ccgttccagc cgaccacggg gcgcacctct ctttacgcgg tctccccgtc tgtgccttct       600
catctgccgg accgtgtgca cttcgcttca cctctgcacg ttgcatggag accaccgtga       660
acgcccctcg gaacctgcca acagtcttac ataagaggac tcttggactt tcagcaatgt       720
c                                                                       721

<210> SEQ ID NO 26
<211> LENGTH: 582
<212> TYPE: DNA
<213> ORGANISM: Artic ground squirrel hepatitis B virus

<400> SEQUENCE: 26
aacctttaga ttataaaatc tgtgaaaggt taacaggcat tctgaattat gttgctcctt        60
ttactaaatg tggttatgct gctctccttc ctttgtatca agctacttcg cgtacggcat       120
ttgtgttttc ttctctctac cacagctggt tgctgtccct ttatgctgag ttgtggcctg       180
ttgccaggca acgtggcgtg gtgtgctctg tgtctgacgc aacccccact ggttggggca       240
tttgcaccac ctatcaactc atttccccga cgggcgcttt tgccctgccg atcgccaccg       300
cggacgtcat cgccgcctgc cttgctcgct gctggacagg agctcggctg ttgggcactg       360
acaactccgt ggttctttcg ggcaaactga cttcctatcc atggctgctc gcctgtgttg       420
ccaactggat tcttcgcggg acgtcgttct gctacgtccc ttcggcagcg aatccggcgg       480
acctgccgtc tcgaggcctt ctgccggctc tgcatcccgt gccgactctc cgcttccgtc       540
cgcagctgag tcgcatctcc ctttgggccg cctccccgcc tg                          582

<210> SEQ ID NO 27
<211> LENGTH: 592
<212> TYPE: DNA
<213> ORGANISM: Ground squirrel hepatitis B virus

<400> SEQUENCE: 27
aatcaaccct tagattataa aatatgtgaa aggttgacgg gcattcttaa ttatgttgct        60
ccttttacca aatgtggtta tgctgcttta ctgcctttat atcaagctat tgcttctcat       120
actgcttttg ttttctcctc cttatataaa aactggttac tgtcacttta tggtgagttg       180
tggcccgttg ccagacaacg tggtgtggtg tgctctgtgt ttgctgacgc aactcccact       240
```

```
ggttggggca tttgcaccac ctgtcaactc atttccggta ctttcggttt ctcacttccg    300
attgctaccg cggagcttat agccgcctgc cttgctcgct gctggacagg agctcggttg    360
ttgggcactg ataactccgt ggtcctctcc ggtaagctaa cttcgtttcc atggctgctc    420
gcctgtgttg ccaactggat tcttcgcggg acgtccttct gttacgtccc ctccgcggac    480
aacccagcgg accttccgtc tcggggactt ctgccggctc tccgtcctct gccgcttctg    540
cgttttcgtc cggtcaccaa gcggatatcc ctgtgggccg cctccccgcc tg            592
```

<210> SEQ ID NO 28
<211> LENGTH: 24
<212> TYPE: DNA
<213> ORGANISM: Artificial Sequence
<220> FEATURE:
<223> OTHER INFORMATION: Modified portion of X protein ORF

<400> SEQUENCE: 28

```
atggctgctt agctgagtag ctga                                           24
```

<210> SEQ ID NO 29
<211> LENGTH: 592
<212> TYPE: DNA
<213> ORGANISM: Artificial Sequence
<220> FEATURE:
<223> OTHER INFORMATION: MODIFIED PRE WITH FOUR STOP CODONS (1,2,3,4)

<400> SEQUENCE: 29

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact  240 ggttggggca ttgccaccac ctgtcagctc ctttccggga cttttcgcttt ccccctccct   300 attgccacgg cggaactcat cgccgcctgc cttgcccgct gctggacagg ggctcggctg    360
ttgggcactg acaattccgt ggtgttgtcg gggaagctga cgtcctttcc atggctgctt    420
agctgagtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 30
<211> LENGTH: 592
<212> TYPE: DNA
<213> ORGANISM: Artificial Sequence
<220> FEATURE:
<223> OTHER INFORMATION: MODIFIED PRE WITH THREE STOP CODONS (1,2,3)

<400> SEQUENCE: 30

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact  240 ggttggggca ttgccaccac ctgtcagctc ctttccggga cttttcgcttt ccccctccct   300 attgccacgg cggaactcat cgccgcctgc cttgcccgct gctggacagg ggctcggctg    360
ttgggcactg acaattccgt ggtgttgtcg gggaagctga cgtcctttcc atggctgctt    420
```

```
agctgagtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592

<210> SEQ ID NO 31
<211> LENGTH: 592
<212> TYPE: DNA
<213> ORGANISM: Artificial Sequence
<220> FEATURE:
<223> OTHER INFORMATION: MODIFIED PRE WITH THREE STOP CODONS (1,2,4)

<400> SEQUENCE: 31
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240 ggttggggca ttgccaccac ctgtcagctc ctttccggga ctttcgcttt cccctccct   300 attgccacgg cggaactcat cgccgcctgc cttgcccgct gctggacagg ggctcggctg   360
ttgggcactg acaattccgt ggtgttgtcg gggaagctga cgtcctttcc atggctgctt   420
agctgagttg ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg           592

<210> SEQ ID NO 32
<211> LENGTH: 592
<212> TYPE: DNA
<213> ORGANISM: Artificial Sequence
<220> FEATURE:
<223> OTHER INFORMATION: MODIFIED PRE WITH THREE STOP CODONS (1,3,4)

<400> SEQUENCE: 32
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240 ggttggggca ttgccaccac ctgtcagctc ctttccggga ctttcgcttt cccctccct   300 attgccacgg cggaactcat cgccgcctgc cttgcccgct gctggacagg ggctcggctg   360
ttgggcactg acaattccgt ggtgttgtcg gggaagctga cgtcctttcc atggctgctt   420
agctgtgtag ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg           592

<210> SEQ ID NO 33
<211> LENGTH: 592
<212> TYPE: DNA
<213> ORGANISM: Artificial Sequence
<220> FEATURE:
<223> OTHER INFORMATION: MODIFIED PRE WITH THREE STOP CODONS (2,3,4)

<400> SEQUENCE: 33
aatcaacctc tggattacaa aatttgtgaa agattgactg gtattcttaa ctatgttgct    60
ccttttacgc tatgtggata cgctgcttta atgcctttgt atcatgctat tgcttcccgt   120
```

```
atggctttca ttttctcctc cttgtataaa tcctggttgc tgtctcttta tgaggagttg    180
tggcccgttg tcaggcaacg tggcgtggtg tgcactgtgt tgctgacgc aaccccact     240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaagctga cgtcctttcc atggctgctc    420
gcctgagtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 34
<211> LENGTH: 592
<212> TYPE: DNA
<213> ORGANISM: Artificial Sequence
<220> FEATURE:
<223> OTHER INFORMATION: MODIFIED PRE WITH TWO STOP CODONS (1,2)

<400> SEQUENCE: 34

```
aatcaacctc tggattacaa aatttgtgaa agattgactg gtattcttaa ctatgttgct    60 cctttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccact    240 ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaagctga cgtcctttcc atggctgctt   420
agctgagttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg           592
```

<210> SEQ ID NO 35
<211> LENGTH: 592
<212> TYPE: DNA
<213> ORGANISM: Artificial Sequence
<220> FEATURE:
<223> OTHER INFORMATION: MODIFIED PRE WITH TWO STOP CODONS (1,3)

<400> SEQUENCE: 35

```
aatcaacctc tggattacaa aatttgtgaa agattgactg gtattcttaa ctatgttgct    60 cctttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccact    240 ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaagctga cgtcctttcc atggctgctt   420
agctgtgtag ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg           592
```

<210> SEQ ID NO 36

<211> LENGTH: 592
<212> TYPE: DNA
<213> ORGANISM: Artificial Sequence
<220> FEATURE:
<223> OTHER INFORMATION: MODIFIED PRE WITH TWO STOP CODONS (1,4)

<400> SEQUENCE: 36

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaagctga cgtccttttcc atggctgctt | 420 |
| agctgtgttg ctgactggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 37
<211> LENGTH: 592
<212> TYPE: DNA
<213> ORGANISM: Artificial Sequence
<220> FEATURE:
<223> OTHER INFORMATION: MODIFIED PRE WITH TWO STOP CODONS (2,3)

<400> SEQUENCE: 37

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaagctga cgtccttttcc atggctgctc | 420 |
| gcctgagtag ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 38
<211> LENGTH: 592
<212> TYPE: DNA
<213> ORGANISM: Artificial Sequence
<220> FEATURE:
<223> OTHER INFORMATION: MODIFIED PRE WITH TWO STOP CODONS (2,4)

<400> SEQUENCE: 38

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 | ttgggcactg acaattccgt ggtgttgtcg gggaagctga cgtcctttcc atggctgctc    420 gcctgagttg ctgactggat tctgcgcggg acgtccttct gctacgtccc ttcggccctc    480 aatccagcgg accttccttc ccgcggcctg ctgccggctc tgcggcctct tccgcgtctt    540 cgccttcgcc ctcagacgag tcggatctcc ctttgggccg cctccccgcc tg    592

<210> SEQ ID NO 39
<211> LENGTH: 592
<212> TYPE: DNA
<213> ORGANISM: Artificial Sequence
<220> FEATURE:
<223> OTHER INFORMATION: MODIFIED PRE WITH TWO STOP CODONS (3,4)

<400> SEQUENCE: 39
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240 ggttggggca ttgccaccac ctgtcagctc ctttccggga cttttcgcttt cccctccct    300 attgccacgg cggaactcat cgccgcctgc cttgcccgct gctggacagg ggctcggctg    360
ttgggcactg acaattccgt ggtgttgtcg gggaagctga cgtcctttcc atggctgctc    420
gcctgtgtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg    592

<210> SEQ ID NO 40
<211> LENGTH: 592
<212> TYPE: DNA
<213> ORGANISM: Artificial Sequence
<220> FEATURE:
<223> OTHER INFORMATION: MODIFIED PRE WITH ONE STOP CODON (1)

<400> SEQUENCE: 40
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240 ggttggggca ttgccaccac ctgtcagctc ctttccggga cttttcgcttt cccctccct    300 attgccacgg cggaactcat cgccgcctgc cttgcccgct gctggacagg ggctcggctg    360
ttgggcactg acaattccgt ggtgttgtcg gggaagctga cgtcctttcc atggctgctt    420
agctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg    592

<210> SEQ ID NO 41
<211> LENGTH: 592
<212> TYPE: DNA
<213> ORGANISM: Artificial Sequence
<220> FEATURE:
<223> OTHER INFORMATION: MODIFIED PRE WITH ONE STOP CODON (2)

<400> SEQUENCE: 41

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaagctga cgtcctttcc atggctgctc | 420 |
| gcctgagttg ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 42
<211> LENGTH: 592
<212> TYPE: DNA
<213> ORGANISM: Artificial Sequence
<220> FEATURE:
<223> OTHER INFORMATION: MODIFIED PRE WITH ONE STOP CODON (3)

<400> SEQUENCE: 42

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaagctga cgtcctttcc atggctgctc | 420 |
| gcctgtgtag ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 43
<211> LENGTH: 592
<212> TYPE: DNA
<213> ORGANISM: Artificial Sequence
<220> FEATURE:
<223> OTHER INFORMATION: MODIFIED PRE WITH ONE STOP CODON (4)

<400> SEQUENCE: 43

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaagctga cgtcctttcc atggctgctc | 420 |
| gcctgtgttg ctgactggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 44
<211> LENGTH: 182
<212> TYPE: DNA
<213> ORGANISM: Artificial Sequence
<220> FEATURE:
<223> OTHER INFORMATION: TRUNCATED X GENE WITH FOUR STOP CODONS (1,2,3,
      4)

<400> SEQUENCE: 44

```
atggctgctt agctgagtag ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgcc     180
tg                                                                    182
```

<210> SEQ ID NO 45
<211> LENGTH: 182
<212> TYPE: DNA
<213> ORGANISM: Artificial Sequence
<220> FEATURE:
<223> OTHER INFORMATION: TRUNCATED X GENE THREE STOP CODONS (1,2,3)

<400> SEQUENCE: 45

```
atggctgctt agctgagtag ccacctggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgcc     180
tg                                                                    182
```

<210> SEQ ID NO 46
<211> LENGTH: 182
<212> TYPE: DNA
<213> ORGANISM: Artificial Sequence
<220> FEATURE:
<223> OTHER INFORMATION: TRUNCATED X GENE THREE STOP CODONS (1,2,4)

<400> SEQUENCE: 46

```
atggctgctt agctgagttg ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgcc     180
tg                                                                    182
```

<210> SEQ ID NO 47
<211> LENGTH: 182
<212> TYPE: DNA
<213> ORGANISM: Artificial Sequence
<220> FEATURE:
<223> OTHER INFORMATION: TRUNCATED X GENE WITH THREE STOP CODONS (1,3,4)

<400> SEQUENCE: 47

```
atggctgctt agctgtgtag ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgcc     180
tg                                                                    182
```

<210> SEQ ID NO 48
<211> LENGTH: 182
<212> TYPE: DNA
<213> ORGANISM: Artificial Sequence

```
<220> FEATURE:
<223> OTHER INFORMATION: TRUNCATED X GENE WITH THREE STOP CODONS (2,3,4)

<400> SEQUENCE: 48
atggctgctc gcctgagtag ctgactggat tctgcgcggg acgtccttct gctacgtccc        60
ttcggccctc aatccagcgg accttccttc ccgcggcctg ctgccggctc tgcggcctct       120
tccgcgtctt cgccttcgcc ctcagacgag tcggatctcc ctttgggccg cctccccgcc       180
tg                                                                     182

<210> SEQ ID NO 49
<211> LENGTH: 182
<212> TYPE: DNA
<213> ORGANISM: Artificial Sequence
<220> FEATURE:
<223> OTHER INFORMATION: TRUNCATED X GENE WITH TWO STOP CODONS (1,2)

<400> SEQUENCE: 49
atggctgctt agctgagttg ccacctggat tctgcgcggg acgtccttct gctacgtccc        60
ttcggccctc aatccagcgg accttccttc ccgcggcctg ctgccggctc tgcggcctct       120
tccgcgtctt cgccttcgcc ctcagacgag tcggatctcc ctttgggccg cctccccgcc       180
tg                                                                     182

<210> SEQ ID NO 50
<211> LENGTH: 182
<212> TYPE: DNA
<213> ORGANISM: Artificial Sequence
<220> FEATURE:
<223> OTHER INFORMATION: TRUNCATED X GENE WITH TWO STOP CODONS (1,3)

<400> SEQUENCE: 50
atggctgctt agctgtgtag ccacctggat tctgcgcggg acgtccttct gctacgtccc        60
ttcggccctc aatccagcgg accttccttc ccgcggcctg ctgccggctc tgcggcctct       120
tccgcgtctt cgccttcgcc ctcagacgag tcggatctcc ctttgggccg cctccccgcc       180
tg                                                                     182

<210> SEQ ID NO 51
<211> LENGTH: 182
<212> TYPE: DNA
<213> ORGANISM: Artificial Sequence
<220> FEATURE:
<223> OTHER INFORMATION: TRUNCATED X GENE WITH TWO STOP CODONS (1,4)

<400> SEQUENCE: 51
atggctgctt agctgtgttg ctgactggat tctgcgcggg acgtccttct gctacgtccc        60
ttcggccctc aatccagcgg accttccttc ccgcggcctg ctgccggctc tgcggcctct       120
tccgcgtctt cgccttcgcc ctcagacgag tcggatctcc ctttgggccg cctccccgcc       180
tg                                                                     182

<210> SEQ ID NO 52
<211> LENGTH: 182
<212> TYPE: DNA
<213> ORGANISM: Artificial Sequence
<220> FEATURE:
<223> OTHER INFORMATION: TRUNCATED X GENE WITH TWO STOP CODONS (2,3)

<400> SEQUENCE: 52
atggctgctc gcctgagtag ccacctggat tctgcgcggg acgtccttct gctacgtccc        60
```

```
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182

<210> SEQ ID NO 53
<211> LENGTH: 182
<212> TYPE: DNA
<213> ORGANISM: Artificial Sequence
<220> FEATURE:
<223> OTHER INFORMATION: TRUNCATED X GENE WITH TWO STOP CODONS (2,4)

<400> SEQUENCE: 53
atggctgctc gcctgagttg ctgactggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182

<210> SEQ ID NO 54
<211> LENGTH: 182
<212> TYPE: DNA
<213> ORGANISM: Artificial Sequence
<220> FEATURE:
<223> OTHER INFORMATION: TRUNCATED X GENE WITH TWO STOP CODONS (3,4)

<400> SEQUENCE: 54
atggctgctc gcctgtgtag ctgactggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182

<210> SEQ ID NO 55
<211> LENGTH: 182
<212> TYPE: DNA
<213> ORGANISM: Artificial Sequence
<220> FEATURE:
<223> OTHER INFORMATION: TRUNCATED X GENE WITH ONE STOP CODON (1)

<400> SEQUENCE: 55
atggctgctt agctgtgttg ccacctggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182

<210> SEQ ID NO 56
<211> LENGTH: 182
<212> TYPE: DNA
<213> ORGANISM: Artificial Sequence
<220> FEATURE:
<223> OTHER INFORMATION: TRUNCATED X GENE WITH ONE STOP CODON (2)

<400> SEQUENCE: 56
atggctgctc gcctgagttg ccacctggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182
```

```
<210> SEQ ID NO 57
<211> LENGTH: 182
<212> TYPE: DNA
<213> ORGANISM: Artificial Sequence
<220> FEATURE:
<223> OTHER INFORMATION: TRUNCATED X GENE WITH ONE STOP CODON (3)

<400> SEQUENCE: 57
atggctgctc gcctgtgtag ccacctggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgcc     180
tg                                                                    182

<210> SEQ ID NO 58
<211> LENGTH: 182
<212> TYPE: DNA
<213> ORGANISM: Artificial Sequence
<220> FEATURE:
<223> OTHER INFORMATION: TRUNCATED X GENE WITH ONE STOP CODON (4)

<400> SEQUENCE: 58
atggctgctc gcctgtgttg ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgcc     180
tg                                                                    182

<210> SEQ ID NO 59
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 59 aatcaaccctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaagctga cgtcctttcc ggggctgctt    420
agctgagtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592

<210> SEQ ID NO 60
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 60 aatcaaccctc tggattacaa aatttgtgaa agattgactg gtattcttaa ctatgttgct     60
ccttttacgc tatgtggata cgctgcttta atgcctttgt atcatgctat tgcttcccgt    120
```

```
atggctttca ttttctcctc cttgtataaa tcctggttgc tgtctcttta tgaggagttg    180
tggcccgttg tcaggcaacg tggcgtggtg tgcactgtgt tgctgacgc aaccccact      240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaagctga cgtcctttcc ggggctgctt    420
agctgagtag ccacctggat tctgcgcggg acgtccttct gctacgtccc ttcggccctc    480
aatccagcgg accttccttc ccgcggcctg ctgccggctc tgcggcctct ccgcgtctt     540 cgccttcgcc ctcagacgag tcggatctcc ctttgggccg cctccccgcc tg            592

<210> SEQ ID NO 61
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 61
aatcaacctc tggattacaa aatttgtgaa agattgactg gtattcttaa ctatgttgct    60 cctttacgc tatgtggata cgctgcttta atgcctttgt atcatgctat tgcttcccgt     120
atggctttca ttttctcctc cttgtataaa tcctggttgc tgtctcttta tgaggagttg    180
tggcccgttg tcaggcaacg tggcgtggtg tgcactgtgt tgctgacgc aaccccact      240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaagctga cgtcctttcc ggggctgctt    420
agctgagttg ctgactggat tctgcgcggg acgtccttct gctacgtccc ttcggccctc    480
aatccagcgg accttccttc ccgcggcctg ctgccggctc tgcggcctct ccgcgtctt     540 cgccttcgcc ctcagacgag tcggatctcc ctttgggccg cctccccgcc tg            592

<210> SEQ ID NO 62
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 62
aatcaacctc tggattacaa aatttgtgaa agattgactg gtattcttaa ctatgttgct    60 cctttacgc tatgtggata cgctgcttta atgcctttgt atcatgctat tgcttcccgt     120
atggctttca ttttctcctc cttgtataaa tcctggttgc tgtctcttta tgaggagttg    180
tggcccgttg tcaggcaacg tggcgtggtg tgcactgtgt tgctgacgc aaccccact      240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaagctga cgtcctttcc ggggctgctt    420
agctgtgtag ctgactggat tctgcgcggg acgtccttct gctacgtccc ttcggccctc    480
aatccagcgg accttccttc ccgcggcctg ctgccggctc tgcggcctct ccgcgtctt     540 cgccttcgcc ctcagacgag tcggatctcc ctttgggccg cctccccgcc tg            592

<210> SEQ ID NO 63
<211> LENGTH: 592
```

<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 63

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | ttgctgacgc | aacccccact | 240 |
| ggttggggca | ttgccaccac | ctgtcagctc | ctttccggga | ctttcgcttt | ccccctccct | 300 |
| attgccacgg | cggaactcat | cgccgcctgc | cttgcccgct | gctggacagg | ggctcggctg | 360 |
| ttgggcactg | acaattccgt | ggtgttgtcg | gggaagctga | cgtcctttcc | ggggctgctc | 420 |
| gcctgagtag | ctgactggat | tctgcgcggg | acgtccttct | gctacgtccc | ttcggccctc | 480 |
| aatccagcgg | accttccttc | ccgcggcctg | ctgccggctc | tgcggcctct | tccgcgtctt | 540 |
| cgccttcgcc | ctcagacgag | tcggatctcc | ctttgggccg | cctccccgcc | tg | 592 |

<210> SEQ ID NO 64
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 64

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | ttgctgacgc | aacccccact | 240 |
| ggttggggca | ttgccaccac | ctgtcagctc | ctttccggga | ctttcgcttt | ccccctccct | 300 |
| attgccacgg | cggaactcat | cgccgcctgc | cttgcccgct | gctggacagg | ggctcggctg | 360 |
| ttgggcactg | acaattccgt | ggtgttgtcg | gggaagctga | cgtcctttcc | ggggctgctc | 420 |
| agctgagttg | ccacctggat | tctgcgcggg | acgtccttct | gctacgtccc | ttcggccctc | 480 |
| aatccagcgg | accttccttc | ccgcggcctg | ctgccggctc | tgcggcctct | tccgcgtctt | 540 |
| cgccttcgcc | ctcagacgag | tcggatctcc | ctttgggccg | cctccccgcc | tg | 592 |

<210> SEQ ID NO 65
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 65

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | ttgctgacgc | aacccccact | 240 |
| ggttggggca | ttgccaccac | ctgtcagctc | ctttccggga | ctttcgcttt | ccccctccct | 300 |
| attgccacgg | cggaactcat | cgccgcctgc | cttgcccgct | gctggacagg | ggctcggctg | 360 |

```
ttgggcactg acaattccgt ggtgttgtcg gggaagctga cgtcctttcc ggggctgctt      420
agctgtgtag ccacctggat tctgcgcggg acgtccttct gctacgtccc ttcggccctc      480
aatccagcgg accttccttc ccgcggcctg ctgccggctc tgcggcctct ccgcgtctt       540 cgccttcgcc ctcagacgag tcggatctcc ctttgggccg cctccccgcc tg              592
```

<210> SEQ ID NO 66
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 66

```
aatcaacctc tggattacaa aatttgtgaa agattgactg gtattcttaa ctatgttgct       60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact       240 ggttggggca ttgccaccac ctgtcagctc ctttccggga cttttcgcttt ccccctccct     300 attgccacgg cggaactcat cgccgcctgc cttgcccgct gctggacagg ggctcggctg      360
ttgggcactg acaattccgt ggtgttgtcg gggaagctga cgtcctttcc ggggctgctt      420
agctgtgttg ctgactggat tctgcgcggg acgtccttct gctacgtccc ttcggccctc      480
aatccagcgg accttccttc ccgcggcctg ctgccggctc tgcggcctct ccgcgtctt       540 cgccttcgcc ctcagacgag tcggatctcc ctttgggccg cctccccgcc tg              592
```

<210> SEQ ID NO 67
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 67

```
aatcaacctc tggattacaa aatttgtgaa agattgactg gtattcttaa ctatgttgct       60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact       240 ggttggggca ttgccaccac ctgtcagctc ctttccggga cttttcgcttt ccccctccct     300 attgccacgg cggaactcat cgccgcctgc cttgcccgct gctggacagg ggctcggctg      360
ttgggcactg acaattccgt ggtgttgtcg gggaagctga cgtcctttcc ggggctgctc      420
gcctgagtag ccacctggat tctgcgcggg acgtccttct gctacgtccc ttcggccctc      480
aatccagcgg accttccttc ccgcggcctg ctgccggctc tgcggcctct ccgcgtctt       540 cgccttcgcc ctcagacgag tcggatctcc ctttgggccg cctccccgcc tg              592
```

<210> SEQ ID NO 68
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 68

```
aatcaacctc tggattacaa aatttgtgaa agattgactg gtattcttaa ctatgttgct       60
```

```
cctttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaagctga cgtcctttcc ggggctgctc    420
gcctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg           592
```

<210> SEQ ID NO 69
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 69

```
aatcaacctc tggattacaa aatttgtgaa agattgactg gtattcttaa ctatgttgct    60 cctttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaagctga cgtcctttcc ggggctgctc    420
gcctgtgtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg           592
```

<210> SEQ ID NO 70
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 70

```
aatcaacctc tggattacaa aatttgtgaa agattgactg gtattcttaa ctatgttgct    60 cctttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaagctga cgtcctttcc ggggctgctc    420
agctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg           592
```

<210> SEQ ID NO 71
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 71

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | ttgctgacgc | aacccccact | 240 |
| ggttggggca | ttgccaccac | ctgtcagctc | ctttccggga | cttcgctttc | cccctccct | 300 |
| attgccacgg | cggaactcat | cgccgcctgc | cttgcccgct | gctggacagg | ggctcggctg | 360 |
| ttgggcactg | acaattccgt | ggtgttgtcg | gggaagctga | cgtcctttcc | ggggctgctc | 420 |
| gcctgagttg | ccacctggat | tctgcgcggg | acgtccttct | gctacgtccc | ttcggccctc | 480 |
| aatccagcgg | accttccttc | ccgcggcctg | ctgccggctc | tgcggcctct | tccgcgtctt | 540 |
| cgccttcgcc | ctcagacgag | tcggatctcc | ctttgggccg | cctccccgcc | tg | 592 |

<210> SEQ ID NO 72
<211> LENGTH: 592
<212> TYPE: DNA
<213> ORGANISM: Artificial Sequence
<220> FEATURE:
<223> OTHER INFORMATION: MODIFIED PRE WITH START AND STOP

<400> SEQUENCE: 72

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | ttgctgacgc | aacccccact | 240 |
| ggttggggca | ttgccaccac | ctgtcagctc | ctttccggga | cttcgctttc | cccctccct | 300 |
| attgccacgg | cggaactcat | cgccgcctgc | cttgcccgct | gctggacagg | ggctcggctg | 360 |
| ttgggcactg | acaattccgt | ggtgttgtcg | gggaagctga | cgtcctttcc | ggggctgctc | 420 |
| gcctgtgtag | ccacctggat | tctgcgcggg | acgtccttct | gctacgtccc | ttcggccctc | 480 |
| aatccagcgg | accttccttc | ccgcggcctg | ctgccggctc | tgcggcctct | tccgcgtctt | 540 |
| cgccttcgcc | ctcagacgag | tcggatctcc | ctttgggccg | cctccccgcc | tg | 592 |

<210> SEQ ID NO 73
<211> LENGTH: 592
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 73

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | ttgctgacgc | aacccccact | 240 |
| ggttggggca | ttgccaccac | ctgtcagctc | ctttccggga | cttcgctttc | cccctccct | 300 |

```
attgccacgg cggaactcat cgccgcctgc cttgcccgct gctggacagg ggctcggctg    360
ttgggcactg acaattccgt ggtgttgtcg gggaagctga cgtcctttcc ggggctgctc    420
gcctgtgttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

```
<210> SEQ ID NO 74
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 74
ggggctgctt agctgagtag ctgactggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182
```

```
<210> SEQ ID NO 75
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 75
ggggctgctt agctgagtag ccacctggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182
```

```
<210> SEQ ID NO 76
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 76
ggggctgctt agctgagttg ctgactggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182
```

```
<210> SEQ ID NO 77
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 77
``` gggggctgctt agctgtgtag ctgactggat tctgcgcggg acgtccttct gctacgtccc      60
ttcggccctc aatccagcgg accttccttc ccgcggcctg ctgccggctc tgcggcctct      120
tccgcgtctt cgccttcgcc ctcagacgag tcggatctcc ctttgggccg cctccccgcc      180
tg                                                                    182

<210> SEQ ID NO 78
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 78
ggggctgctc gcctgagtag ctgactggat tctgcgcggg acgtccttct gctacgtccc      60
ttcggccctc aatccagcgg accttccttc ccgcggcctg ctgccggctc tgcggcctct      120
tccgcgtctt cgccttcgcc ctcagacgag tcggatctcc ctttgggccg cctccccgcc      180
tg                                                                    182

<210> SEQ ID NO 79
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 79
ggggctgctt agctgagttg ccacctggat tctgcgcggg acgtccttct gctacgtccc      60
ttcggccctc aatccagcgg accttccttc ccgcggcctg ctgccggctc tgcggcctct      120
tccgcgtctt cgccttcgcc ctcagacgag tcggatctcc ctttgggccg cctccccgcc      180
tg                                                                    182

<210> SEQ ID NO 80
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 80
ggggctgctt agctgtgtag ccacctggat tctgcgcggg acgtccttct gctacgtccc      60
ttcggccctc aatccagcgg accttccttc ccgcggcctg ctgccggctc tgcggcctct      120
tccgcgtctt cgccttcgcc ctcagacgag tcggatctcc ctttgggccg cctccccgcc      180
tg                                                                    182

<210> SEQ ID NO 81
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 81
ggggctgctt agctgtgttg ctgactggat tctgcgcggg acgtccttct gctacgtccc      60
ttcggccctc aatccagcgg accttccttc ccgcggcctg ctgccggctc tgcggcctct      120

```
tccgcgtctt cgccttcgcc ctcagacgag tcggatctcc ctttgggccg cctccccgcc    180
tg                                                                   182

<210> SEQ ID NO 82
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 82
ggggctgctc gcctgagtag ccacctggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182

<210> SEQ ID NO 83
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 83
ggggctgctc gcctgagttg ctgactggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182

<210> SEQ ID NO 84
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 84
ggggctgctc gcctgtgtag ctgactggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
tg                                                                   182

<210> SEQ ID NO 85
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 85
ggggctgctt agctgtgttg ccacctggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgcc    180
```

-continued

| | |
|---|---|
| tg | 182 |

<210> SEQ ID NO 86
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 86

| | |
|---|---|
| ggggctgctc gcctgagttg ccacctggat tctgcgcggg acgtccttct gctacgtccc | 60 |
| ttcggccctc aatccagcgg accttccttc ccgcggcctg ctgccggctc tgcggcctct | 120 |
| tccgcgtctt cgccttcgcc ctcagacgag tcggatctcc ctttgggccg cctccccgcc | 180 |
| tg | 182 |

<210> SEQ ID NO 87
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 87

| | |
|---|---|
| ggggctgctc gcctgtgtag ccacctggat tctgcgcggg acgtccttct gctacgtccc | 60 |
| ttcggccctc aatccagcgg accttccttc ccgcggcctg ctgccggctc tgcggcctct | 120 |
| tccgcgtctt cgccttcgcc ctcagacgag tcggatctcc ctttgggccg cctccccgcc | 180 |
| tg | 182 |

<210> SEQ ID NO 88
<211> LENGTH: 182
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 88

| | |
|---|---|
| ggggctgctc gcctgtgttg ctgactggat tctgcgcggg acgtccttct gctacgtccc | 60 |
| ttcggccctc aatccagcgg accttccttc ccgcggcctg ctgccggctc tgcggcctct | 120 |
| tccgcgtctt cgccttcgcc ctcagacgag tcggatctcc ctttgggccg cctccccgcc | 180 |
| tg | 182 |

<210> SEQ ID NO 89
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 89

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt cccctccct | 300 |

```
attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgagtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

```
<210> SEQ ID NO 90
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 90
```

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgagtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

```
<210> SEQ ID NO 91
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 91
```

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

```
<210> SEQ ID NO 92
<211> LENGTH: 592
<212> TYPE: DNA
<213> ORGANISM: Artificial Sequence
<220> FEATURE:
```

<223> OTHER INFORMATION: MODIFIED PRE WITH PROMOTER SEQUENCE AND STOP
      CODONS

<400> SEQUENCE: 92
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccact    240 ggttggggca ttgccaccac ctgtcagctc ctttccggga cttttcgcttt cccctccct    300 attgccacgg cggaactcat cgccgcctgc cttgcccgct gctggacagg ggctcggctg   360
ttgggcactg acaattccgt ggtgttgtcg gggaaggtct gctgagactc atggctgctt   420
agctgtgtag ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg          592

<210> SEQ ID NO 93
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 93
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccact    240 ggttggggca ttgccaccac ctgtcagctc ctttccggga cttttcgcttt cccctccct    300 attgccacgg cggaactcat cgccgcctgc cttgcccgct gctggacagg ggctcggctg   360
ttgggcactg acaattccgt ggtgttgtcg gggaaggtct gctgagactc atggctgctc   420
gcctgagtag ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg          592

<210> SEQ ID NO 94
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 94
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccact    240 ggttggggca ttgccaccac ctgtcagctc ctttccggga cttttcgcttt cccctccct    300 attgccacgg cggaactcat cgccgcctgc cttgcccgct gctggacagg ggctcggctg   360

```
ttgggcactg acaattccgt ggtgttgtcg gggaaggtct gctgagactc atggctgctt    420
agctgagttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 95
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP CODONS

<400> SEQUENCE: 95

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgtgtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 96
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP CODONS

<400> SEQUENCE: 96

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgtgttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 97
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP CODONS

<400> SEQUENCE: 97

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact     240
ggttggggca ttgccaccac ctgtcagctc ctttccggga ctttcgcttt ccccctccct     300
attgccacgg cggaactcat cgccgcctgc cttcccgct gctggacagg ggctcggctg      360
ttgggcactg acaattccgt ggtgttgtcg gggaaggtct gctgagactc atggctgctc     420
gcctgagtag ccacctggat tctgcgcggg acgtccttct gctacgtccc ttcggccctc     480
aatccagcgg accttcct ccgcggcctg ctgccggctc tgcggcctct tccgcgtctt      540
cgccttcgcc ctcagacgag tcggatctcc ctttgggccg cctccccgcc tg            592
```

<210> SEQ ID NO 98
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 98

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact     240
ggttggggca ttgccaccac ctgtcagctc ctttccggga ctttcgcttt ccccctccct     300
attgccacgg cggaactcat cgccgcctgc cttcccgct gctggacagg ggctcggctg      360
ttgggcactg acaattccgt ggtgttgtcg gggaaggtct gctgagactc atggctgctc     420
gcctgagttg ctgactggat tctgcgcggg acgtccttct gctacgtccc ttcggccctc     480
aatccagcgg accttcct ccgcggcctg ctgccggctc tgcggcctct tccgcgtctt      540
cgccttcgcc ctcagacgag tcggatctcc ctttgggccg cctccccgcc tg            592
```

<210> SEQ ID NO 99
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 99

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact     240
ggttggggca ttgccaccac ctgtcagctc ctttccggga ctttcgcttt ccccctccct     300
attgccacgg cggaactcat cgccgcctgc cttcccgct gctggacagg ggctcggctg      360
ttgggcactg acaattccgt ggtgttgtcg gggaaggtct gctgagactc atggctgctc     420
gcctgtgtag ctgactggat tctgcgcggg acgtccttct gctacgtccc ttcggccctc     480
```

```
aatccagcgg accttccttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 100
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODON

<400> SEQUENCE: 100

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaggtct gctgagactc atggctgctc    420
agctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 101
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODON

<400> SEQUENCE: 101

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaggtct gctgagactc atggctgctc    420
gcctgagttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 102
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODON

<400> SEQUENCE: 102

```
aatcaacctc tggattacaa aatttgtgaa agattgactg gtattcttaa ctatgttgct    60
```

```
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact       240 ggttggggca ttgccaccac ctgtcagctc ctttccggga ctttcgcttt ccccctccct      300
attgccacgg cggaactcat cgccgcctgc cttgcccgct gctggacagg ggctcggctg      360
ttgggcactg acaattccgt ggtgttgtcg gggaaggtct gctgagactc atggctgctc      420
gcctgtgtag ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc tg             592
```

<210> SEQ ID NO 103
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODON

<400> SEQUENCE: 103

```
aatcaacctc tggattacaa aatttgtgaa agattgactg gtattcttaa ctatgttgct       60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact       240 ggttggggca ttgccaccac ctgtcagctc ctttccggga ctttcgcttt ccccctccct      300
attgccacgg cggaactcat cgccgcctgc cttgcccgct gctggacagg ggctcggctg      360
ttgggcactg acaattccgt ggtgttgtcg gggaaggtct gctgagactc atggctgctc      420
gcctgtgttg ctgactggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc tg             592
```

<210> SEQ ID NO 104
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 104

```
aatcaacctc tggattacaa aatttgtgaa agattgactg gtattcttaa ctatgttgct       60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact       240 ggttggggca ttgccaccac ctgtcagctc ctttccggga ctttcgcttt ccccctccct      300
attgccacgg cggaactcat cgccgcctgc cttgcccgct gctggacagg ggctcggctg      360
ttgggcactg acaattccgt ggtgttgtcg gggaaggtct gctgagactc ggggctgctt      420
agctgagtag ctgactggat tctgcgcggg acgtccttct gctacgtccc ttcggccctc      480
aatccagcgg accttccttc ccgcggcctg ctgccggctc tgcggcctct tccgcgtctt      540
```

```
cgccttcgcc ctcagacgag tcggatctcc ctttgggccg cctccccgcc tg        592
```

<210> SEQ ID NO 105
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 105

```
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccact   240
ggttggggca ttgccaccac ctgtcagctc ctttccggga cttttcgcttt cccctccct  300
attgccacgg cggaactcat cgccgcctgc cttgcccgct gctggacagg ggctcggctg  360
ttgggcactg acaattccgt ggtgttgtcg gggaaggtct gctgagactc ggggctgctt  420
agctgagtag ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc tg         592
```

<210> SEQ ID NO 106
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 106

```
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccact   240
ggttggggca ttgccaccac ctgtcagctc ctttccggga cttttcgcttt cccctccct  300
attgccacgg cggaactcat cgccgcctgc cttgcccgct gctggacagg ggctcggctg  360
ttgggcactg acaattccgt ggtgttgtcg gggaaggtct gctgagactc ggggctgctt  420
agctgagttg ctgactggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc tg         592
```

<210> SEQ ID NO 107
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 107

```
aatcaacctc tggattacaa aatttgtgaa agattgactg gtattcttaa ctatgttgct   60
ccttttacgc tatgtggata cgctgcttta atgcctttgt atcatgctat tgcttcccgt  120
```

| | |
|---|---|
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctt | 420 |
| agctgtgtag ctgactggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 108
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 108

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctc | 420 |
| gcctgagtag ctgactggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 109
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 109

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctt | 420 |
| agctgagttg ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 110
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 110

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240
ggttggggca ttgccaccac ctgtcagctc ctttccggga cttcgctttt ccccctccct   300
attgccacgg cggaactcat cgccgcctgc cttgcccgct gctggacagg ggctcggctg   360
ttgggcactg acaattccgt ggtgttgtcg gggaaggtct gctgagactc ggggctgctt   420
agctgtgtag ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg           592
```

<210> SEQ ID NO 111
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 111

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240
ggttggggca ttgccaccac ctgtcagctc ctttccggga cttcgctttt ccccctccct   300
attgccacgg cggaactcat cgccgcctgc cttgcccgct gctggacagg ggctcggctg   360
ttgggcactg acaattccgt ggtgttgtcg gggaaggtct gctgagactc ggggctgctt   420
agctgtgttg ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg           592
```

<210> SEQ ID NO 112
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 112

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240
```

-continued

| | |
|---|---|
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctc | 420 |
| gcctgagtag ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 113
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
AND STOP CODONS

<400> SEQUENCE: 113

| | |
|---|---|
| aatcaacctc tggattacaa aatttgtgaa agattgactg gtattcttaa ctatgttgct | 60 |
| cctttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctc | 420 |
| gcctgagttg ctgactggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 114
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
AND STOP CODONS

<400> SEQUENCE: 114

| | |
|---|---|
| aatcaacctc tggattacaa aatttgtgaa agattgactg gtattcttaa ctatgttgct | 60 |
| cctttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctc | 420 |
| gcctgtgtag ctgactggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 115
<211> LENGTH: 592
<212> TYPE: DNA

<213> ORGANISM: Artificial Sequence
<220> FEATURE:
<223> OTHER INFORMATION: MODIFIED PRE WITH PROMOTER SEQUENCE AND START
      AND STOP CODON

<400> SEQUENCE: 115

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt tgctgacgc aaccccact       240
ggttggggca ttgccaccac ctgtcagctc ctttccggga ctttcgcttt cccctccct     300
attgccacgg cggaactcat cgccgcctgc cttgcccgct gctggacagg ggctcggctg     360
ttgggcactg acaattccgt ggtgttgtcg gggaaggtct gctgagactc ggggctgctt     420
agctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgcc tg             592
```

<210> SEQ ID NO 116
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODON

<400> SEQUENCE: 116

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt tgctgacgc aaccccact       240
ggttggggca ttgccaccac ctgtcagctc ctttccggga ctttcgcttt cccctccct     300
attgccacgg cggaactcat cgccgcctgc cttgcccgct gctggacagg ggctcggctg     360
ttgggcactg acaattccgt ggtgttgtcg gggaaggtct gctgagactc ggggctgctc     420
gcctgagttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgcc tg             592
```

<210> SEQ ID NO 117
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODON

<400> SEQUENCE: 117

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt tgctgacgc aaccccact       240
ggttggggca ttgccaccac ctgtcagctc ctttccggga ctttcgcttt cccctccct     300
```

```
attgccacgg cggaactcat cgccgcctgc cttgcccgct gctggacagg ggctcggctg      360
ttgggcactg acaattccgt ggtgttgtcg gggaaggtct gctgagactc ggggctgctc      420
gcctgtgtag ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc tg              592
```

<210> SEQ ID NO 118
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODON

<400> SEQUENCE: 118

```
aatcaacctc tggattacaa aatttgtgaa agattgactg gtattcttaa ctatgttgct       60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccccact     240 ggttggggca ttgccaccac ctgtcagctc ctttccggga cttttcgcttt ccccctccct    300 attgccacgg cggaactcat cgccgcctgc cttgcccgct gctggacagg ggctcggctg      360
ttgggcactg acaattccgt ggtgttgtcg gggaaggtct gctgagactc ggggctgctc      420
gcctgtgttg ctgactggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc tg              592
```

<210> SEQ ID NO 119
<211> LENGTH: 592
<212> TYPE: DNA
<213> ORGANISM: Artificial Sequence
<220> FEATURE:
<223> OTHER INFORMATION: MODIFIED PRE WITH PROMOTER SEQUENCE AND START
      CODON

<400> SEQUENCE: 119

```
aatcaacctc tggattacaa aatttgtgaa agattgactg gtattcttaa ctatgttgct       60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccccact     240 ggttggggca ttgccaccac ctgtcagctc ctttccggga cttttcgcttt ccccctccct    300 attgccacgg cggaactcat cgccgcctgc cttgcccgct gctggacagg ggctcggctg      360
ttgggcactg acaattccgt ggtgttgtcg gggaaatcat cgtcctttcc ttggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc tg              592
```

<210> SEQ ID NO 120
<211> LENGTH: 593
<212> TYPE: DNA
<213> ORGANISM: Artificial Sequence
<220> FEATURE:
<223> OTHER INFORMATION: MODIFIED PRE WITH PROMOTER SEQUENCE AND START

CODON

<400> SEQUENCE: 120

| aatcaacctc tggattacaa aaatttgtga aagattgact ggtattctta actatgttgc | 60 |
| tcctttacg ctatgtggat acgctgcttt aatgcctttg tatcatgcta ttgcttcccg | 120 |
| tatggctttc attttctcct ccttgtataa atcctggttg ctgtctcttt atgaggagtt | 180 |
| gtggcccgtt gtcaggcaac gtggcgtggt gtgcactgtg tttgctgacg caaccccac | 240 |
| tggttggggc attgccacca cctgtcagct cctttccggg actttcgctt tccccctccc | 300 |
| tattgccacg gcggaactca tcgccgcctg ccttgcccgc tgctggacag gggctcggct | 360 |
| gttgggcact gacaattccg tggtgttgtc ggggaaggtc tgctgagact cggggctgct | 420 |
| cgcctgtgtt gccacctgga ttctgcgcgg gacgtccttc tgctacgtcc cttcggccct | 480 |
| caatccagcg gaccttcctt cccgcggcct gctgccggct ctgcggcctc ttccgcgtct | 540 |
| tcgccttcgc cctcagacga gtcggatctc cctttgggcc gcctccccgc ctg | 593 |

<210> SEQ ID NO 121
<211> LENGTH: 179
<212> TYPE: DNA
<213> ORGANISM: Artificial Sequence
<220> FEATURE:
<223> OTHER INFORMATION: DNA FLAP REGION

<400> SEQUENCE: 121

| tacaaatggc agtattcatc cacaatttta aagaaaagg ggggattggg gggtacagtg | 60 |
| caggggaaag aatagtagac ataatagcaa cagacataca aactaaagaa ttacaaaaac | 120 |
| aaattacaaa aattcaaaat tttcgggttt attacaggga cagcagagat ccagtttgg | 179 |

<210> SEQ ID NO 122
<211> LENGTH: 136
<212> TYPE: DNA
<213> ORGANISM: Artificial Sequence
<220> FEATURE:
<223> OTHER INFORMATION: MODIFIED DNA FLAP REGION

<400> SEQUENCE: 122

| tacaaatggc agtattcatc cacaattttt tgggggtac agtgcagggg aagaatagt | 60 |
| agacataata gcaacagaca tacaaactaa agaattacaa cgggtttatt acagggacag | 120 |
| cagagatcca gtttgg | 136 |

<210> SEQ ID NO 123
<211> LENGTH: 16
<212> TYPE: DNA
<213> ORGANISM: Artificial Sequence
<220> FEATURE:
<223> OTHER INFORMATION: Central Polypurine Tract (cPPT)

<400> SEQUENCE: 123

| aaaagaaaag ggggga | 16 |

<210> SEQ ID NO 124
<211> LENGTH: 27
<212> TYPE: DNA
<213> ORGANISM: Artificial Sequence
<220> FEATURE:
<223> OTHER INFORMATION: Central Termination Sequence (CTS)

<400> SEQUENCE: 124

| aaacaaatta caaaaattca aaatttt | 27 |

<210> SEQ ID NO 125
<211> LENGTH: 589
<212> TYPE: DNA
<213> ORGANISM: Woodchuck Hepatitis Virus

<400> SEQUENCE: 125

| | | |
|---|---|---|
| aatcaacctc tggattacaa aatttgtgaa agattgactg gtattcttaa ctatgttgct | 60 |
| cctttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga cttttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaagctga cgtcctttcc atggctgctc | 420 |
| gcctgtgttg ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgc | 589 |

<210> SEQ ID NO 126
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 126

| | | |
|---|---|---|
| aatcaacctc tggattacaa aatttgtgaa agattgactg gtattcttaa ctatgttgct | 60 |
| cctttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga cttttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaagctga cgtcctttcc atggctgctt | 420 |
| agctgagtag ctgactggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgc | 589 |

<210> SEQ ID NO 127
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 127

| | | |
|---|---|---|
| aatcaacctc tggattacaa aatttgtgaa agattgactg gtattcttaa ctatgttgct | 60 |
| cctttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga cttttcgcttt ccccctccct | 300 |

```
attgccacgg cggaactcat cgccgcctgc cttgcccgct gctggacagg ggctcggctg    360
ttgggcactg acaattccgt ggtgttgtcg gggaagctga cgtcctttcc atggctgctt    420
agctgagtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 128
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 128

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga cttttgcttt ccccctccct    300
attgccacgg cggaactcat cgccgcctgc cttgcccgct gctggacagg ggctcggctg    360
ttgggcactg acaattccgt ggtgttgtcg gggaagctga cgtcctttcc atggctgctt    420
agctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 129
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 129

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga cttttgcttt ccccctccct    300
attgccacgg cggaactcat cgccgcctgc cttgcccgct gctggacagg ggctcggctg    360
ttgggcactg acaattccgt ggtgttgtcg gggaagctga cgtcctttcc atggctgctt    420
agctgtgtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 130
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 130

```
aatcaacctc tggattacaa aatttgtgaa agattgactg gtattcttaa ctatgttgct    60 cctttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga cttttcgcttt ccccctccct  300 attgccacgg cggaactcat cgccgcctgc cttgcccgct gctggacagg ggctcggctg   360
ttgggcactg acaattccgt ggtgttgtcg gggaagctga cgtcctttcc atggctgctc   420
gcctgagtag ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc               589
```

<210> SEQ ID NO 131
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 131

```
aatcaacctc tggattacaa aatttgtgaa agattgactg gtattcttaa ctatgttgct    60 cctttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga cttttcgcttt ccccctccct  300 attgccacgg cggaactcat cgccgcctgc cttgcccgct gctggacagg ggctcggctg   360
ttgggcactg acaattccgt ggtgttgtcg gggaagctga cgtcctttcc atggctgctt   420
agctgagttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc               589
```

<210> SEQ ID NO 132
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 132

```
aatcaacctc tggattacaa aatttgtgaa agattgactg gtattcttaa ctatgttgct    60 cctttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga cttttcgcttt ccccctccct  300 attgccacgg cggaactcat cgccgcctgc cttgcccgct gctggacagg ggctcggctg   360
ttgggcactg acaattccgt ggtgttgtcg gggaagctga cgtcctttcc atggctgctt   420
agctgtgtag ccacctggat tctgcgcggg acgtccttct gctacgtccc ttcggccctc   480
aatccagcgg accttccttc ccgcggcctg ctgccggctc tgcggcctct tccgcgtctt   540
```

```
<210> SEQ ID NO 133
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 133
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact   240
ggttggggca ttgccaccac ctgtcagctc ctttccggga ctttcgcttt cccctccct   300
attgccacgg cggaactcat cgccgcctgc cttgcccgct gctggacagg ggctcggctg   360
ttgggcactg acaattccgt ggtgttgtcg gggaagctga cgtcctttcc atggctgctc   420
agctgtgttg ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc               589

<210> SEQ ID NO 134
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 134
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact   240
ggttggggca ttgccaccac ctgtcagctc ctttccggga ctttcgcttt cccctccct   300
attgccacgg cggaactcat cgccgcctgc cttgcccgct gctggacagg ggctcggctg   360
ttgggcactg acaattccgt ggtgttgtcg gggaagctga cgtcctttcc atggctgctc   420
gcctgagtag ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc               589

<210> SEQ ID NO 135
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 135
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact   240
```

```
ggttggggca ttgccaccac ctgtcagctc ctttccggga cttccgcttt cccctccct    300 attgccacgg cggaactcat cgccgcctgc cttgcccgct gctggacagg ggctcggctg    360
ttgggcactg acaattccgt ggtgttgtcg gggaagctga cgtcctttcc atggctgctc    420
gcctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 136
<211> LENGTH: 589
<212> TYPE: DNA
<213> ORGANISM: Artificial Sequence
<220> FEATURE:
<223> OTHER INFORMATION: MODIFIED PRE WITH STOP CODONS

<400> SEQUENCE: 136

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240 ggttggggca ttgccaccac ctgtcagctc ctttccggga cttcgctttt cccctccct    300 attgccacgg cggaactcat cgccgcctgc cttgcccgct gctggacagg ggctcggctg    360
ttgggcactg acaattccgt ggtgttgtcg gggaagctga cgtcctttcc atggctgctc    420
gcctgtgtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 137
<211> LENGTH: 589
<212> TYPE: DNA
<213> ORGANISM: Artificial Sequence
<220> FEATURE:
<223> OTHER INFORMATION: MODIFIED PRE WITH STOP CODON

<400> SEQUENCE: 137

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240 ggttggggca ttgccaccac ctgtcagctc ctttccggga cttcgctttt cccctccct    300 attgccacgg cggaactcat cgccgcctgc cttgcccgct gctggacagg ggctcggctg    360
ttgggcactg acaattccgt ggtgttgtcg gggaagctga cgtcctttcc atggctgctc    420
agctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 138
<211> LENGTH: 589
<212> TYPE: DNA
<213> ORGANISM: Artificial Sequence
<220> FEATURE:

<223> OTHER INFORMATION: MODIFIED PRE WITH STOP CODON

<400> SEQUENCE: 138

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga cttttcgcttt ccccctccct    300
attgccacgg cggaactcat cgccgcctgc cttgcccgct gctggacagg ggctcggctg     360
ttgggcactg acaattccgt ggtgttgtcg gggaagctga cgtcctttcc atggctgctc     420
gcctgagttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc               589
```

<210> SEQ ID NO 139
<211> LENGTH: 589
<212> TYPE: DNA
<213> ORGANISM: Artificial Sequence
<220> FEATURE:
<223> OTHER INFORMATION: MODIFIED PRE WITH STOP CODON

<400> SEQUENCE: 139

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga cttttcgcttt ccccctccct    300
attgccacgg cggaactcat cgccgcctgc cttgcccgct gctggacagg ggctcggctg     360
ttgggcactg acaattccgt ggtgttgtcg gggaagctga cgtcctttcc atggctgctc     420
gcctgtgtag ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc               589
```

<210> SEQ ID NO 140
<211> LENGTH: 589
<212> TYPE: DNA
<213> ORGANISM: Artificial Sequence
<220> FEATURE:
<223> OTHER INFORMATION: MODIFIED PRE WITH STOP CODON

<400> SEQUENCE: 140

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga cttttcgcttt ccccctccct    300
attgccacgg cggaactcat cgccgcctgc cttgcccgct gctggacagg ggctcggctg     360
ttgggcactg acaattccgt ggtgttgtcg gggaagctga cgtcctttcc atggctgctc     420
gcctgtgttg ctgactggat tctgcgcggg acgtccttct gctacgtccc ttcggccctc     480
```

```
aatccagcgg accttccttc ccgcggcctg ctgccggctc tgcggcctct tccgcgtctt    540
cgccttcgcc ctcagacgag tcggatctcc ctttgggccg cctccccgc                589

<210> SEQ ID NO 141
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 141
atggctgctt agctgagtag ctgactggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 142
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 142
atggctgctt agctgagtag ccacctggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 143
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 143
atggctgctt agctgagttg ctgactggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 144
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 144
atggctgctt agctgtgtag ctgactggat tctgcgcggg acgtccttct gctacgtccc     60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 145
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 145
```
atggctgctc gcctgagtag ctgactggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 146
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 146
atggctgctt agctgagttg ccacctggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 147
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 147
atggctgctt agctgtgtag ccacctggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 148
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 148
atggctgctt agctgtgttg ctgactggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 149
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 149
atggctgctc gcctgagtag ccacctggat tctgcgcggg acgtccttct gctacgtccc    60
ttcggccctc aatccagcgg accttccttc ccgcggcctg ctgccggctc tgcggcctct    120
tccgcgtctt cgccttcgcc ctcagacgag tcggatctcc ctttgggccg cctccccgc    179

<210> SEQ ID NO 150
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 150

```
atggctgctc gcctgagttg ctgactggat tctgcgcggg acgtccttct gctacgtccc    60
ttcggccctc aatccagcgg accttccttc ccgcggcctg ctgccggctc tgcggcctct   120
tccgcgtctt cgccttcgcc ctcagacgag tcggatctcc ctttgggccg cctccccgc    179
```

<210> SEQ ID NO 151
<211> LENGTH: 179
<212> TYPE: DNA
<213> ORGANISM: Artificial Sequence
<220> FEATURE:
<223> OTHER INFORMATION: TRUNCATED X GENE WITH STOP CODONS

<400> SEQUENCE: 151

```
atggctgctc gcctgtgtag ctgactggat tctgcgcggg acgtccttct gctacgtccc    60
ttcggccctc aatccagcgg accttccttc ccgcggcctg ctgccggctc tgcggcctct   120
tccgcgtctt cgccttcgcc ctcagacgag tcggatctcc ctttgggccg cctccccgc    179
```

<210> SEQ ID NO 152
<211> LENGTH: 179
<212> TYPE: DNA
<213> ORGANISM: Artificial Sequence
<220> FEATURE:
<223> OTHER INFORMATION: TRUNCATED X GENE WITH STOP CODON

<400> SEQUENCE: 152

```
atggctgctt agctgtgttg ccacctggat tctgcgcggg acgtccttct gctacgtccc    60
ttcggccctc aatccagcgg accttccttc ccgcggcctg ctgccggctc tgcggcctct   120
tccgcgtctt cgccttcgcc ctcagacgag tcggatctcc ctttgggccg cctccccgc    179
```

<210> SEQ ID NO 153
<211> LENGTH: 179
<212> TYPE: DNA
<213> ORGANISM: Artificial Sequence
<220> FEATURE:
<223> OTHER INFORMATION: TRUNCATED X GENE WITH STOP CODON

<400> SEQUENCE: 153

```
atggctgctc gcctgagttg ccacctggat tctgcgcggg acgtccttct gctacgtccc    60
ttcggccctc aatccagcgg accttccttc ccgcggcctg ctgccggctc tgcggcctct   120
tccgcgtctt cgccttcgcc ctcagacgag tcggatctcc ctttgggccg cctccccgc    179
```

<210> SEQ ID NO 154
<211> LENGTH: 179
<212> TYPE: DNA
<213> ORGANISM: Artificial Sequence
<220> FEATURE:
<223> OTHER INFORMATION: TRUNCATED X GENE WITH STOP CODON

<400> SEQUENCE: 154

```
atggctgctc gcctgtgtag ccacctggat tctgcgcggg acgtccttct gctacgtccc    60
ttcggccctc aatccagcgg accttccttc ccgcggcctg ctgccggctc tgcggcctct   120
tccgcgtctt cgccttcgcc ctcagacgag tcggatctcc ctttgggccg cctccccgc    179
```

<210> SEQ ID NO 155
<211> LENGTH: 179
<212> TYPE: DNA
<213> ORGANISM: Artificial Sequence
<220> FEATURE:
<223> OTHER INFORMATION: TRUNCATED X GENE WITH STOP CODON

<400> SEQUENCE: 155

```
atggctgctc gcctgtgttg ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc      179
```

<210> SEQ ID NO 156
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 156

```
aatcaacctc tggattacaa aatttgtgaa agattgactg gtattcttaa ctatgttgct      60
ccttttacgc tatgtggata cgctgcttta atgcctttgt atcatgctat gcttcccgt     120 atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga cttttcgcttt ccccctccct    300 attgccacgg cggaactcat cgccgcctgc cttgcccgct gctggacagg ggctcggctg     360
ttgggcactg acaattccgt ggtgttgtcg gggaagctga cgtcctttcc ggggctgctt     420
agctgagtag ctgactggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc                 589
```

<210> SEQ ID NO 157
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 157

```
aatcaacctc tggattacaa aatttgtgaa agattgactg gtattcttaa ctatgttgct      60
ccttttacgc tatgtggata cgctgcttta atgcctttgt atcatgctat gcttcccgt     120 atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga cttttcgcttt ccccctccct    300 attgccacgg cggaactcat cgccgcctgc cttgcccgct gctggacagg ggctcggctg     360
ttgggcactg acaattccgt ggtgttgtcg gggaagctga cgtcctttcc ggggctgctt     420
agctgagtag ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc                 589
```

<210> SEQ ID NO 158
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 158

```
aatcaacctc tggattacaa aatttgtgaa agattgactg gtattcttaa ctatgttgct      60
```

```
cctttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccccact    240 ggttggggca ttgccaccac ctgtcagctc ctttccggga ctttcgcttt ccccctccct      300
attgccacgg cggaactcat cgccgcctgc cttgcccgct gctggacagg ggctcggctg      360
ttgggcactg acaattccgt ggtgttgtcg gggaagctga cgtcctttcc ggggctgctt     420
agctgagttg ctgactggat tctgcgcggg acgtccttct gctacgtccc ttcggccctc    480
aatccagcgg accttccttc ccgcggcctg ctgccggctc tgcggcctct tccgcgtctt     540
cgccttcgcc ctcagacgag tcggatctcc ctttgggccg cctccccgc               589
```

<210> SEQ ID NO 159
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 159

```
aatcaacctc tggattacaa aatttgtgaa agattgactg gtattcttaa ctatgttgct      60 cctttttacgc tatgtggata cgctgcttta atgcctttgt atcatgctat tgcttcccgt    120
atggctttca ttttctcctc cttgtataaa tcctggttgc tgtctcttta tgaggagttg     180
tggcccgttg tcaggcaacg tggcgtggtg tgcactgtgt ttgctgacgc aaccccccact   240 ggttggggca ttgccaccac ctgtcagctc ctttccggga ctttcgcttt ccccctccct     300
attgccacgg cggaactcat cgccgcctgc cttgcccgct gctggacagg ggctcggctg    360
ttgggcactg acaattccgt ggtgttgtcg gggaagctga cgtcctttcc ggggctgctt    420
agctgtgtag ctgactggat tctgcgcggg acgtccttct gctacgtccc ttcggccctc   480
aatccagcgg accttccttc ccgcggcctg ctgccggctc tgcggcctct tccgcgtctt    540
cgccttcgcc ctcagacgag tcggatctcc ctttgggccg cctccccgc               589
```

<210> SEQ ID NO 160
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 160

```
aatcaacctc tggattacaa aatttgtgaa agattgactg gtattcttaa ctatgttgct      60 cctttttacgc tatgtggata cgctgcttta atgcctttgt atcatgctat tgcttcccgt    120
atggctttca ttttctcctc cttgtataaa tcctggttgc tgtctcttta tgaggagttg     180
tggcccgttg tcaggcaacg tggcgtggtg tgcactgtgt ttgctgacgc aaccccccact   240 ggttggggca ttgccaccac ctgtcagctc ctttccggga ctttcgcttt ccccctccct     300
attgccacgg cggaactcat cgccgcctgc cttgcccgct gctggacagg ggctcggctg    360
ttgggcactg acaattccgt ggtgttgtcg gggaagctga cgtcctttcc ggggctgctc    420
gcctgagtag ctgactggat tctgcgcggg acgtccttct gctacgtccc ttcggccctc   480
aatccagcgg accttccttc ccgcggcctg ctgccggctc tgcggcctct tccgcgtctt    540
cgccttcgcc ctcagacgag tcggatctcc ctttgggccg cctccccgc               589
```

<210> SEQ ID NO 161
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 161

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact      240
ggttggggca ttgccaccac ctgtcagctc ctttccggga cttttcgcttt cccctccct    300
attgccacgg cggaactcat cgccgcctgc cttgcccgct gctggacagg ggctcggctg    360
ttgggcactg acaattccgt ggtgttgtcg gggaagctga cgtcctttcc ggggctgctt    420
agctgagttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 162
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 162

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact      240
ggttggggca ttgccaccac ctgtcagctc ctttccggga cttttcgcttt cccctccct    300
attgccacgg cggaactcat cgccgcctgc cttgcccgct gctggacagg ggctcggctg    360
ttgggcactg acaattccgt ggtgttgtcg gggaagctga cgtcctttcc ggggctgctt    420
agctgtgtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 163
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 163

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact      240
ggttggggca ttgccaccac ctgtcagctc ctttccggga cttttcgcttt cccctccct    300
```

```
attgccacgg cggaactcat cgccgcctgc cttgcccgct gctggacagg ggctcggctg    360
ttgggcactg acaattccgt ggtgttgtcg gggaagctga cgtcctttcc ggggctgctc    420
agctgtgttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 164
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 164

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact    240 ggttggggca ttgccaccac ctgtcagctc ctttccggga cttttcgctttt ccccctccct    300 attgccacgg cggaactcat cgccgcctgc cttgcccgct gctggacagg ggctcggctg    360
ttgggcactg acaattccgt ggtgttgtcg gggaagctga cgtcctttcc ggggctgctc    420
gcctgagtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 165
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 165

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact    240 ggttggggca ttgccaccac ctgtcagctc ctttccggga cttttcgctttt ccccctccct    300 attgccacgg cggaactcat cgccgcctgc cttgcccgct gctggacagg ggctcggctg    360
ttgggcactg acaattccgt ggtgttgtcg gggaagctga cgtcctttcc ggggctgctc    420
gcctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 166
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 166

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact  240
ggttggggca ttgccaccac ctgtcagctc ctttccggga cttttcgcttt ccccctccct  300
attgccacgg cggaactcat cgccgcctgc cttgcccgct gctggacagg ggctcggctg   360
ttgggcactg acaattccgt ggtgttgtcg gggaagctga cgtcctttcc ggggctgctc   420
gcctgtgtag ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc               589
```

<210> SEQ ID NO 167
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 167

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact  240
ggttggggca ttgccaccac ctgtcagctc ctttccggga cttttcgcttt ccccctccct  300
attgccacgg cggaactcat cgccgcctgc cttgcccgct gctggacagg ggctcggctg   360
ttgggcactg acaattccgt ggtgttgtcg gggaagctga cgtcctttcc ggggctgctt   420
agctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc               589
```

<210> SEQ ID NO 168
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 168

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact  240
ggttggggca ttgccaccac ctgtcagctc ctttccggga cttttcgcttt ccccctccct  300
attgccacgg cggaactcat cgccgcctgc cttgcccgct gctggacagg ggctcggctg   360
ttgggcactg acaattccgt ggtgttgtcg gggaagctga cgtcctttcc ggggctgctc   420
gcctgagttg ccacctggat tctgcgcggg acgtccttct gctacgtccc ttcggccctc   480
aatccagcgg accttccttc ccgcggcctg ctgccggctc tgcggcctct tccgcgtctt   540
```

```
cgccttcgcc ctcagacgag tcggatctcc ctttgggccg cctccccgc        589
```

<210> SEQ ID NO 169
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 169

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240
ggttggggca ttgccaccac ctgtcagctc ctttccggga cttcgctttt cccctccct    300
attgccacgg cggaactcat cgccgcctgc cttgcccgct gctggacagg ggctcggctg   360
ttgggcactg acaattccgt ggtgttgtcg gggaagctga cgtcctttcc ggggctgctc   420
gcctgtgtag ccacctggat tctgcgcggg acgtccttct gctacgtccc ttcggccctc   480
aatccagcgg accttccttc ccgcggcctg ctgccggctc tgcggcctct ccgcgtctt    540
cgccttcgcc ctcagacgag tcggatctcc ctttgggccg cctccccgc              589
```

<210> SEQ ID NO 170
<211> LENGTH: 589
<212> TYPE: DNA
<213> ORGANISM: Artificial Sequence
<220> FEATURE:
<223> OTHER INFORMATION: MODIFIED PRE WITH START AND STOP CODONS

<400> SEQUENCE: 170

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240
ggttggggca ttgccaccac ctgtcagctc ctttccggga cttcgctttt cccctccct    300
attgccacgg cggaactcat cgccgcctgc cttgcccgct gctggacagg ggctcggctg   360
ttgggcactg acaattccgt ggtgttgtcg gggaagctga cgtcctttcc ggggctgctc   420
gcctgtgttg ctgactggat tctgcgcggg acgtccttct gctacgtccc ttcggccctc   480
aatccagcgg accttccttc ccgcggcctg ctgccggctc tgcggcctct ccgcgtctt    540
cgccttcgcc ctcagacgag tcggatctcc ctttgggccg cctccccgc              589
```

<210> SEQ ID NO 171
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 171

```
ggggctgctt agctgagtag ctgactggat tctgcgcggg acgtccttct gctacgtccc    60
ttcggccctc aatccagcgg accttccttc ccgcggcctg ctgccggctc tgcggcctct   120
tccgcgtctt cgccttcgcc ctcagacgag tcggatctcc ctttgggccg cctccccgc   179
```

<210> SEQ ID NO 172
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 172
ggggctgctt agctgagtag ccacctggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179

<210> SEQ ID NO 173
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 173
ggggctgctt agctgagttg ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179

<210> SEQ ID NO 174
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 174
ggggctgctt agctgtgtag ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179

<210> SEQ ID NO 175
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 175
ggggctgctc gcctgagtag ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179

<210> SEQ ID NO 176
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 176

```
gggctgctt agctgagttg ccacctggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179
```

<210> SEQ ID NO 177
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 177

```
gggctgctt agctgtgtag ccacctggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179
```

<210> SEQ ID NO 178
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 178

```
gggctgctt agctgtgttg ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179
```

<210> SEQ ID NO 179
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 179

```
gggctgctc gcctgagtag ccacctggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179
```

<210> SEQ ID NO 180
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 180

```
gggctgctc gcctgagttg ctgactggat tctgcgcggg acgtccttct gctacgtccc      60
ttcggccctc aatccagcgg accttccttc ccgcggcctg ctgccggctc tgcggcctct     120
tccgcgtctt cgccttcgcc ctcagacgag tcggatctcc ctttgggccg cctccccgc     179
```

<210> SEQ ID NO 181
<211> LENGTH: 179
<212> TYPE: DNA

```
<213> ORGANISM: Artificial Sequence
<220> FEATURE:
<223> OTHER INFORMATION: TRUNCATED X GENE WITH MODIFIED START AND STOP
      CODONS

<400> SEQUENCE: 181
ggggctgctc gcctgtgtag ctgactggat tctgcgcggg acgtccttct gctacgtccc       60
ttcggccctc aatccagcgg accttccttc ccgcggcctg ctgccggctc tgcggcctct      120
tccgcgtctt cgccttcgcc ctcagacgag tcggatctcc ctttgggccg cctccccgc       179

<210> SEQ ID NO 182
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 182
ggggctgctt agctgtgttg ccacctggat tctgcgcggg acgtccttct gctacgtccc       60
ttcggccctc aatccagcgg accttccttc ccgcggcctg ctgccggctc tgcggcctct      120
tccgcgtctt cgccttcgcc ctcagacgag tcggatctcc ctttgggccg cctccccgc       179

<210> SEQ ID NO 183
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 183
ggggctgctc gcctgagttg ccacctggat tctgcgcggg acgtccttct gctacgtccc       60
ttcggccctc aatccagcgg accttccttc ccgcggcctg ctgccggctc tgcggcctct      120
tccgcgtctt cgccttcgcc ctcagacgag tcggatctcc ctttgggccg cctccccgc       179

<210> SEQ ID NO 184
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 184
ggggctgctc gcctgtgtag ccacctggat tctgcgcggg acgtccttct gctacgtccc       60
ttcggccctc aatccagcgg accttccttc ccgcggcctg ctgccggctc tgcggcctct      120
tccgcgtctt cgccttcgcc ctcagacgag tcggatctcc ctttgggccg cctccccgc       179

<210> SEQ ID NO 185
<211> LENGTH: 179
<212> TYPE: DNA
<213> ORGANISM: Artificial Sequence
<220> FEATURE:
<223> OTHER INFORMATION: TRUNCATED X GENE WITH MODIFIED START AND STOP
      CODONS

<400> SEQUENCE: 185
ggggctgctc gcctgtgttg ctgactggat tctgcgcggg acgtccttct gctacgtccc       60
ttcggccctc aatccagcgg accttccttc ccgcggcctg ctgccggctc tgcggcctct      120
```

```
tccgcgtctt cgccttcgcc ctcagacgag tcggatctcc ctttgggccg cctccccgc    179
```

<210> SEQ ID NO 186
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 186

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact  240
ggttggggca ttgccaccac ctgtcagctc ctttccggga cttttcgcttt ccccctccct  300
attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgagtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc               589
```

<210> SEQ ID NO 187
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 187

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact  240
ggttggggca ttgccaccac ctgtcagctc ctttccggga cttttcgcttt ccccctccct  300
attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgagtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc               589
```

<210> SEQ ID NO 188
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 188

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
```

```
atggctttca ttttctcctc cttgtataaa tcctggttgc tgtctcttta tgaggagttg    180
tggcccgttg tcaggcaacg tggcgtggtg tgcactgtgt ttgctgacgc aaccccact     240 ggttggggca ttgccaccac ctgtcagctc ctttccggga ctttcgcttt cccctccct     300 attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 189
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 189

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact     240 ggttggggca ttgccaccac ctgtcagctc ctttccggga ctttcgcttt cccctccct     300 attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgtgtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 190
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 190

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact     240 ggttggggca ttgccaccac ctgtcagctc ctttccggga ctttcgcttt cccctccct     300 attgccacgg cggaactcat cgccgcctgc cttgcccgct gctggacagg ggctcggctg    360
ttgggcactg acaattccgt ggtgttgtcg gggaaggtct gctgagactc atggctgctc    420
gcctgagtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 191
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 191

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga ctttcgcttt ccccctccct     300
attgccacgg cggaactcat cgccgcctgc cttgcccgct gctggacagg ggctcggctg     360
ttgggcactg acaattccgt ggtgttgtcg gggaaggtct gctgagactc atggctgctt     420
agctgagttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc                 589
```

<210> SEQ ID NO 192
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 192

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga ctttcgcttt ccccctccct     300
attgccacgg cggaactcat cgccgcctgc cttgcccgct gctggacagg ggctcggctg     360
ttgggcactg acaattccgt ggtgttgtcg gggaaggtct gctgagactc atggctgctt     420
agctgtgtag ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc                 589
```

<210> SEQ ID NO 193
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 193

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
```

```
ggttggggca ttgccaccac ctgtcagctc ctttccggga cttcgcttt cccctccct      300 attgccacgg cggaactcat cgccgcctgc cttgcccgct gctggacagg ggctcggctg    360
ttgggcactg acaattccgt ggtgttgtcg gggaaggtct gctgagactc atggctgctt    420
agctgtgttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 194  
<211> LENGTH: 589  
<212> TYPE: DNA  
<213> ORGANISM: Artificial Sequence  
<220> FEATURE:  
<223> OTHER INFORMATION: MODIFIED PRE WITH PROMOTER SEQUENCE AND STOP CODONS

<400> SEQUENCE: 194

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga cttcgcttt cccctccct      300 attgccacgg cggaactcat cgccgcctgc cttgcccgct gctggacagg ggctcggctg    360
ttgggcactg acaattccgt ggtgttgtcg gggaaggtct gctgagactc atggctgctc    420
gcctgagtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 195  
<211> LENGTH: 589  
<212> TYPE: DNA  
<213> ORGANISM: Artificial Sequence  
<220> FEATURE:  
<223> OTHER INFORMATION: MODIFIED PRE WITH PROMOTER SEQUENCE AND STOP CODONS

<400> SEQUENCE: 195

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga cttcgcttt cccctccct      300 attgccacgg cggaactcat cgccgcctgc cttgcccgct gctggacagg ggctcggctg    360
ttgggcactg acaattccgt ggtgttgtcg gggaaggtct gctgagactc atggctgctc    420
gcctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 196  
<211> LENGTH: 589  
<212> TYPE: DNA

<213> ORGANISM: Artificial Sequence
<220> FEATURE:
<223> OTHER INFORMATION: MODIFIED PRE WITH PROMOTER SEQUENCE AND STOP
      CODONS

<400> SEQUENCE: 196

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccact    240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaggtct gctgagactc atggctgctc   420
gcctgtgtag ctgactggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc              589
```

<210> SEQ ID NO 197
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODON

<400> SEQUENCE: 197

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccact    240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaggtct gctgagactc atggctgctt   420
agctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc              589
```

<210> SEQ ID NO 198
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODON

<400> SEQUENCE: 198

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccact    240
ggttggggca ttgccaccac ctgtcagctc ctttccggga ctttcgcttt ccccctccct   300
```

-continued

```
attgccacgg cggaactcat cgccgcctgc cttgcccgct gctggacagg ggctcggctg      360
ttgggcactg acaattccgt ggtgttgtcg gggaaggtct gctgagactc atggctgctc      420
gcctgagttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgc                  589
```

<210> SEQ ID NO 199
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODON

<400> SEQUENCE: 199

```
aatcaacctc tggattacaa aatttgtgaa agattgactg gtattcttaa ctatgttgct       60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact      240 ggttggggca ttgccaccac ctgtcagctc ctttccggga cttcgctttc ccccctccct      300
attgccacgg cggaactcat cgccgcctgc cttgcccgct gctggacagg ggctcggctg      360
ttgggcactg acaattccgt ggtgttgtcg gggaaggtct gctgagactc atggctgctc      420
gcctgtgtag ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgc                  589
```

<210> SEQ ID NO 200
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP
      CODON

<400> SEQUENCE: 200

```
aatcaacctc tggattacaa aatttgtgaa agattgactg gtattcttaa ctatgttgct       60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact      240 ggttggggca ttgccaccac ctgtcagctc ctttccggga cttcgctttc ccccctccct      300
attgccacgg cggaactcat cgccgcctgc cttgcccgct gctggacagg ggctcggctg      360
ttgggcactg acaattccgt ggtgttgtcg gggaaggtct gctgagactc atggctgctc      420
gcctgtgttg ctgactggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgc                  589
```

<210> SEQ ID NO 201
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND STOP

CODON

<400> SEQUENCE: 201

| aatcaacctc tggattacaa aatttgtgaa agattgactg gtattcttaa ctatgttgct | 60 |
| cctttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aacccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctt | 420 |
| agctgagtag ctgactggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgc | 589 |

<210> SEQ ID NO 202
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START AND STOP CODONS

<400> SEQUENCE: 202

| aatcaacctc tggattacaa aatttgtgaa agattgactg gtattcttaa ctatgttgct | 60 |
| cctttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aacccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctt | 420 |
| agctgagtag ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgc | 589 |

<210> SEQ ID NO 203
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START AND STOP CODONS

<400> SEQUENCE: 203

| aatcaacctc tggattacaa aatttgtgaa agattgactg gtattcttaa ctatgttgct | 60 |
| cctttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aacccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg ggctcggctg | 360 |
| ttgggcactg acaattccgt ggtgttgtcg gggaaggtct gctgagactc ggggctgctt | 420 |

```
agctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 204
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 204

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga cttcgctttc ccccctccct    300
attgccacgg cggaactcat cgccgcctgc cttgcccgct gctggacagg ggctcggctg    360
ttgggcactg acaattccgt ggtgttgtcg gggaaggtct gctgagactc ggggctgctt    420
agctgtgtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 205
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 205

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga cttcgctttc ccccctccct    300
attgccacgg cggaactcat cgccgcctgc cttgcccgct gctggacagg ggctcggctg    360
ttgggcactg acaattccgt ggtgttgtcg gggaaggtct gctgagactc ggggctgctc    420
gcctgagtag ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 206
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 206

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240 ggttggggca ttgccaccac ctgtcagctc ctttccggga cttcgcttt ccccctccct    300 attgccacgg cggaactcat cgccgcctgc cttgcccgct gctggacagg ggctcggctg   360
ttgggcactg acaattccgt ggtgttgtcg gggaaggtct gctgagactc ggggctgctt   420
agctgagttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc                589

<210> SEQ ID NO 207
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 207
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240 ggttggggca ttgccaccac ctgtcagctc ctttccggga cttcgcttt ccccctccct    300 attgccacgg cggaactcat cgccgcctgc cttgcccgct gctggacagg ggctcggctg   360
ttgggcactg acaattccgt ggtgttgtcg gggaaggtct gctgagactc ggggctgctt   420
agctgtgtag ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc                589

<210> SEQ ID NO 208
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 208
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240 ggttggggca ttgccaccac ctgtcagctc ctttccggga cttcgcttt ccccctccct    300 attgccacgg cggaactcat cgccgcctgc cttgcccgct gctggacagg ggctcggctg   360
ttgggcactg acaattccgt ggtgttgtcg gggaaggtct gctgagactc ggggctgctt   420
agctgtgttg ctgactggat tctgcgcggg acgtccttct gctacgtccc ttcggccctc   480
```

```
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 209
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 209

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaaggtct gctgagactc ggggctgctc    420
gcctgagtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 210
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 210

```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaaggtct gctgagactc ggggctgctc    420
gcctgagttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 211
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 211

```
aatcaacctc tggattacaa aatttgtgaa agattgactg gtattcttaa ctatgttgct    60
```

```
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact      240 ggttggggca ttgccaccac ctgtcagctc ctttccggga ctttcgcttt ccccctccct      300
attgccacgg cggaactcat cgccgcctgc cttgcccgct gctggacagg ggctcggctg      360
ttgggcactg acaattccgt ggtgttgtcg gggaaggtct gctgagactc ggggctgctc      420
gcctgtgtag ctgactggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgc                  589
```

<210> SEQ ID NO 212
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 212

```
aatcaacctc tggattacaa aatttgtgaa agattgactg gtattcttaa ctatgttgct      60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact      240 ggttggggca ttgccaccac ctgtcagctc ctttccggga ctttcgcttt ccccctccct      300
attgccacgg cggaactcat cgccgcctgc cttgcccgct gctggacagg ggctcggctg      360
ttgggcactg acaattccgt ggtgttgtcg gggaaggtct gctgagactc ggggctgctt      420
agctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgc                  589
```

<210> SEQ ID NO 213
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 213

```
aatcaacctc tggattacaa aatttgtgaa agattgactg gtattcttaa ctatgttgct      60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact      240 ggttggggca ttgccaccac ctgtcagctc ctttccggga ctttcgcttt ccccctccct      300
attgccacgg cggaactcat cgccgcctgc cttgcccgct gctggacagg ggctcggctg      360
ttgggcactg acaattccgt ggtgttgtcg gggaaggtct gctgagactc ggggctgctc      420
gcctgagttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgc                  589
```

<210> SEQ ID NO 214
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 214

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaggtct gctgagactc ggggctgctc    420
gcctgtgtag ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 215
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND STOP CODONS

<400> SEQUENCE: 215

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaggtct gctgagactc ggggctgctc    420
gcctgtgttg ctgactggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

<210> SEQ ID NO 216
<211> LENGTH: 589
<212> TYPE: DNA
<213> ORGANISM: Artificial Sequence
<220> FEATURE:
<223> OTHER INFORMATION: MODIFIED PRE WITH PROMOTER SEQUENCE AND START
      AND CODON

<400> SEQUENCE: 216

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
```

```
tggcccgttg tcaggcaacg tggcgtggtg tgcactgtgt ttgctgacgc aaccccccact    240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589
```

```
<210> SEQ ID NO 217
<211> LENGTH: 21
<212> TYPE: DNA
<213> ORGANISM: Artificial Sequence
<220> FEATURE:
<223> OTHER INFORMATION: MODIFIED X GENE PROMOTER

<400> SEQUENCE: 217
ggggaaatca tcgtcctttc c                                               21

<210> SEQ ID NO 218
<211> LENGTH: 14
<212> TYPE: DNA
<213> ORGANISM: Artificial Sequence
<220> FEATURE:
<223> OTHER INFORMATION: MODIFIED X GENE PROMOTER

<400> SEQUENCE: 218
atcatcgtcc tttc                                                       14

<210> SEQ ID NO 219
<211> LENGTH: 21
<212> TYPE: DNA
<213> ORGANISM: Artificial Sequence
<220> FEATURE:
<223> OTHER INFORMATION: MODIFIED X GENE PROMOTER

<400> SEQUENCE: 219
ggggaaggtc tgctgagact c                                               21

<210> SEQ ID NO 220
<211> LENGTH: 14
<212> TYPE: DNA
<213> ORGANISM: Artificial Sequence
<220> FEATURE:
<223> OTHER INFORMATION: MODIFIED X GENE PROMOTER

<400> SEQUENCE: 220
ggtctgctga gact                                                       14

<210> SEQ ID NO 221
<211> LENGTH: 24
<212> TYPE: DNA
<213> ORGANISM: Woodchuck Hepatitis Virus

<400> SEQUENCE: 221
atggctgctc gcctgtgttg ccac                                            24
```